(12) United States Patent
Lavallée et al.

(10) Patent No.: US 12,317,908 B2
(45) Date of Patent: *Jun. 3, 2025

(54) COMPOSITIONS COMPRISING *FABACEAE* FAMILY PLANT COMPONENTS, PROCESSES OF PREPARATION AND USES THEREOF

(71) Applicant: VIRENTIA INNOVATION INC., Québec (CA)

(72) Inventors: Pierre Lavallée, Deschambault-Grondines (CA); Réjean Desgagnés, St-Jean-Chrysostome (CA); Laurence Cambron-Fortin, Québec (CA); Louis-Philippe Vézina, Neuville (CA); Pierre Talbot, Notre-Dame-du-Portage (CA)

(73) Assignee: VIRENTIA INNOVATION INC. (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/641,133

(22) Filed: Apr. 19, 2024

(65) Prior Publication Data

US 2024/0315280 A1 Sep. 26, 2024

Related U.S. Application Data

(63) Continuation of application No. 18/033,134, filed as application No. PCT/CA2021/051482 on Oct. 21, 2021.

(Continued)

(51) Int. Cl.
| | |
|---|---|
| *A23K 10/30* | (2016.01) |
| *A23K 20/147* | (2016.01) |
| *A23K 20/158* | (2016.01) |
| *A23K 20/174* | (2016.01) |
| *A23K 20/179* | (2016.01) |
| *A23K 50/80* | (2016.01) |
| *A23L 33/105* | (2016.01) |

(Continued)

(52) U.S. Cl.
CPC ............ *A23K 10/30* (2016.05); *A23K 20/147* (2016.05); *A23K 20/158* (2016.05); *A23K 20/174* (2016.05); *A23K 20/179* (2016.05); *A23K 50/80* (2016.05); *A23L 33/105* (2016.08); *A23L 33/12* (2016.08); *A23L 33/15* (2016.08)

(58) Field of Classification Search
CPC .... A23K 10/30; A23K 20/158; A23K 20/174; A23K 30/10; A23K 30/20; A23L 33/105; A23L 2/52; A23L 33/15; A23L 5/44; A23L 33/185; A23L 33/16
USPC ........................................ 426/634, 655, 635
See application file for complete search history.

(56) References Cited

U.S. PATENT DOCUMENTS

| | | |
|---|---|---|
| 6,737,552 B1 | 5/2004 | Crombie |
| 11,672,261 B2 | 6/2023 | Lavallée et al. |

(Continued)

FOREIGN PATENT DOCUMENTS

| | | |
|---|---|---|
| AU | 502729 | 8/1979 |
| CA | 1004530 | 2/1977 |

(Continued)

OTHER PUBLICATIONS

John J. Evans, "Effect of pH on the Extraction and Fractionation of Dry Matter and Crude Protein from Coastal Bermuda Grass and White Clover", J. Agric. Food Chem. 1982, vol. 30, No. 2, 355-358. (The year of publication is sufficiently earlier than the effective U.S. filing date so the particular month of publication is not an issue.).

(Continued)

*Primary Examiner* — Hong T Yoo

(57) ABSTRACT

The present disclosure relates to a dry chloroplast composition comprising chloroplasts isolated from Fabaceae family plants. The composition has a moisture content of less than about 8%. The composition has at least one ratio chosen from:

a ratio of chlorophyll/fructose 1,6-biphosphatase (FBPP) of about 50 to about 130, the ratio of chlorophyll/FBPP being $$\frac{\text{chlorophyll in (mg/g)}}{FBPP \text{ in (intensity/mg powder)}} \times 10000000,$$

The FBPP intensity being measured by immunoblot,
a ratio of Rubisco/chlorophyll of about 25 to about 65, the ratio of Rubisco/chlorophyll being $$\left(\frac{\text{Rubisco in intensity}}{\text{chlorophyll in(mg/g)}}\right)/1000,$$

wherein the Rubisco intensity being measured by immunoblot,
a ratio of Rubisco/chlorophyll of about 2.5 ng/mg to about 6.5 ng/mg, the ratio of Rubisco/chlorophyll being $$\left(\frac{\text{Rubisco in ng/mg powder}}{\text{chlorophyll in(mg/g)}}\right)/1000,$$

and
a ratio of Rubisco/FBPP of about 18 to about 100, the ratio of Rubisco/FBPP being (Continued)

$$\left(\frac{\text{Rubisco in ng/mg powder}}{FBPP \text{ in intensity/mg}}\right) \times 100.$$

33 Claims, 32 Drawing Sheets

Related U.S. Application Data

(60) Provisional application No. 63/094,812, filed on Oct. 21, 2020.

(51) Int. Cl.
    *A23L 33/12*           (2016.01)
    *A23L 33/15*           (2016.01)

(56) References Cited

U.S. PATENT DOCUMENTS

| | | | |
|---|---|---|---|
| 12,004,537 B2* | 6/2024 | Lavallée | A01H 6/544 |
| 2009/0110674 A1 | 4/2009 | Loizou | |
| 2018/0105804 A1 | 4/2018 | Lo et al. | |
| 2018/0344787 A1 | 12/2018 | Iglesias et al. | |
| 2022/0211073 A1 | 7/2022 | Lavallée et al. | |
| 2023/0413853 A1 | 12/2023 | Lavallée et al. | |
| 2024/0000107 A1 | 1/2024 | Lavallée et al. | |

FOREIGN PATENT DOCUMENTS

| | | |
|---|---|---|
| JP | 2001178427 A | 7/2001 |
| WO | 2014104880 | 7/2014 |
| WO | 2017187109 | 11/2017 |
| WO | 2021235930 | 11/2021 |

OTHER PUBLICATIONS

Kobza et al., "Isolation of Photosynthetically Active Protoplast and Intact Chloroplasts from Phaseolus Vulgaris", Plant Science, 65 (Jul. 1989) 177-182.

Whitehouse et al., Chapter 11 "Isolation and Purification of Functionally Intact Chloroplast from Leaf Tissue and Leaf Tissue Protoplasts", Methods in Molecular Biology, vol. 19, Biomembrane Protocols, Isolation and Analysis (1993). (The year of publication is sufficiently earlier than the effective U.S. filing date so the particular month of publication is not an issue.).

Bialy et al., "Saponins in Alfalfa (*Medicago sativa* L.) Root and Their Structural Elucidation", Journal of Agriculture and Food Chemistry, 1999, vol. 47, pp. 3185-3189. (The year of publication is sufficiently earlier than the effective U.S. filing date so the particular month of publication is not an issue.).

Davys et al., "Batch Production of Protein from Leaves", Rothamsted Experimental Station, Harpenden, Herts (1963), pp. 70-73. (The year of publication is sufficiently earlier than the effective U.S. filing date so the particular month of publication is not an issue.).

Fafard et al., "Extraction of Protein from Chloroplast Isolated from Alfalfa Leaf", Journal of Food Biochemistry, Oct. 29, 1979, vol. 3, pp. 151-162.

Flores-Pérez et al., "Chapter 4—Isolation and Suborganellar Fractionation of *Arabidopsis* Chloroplasts", Taylor et al. (eds), Isolation of Plant Organelles and Structures: Methods and Protocols, Methods in Molecular Biology, vol. 1511, NY 2017. (The year of publication is sufficiently earlier than the effective U.S. filing date so the particular month of publication is not an issue.).

Khenblouche et al., "Extraction and Characterization of Cellulose Microfibers from Retama raetam stems", Polimeros, vol. 29 (Mar. 18, 2019).

Lilley et al., "Criteria of Intactness and the Photosynthetic Activity of Spinach Chloroplast Preparation", New Phytol. (Feb. 10, 1975), 75, 1-10.

Linden et al., "Chapter 3—Extraction and Texturisation Processes", New Ingredients in Food Processes—Biochmistry and Agriculture (1999) Woodhead Publishing Ltd. CRC Press. (The year of publication is sufficiently earlier than the effective U.S. filing date so the particular month of publication is not an issue.).

Stokilde et al., "Digestibility of Fractioned Green Biomass as Protein Source for Monogastric Animals", Animal, Published online Feb. 2019, vol. 13, pp. 1817-1825.

Subba Rau et al., "Nutritional on Whole Extract Coagulated Leaf Protein and Fractionated Chloroplastic and Cytoplasmic Proteins From Lucerne", Journal of the Science of Food and Agriculture, (Jun. 1969), vol. 20, pp. 355-358.

Tava et al., "Saponins from *Medicago* Spp: Chemical Characterization and Biological Activity Against Insects", Saponins used in Food and Agriculture, (1996), Waller & Yamasaki Editors, Plenum Press New York. (The year of publication is sufficiently earlier than the effective U.S. filing date so the particular month of publication is not an issue.).

Torcello-Gomez et al., "Chloroplast-rich material from the physical fractionation of pea vine (*Pisum sativum*) postharvest field residue (Haulm)", Food Chemistry, Published online Aug. 2018, vol. 272, pp. 18-25.

Udenigwe et al., "Ribulose-1,5-biphosphate carboxylase as a Sustainable and Promising Plant Source of Bioactive Peptides for Food Applications", Trends in Food Science & Technology, (2017), vol. 69, pp. 74-82.

Voudouris et al., "Sustainable Protein Technology; An evaluation on the STW Protein programme and an outlook for the future", Report 1786, published on Dec. 31, 2017.

English Translation—Machine Translated of WO2017187109A1, "Alfalfa Protein Hydrolysate, Method for Obtaining Same, and Use Thereof", published on Nov. 2, 2017.

J. Michael Robinson, "Photosynthetic Carbon Metabolism in Leaves and Isolated Chloroplasts from Spinach Plants Grown under Short and Intermediate Photosynthetic Periods", Plant Physiol. (Jan. 31, 1984) 75, 397-409.

Hernandez et al., "Solvent Extraction of Alfalfa Chloroplastic Curds", J. Sci. Food Agric. 1988, 43, 67-73. (The year of publication is sufficiently earlier than the effective U.S. filing date so that the particular month of publication is not an issue).

Abstract of Nadakavukaren et al., "Scanning Electron Microscopy of Isolated Chloroplasts", Journal of Submicroscopic Cytology, (1977), vol. 9, 2-3, 247-250. (The year of publication is sufficiently earlier than the effective U.S. filing date so that the particular month of publication is not an issue).

Lashko et al., "Isolation of Intact Chloroplasts from Alfalfa Leaves", Institute of Organoelementary Compounds, Academy of Sciences of the USSR, Moscow, vol. 37, No. 4, pp. 788-795, Jul.-Aug. 1990.

Cerovic et al., "An improved procedure for the isolation of intact chloroplasts of high photosynthetic capacity", Biochem. J. (1984) 223, 543-545. (The year of publication is sufficiently earlier than the effective U.S. filing date so that the particular month of publication is not an issue).

Vieira et al., "Replacement of living microalgae with a dried alfalfa chloroplast product in diets for the Brown mussel (*Perna perna*), Yellow clam (*Mesodesma macteroides*) and Manila clam (*Venerupis philippinarum*)", Agriculture Nutrition, Sep. 24, 2021; 27:2307-2319.

R. John Ellis et al., "The Rubisco subunit binding protein", Photosynthesis Reseach 16, 101-115 (Apr. 1988).

Salvucci et al., "Purification and Species Distribution of Rubisco Activase", Plant Physiol. (Jan. 1987) 84, 930-936.

Cline et al., "Separation and characterization of inner and outer envelope membranes of pea chloroplasts", Proc. Natl. Acad. Sci. USA, vol. 78, No. 6, pp. 3595-3599, Jun. 1981.

Google search report for fiber (Retrieved on May 5, 2022), 2022.

Lorna J. Gibson, "The hierarchical structure and mechanics of plant materials", J. R. Soc. Interface (Aug. 8, 2012) 9, 2749-2766.

(56) References Cited

OTHER PUBLICATIONS

Google : "What is the average size of chloroplast", [online][retrieved on Nov. 14, 2023] retrieved from https://www.google.com/search?hl=en&source-hp&biw=&bih=&q=what+is+the+average+size+of+chloroplast.

Gedi et al., "Component analysis of nutritionally rich chloroplasts: recovery from conventional and uncoventional green plant species", J Food Sci Technol (Aug. 2017) 54(9):2746-2757.

Minami et al., "Localization and Properties of Transcripts of psbA and rbcL Genes in the Stroma of Spinach Chloroplast", Plant Cell Physiol. 29(8): 1303-1309 (Aug. 23, 1988).

Englist Translation—Machine Translation of JP2001178427A, "Dehydrated matter of plant and beverage, food and feed for animal plankton using the same and method for producing dehydrated matter of plant", published on Jul. 3, 2001.

Walker et al., "Isolation of Intact Chloroplasts: General Principles and Criteria of Integrity", Methods in Enzymology, 1987, vol. 148, pp. 145-157. (The year of publication is sufficiently earlier than the effective U.S. filing date so that the particular month of publication is not an issue).

Google Search (Retrieved on Jul. 11, 2024, to get Intact Reference, NPL Walker, 1987 (Year: 2024). (The year of publication is sufficiently earlier than the effective U.S. filing date so that the particular month of publication is not an issue).

\* cited by examiner

COMPOSITIONS COMPRISING *FABACEAE* FAMILY PLANT COMPONENTS, PROCESSES OF PREPARATION AND USES THEREOF

CROSS-REFERENCE TO RELATED APPLICATION

The present disclosure is a continuation application of U.S. Ser. No. 18/033,134 filed on Apr. 21, 2023 (issued as U.S. Pat. No. 12,004,537 on Jun. 11, 2024), that is a 35 USC 371 national stage entry of PCT/CA2021/051482 filed on Oct. 21, 2021, and which claims priority to U.S. Provisional Application No. 63/094,812 filed on Oct. 21, 2020. These documents are hereby incorporated by reference in their entirety.

FIELD OF THE DISCLOSURE

The present disclosure relates to compositions and precursors comprising leafy plant components, such as Fabaceae family plant components, processes for preparing and uses thereof, and more particularly to compositions and precursors comprising *Medicago sativa* components, processes for preparing and uses thereof.

BACKGROUND OF THE DISCLOSURE

For centuries, agriculture has been using plant biomass as source for bulk protein and carbohydrate nutriments. As most of these components traditionally came from plant storage organs (fruits, seeds, storage stems, roots), their composition had a strong bias towards elements that were meant to be readily available to the developing embryo (seeds) or the developing shoot (storage root). As a consequence, overuse of these carbohydrate and protein-rich seeds or roots have impacted negatively on the evolution of human and animal diets. For example, in Western Societies, as proteins from plant storage organs (raw or processed) generally lack amino acids that are essential to humans, and are devoid of other essential nutritional components, they have been neglected as source of protein, and almost solely used as animal feed, where the nutritional balance is attained through addition of various complementary components.

Human nutrition is now at a turning point as two conclusions are drawn: first, using conventional plant biomass for the production of meat (animal protein) has a dramatic negative environmental impact, and, second, using conventional plant products (storage organs) as protein source for human nutrition is inadequate.

Plants do contain protein of equal or superior quality to animal protein. These are just rarely found in conventional plant products as they are found in photosynthetic organs, such as leaf and other aerial plant tissue or organs. And, leaves of certain plant species and genera contain more of this high-quality protein than others. In general, the higher their photosynthetic activity (per g of leaf) the higher is their chloroplast content and the higher their content of high-quality protein on a dry matter basis. In addition, for photosynthetic organs, the higher is the chloroplast content, the higher is the omega-3 phospholipid content, that are the building blocks of thylakoid membranes. Thus, it appears that photosynthetic organs, the most common and abundant being leaves, can be a sustainable and valued source of high-quality protein and lipids.

On the other hand, this type of biomass from plant origin may provide value-added compounds or molecules (other than protein and lipid) for different types of industries such as those related to human and animal health, human nutrition, animal nutrition, biocontrol of certain pathogens and biostimulation of plants. Photosynthetic biomass can come from algae, whether microscopic or not, or from terrestrial plants grown naturally or by humans.

Whether cultivated or harvested, obtaining industrial quantities of algae has been shown to be complex and costly which greatly limits their use. Many terrestrial plants have been found to be more efficient. Among these, the plants of the Fabaceae family are particularly interesting because of their high productivity, high protein content and their interaction with gaseous nitrogen-fixing bacteria able to meet 100% of their nitrogen fertilization needs. In particular, Fabaceae family plants, for example Trifolieae tribe plants have a high protein content in their leaves.

Among Fabaceae family plants, alfalfa (*Medicago sativa*) is particularly advantageous. According to some studies, one hectare of alfalfa can produce five times more protein than one hectare of soybeans. In addition, alfalfa has a very deep root system that greatly reduces its water requirements. Interestingly, the depth of the root network allows for the permanent accumulation of organic carbon in the soil from atmospheric $CO_2$, and consequently to potentially obtain credits that can be traded in the context of a developing carbon economy. In addition, alfalfa foliage has an exceptional nutritional profile especially in terms of its protein content, amino acids and vitamins A, B, D, E, C and K. It is also an interesting source of minerals such as calcium, sodium, magnesium, potassium and zinc. In fact, alfalfa provides almost all the elements necessary for the proper functioning of the human body. For example, its amino acid composition is close to that of milk and includes 14 amino acids, eight of which are essential for human health. Finally, it should be mentioned that certain parts or tissues of alfalfa may contain different compounds or molecules of increasing economic interest, in a society seeking for alternatives to man-created and synthetically produced chemicals. Among these molecules or compounds of interest include for example triacontanol (fatty alcohol with biostimulation effect on plants), coumestrol (estrogen type molecule), heat shock protein HSP70 (stress protein with therapeutic potential), albumin peptide Pa1b (entomotoxic peptide), Rubisco (enzyme with high nutritional value) and saponin (terpene with surfactant, anti-cholesterol and bioinsecticidal effects). However, it is important to note that saponin affects the dietary value of alfalfa for animals given its toxicity at too high doses.

To date, the full value of alfalfa, and other plants of interest of the same type, is under exploited because of the absence of an industrial process capable of preserving properties and structures specific to each of the different components of the plant that can be valorized or upgraded. In many situations, the equipment and operating parameters used create physical, chemical and/or biological stresses that irreversibly affect the value of many of the valorizable or recoverable components. In fact, most other plant fractionation processes use excessive mechanical strength for disruption, high temperatures and/or extreme pH conditions for coagulation and during fractionation, resulting in breakage of chloroplast integrity and release of the key Rubisco protein component in the liquid fraction. This strongly reduces protein quality of the chloroplast concentrates resulting from such fractionation and makes Rubisco recovery from the liquid fraction extremely challenging. In addition, use of high temperatures and/or extreme pH conditions for coagulation and during fractionation results in increased oxidative decay of major nutritional solutes, for example but without restriction, carotenes, chlorophyll, antioxidants, anthocyanins, proteins, omega-3 phospholipids, which are all heat labile and pH sensitive. In other situations, small-scale techniques are impossible to implement on an industrial scale required to support commercial activity. There is therefore a need for a fractionation process of alfalfa, and other species of interest, which preserves the value of the main valorizable or recoverable components of the plant and thus develop a maximum of innovative products with high value which eliminates the production of solid waste to dispose of and the need for treatment of existing liquid waste.

SUMMARY OF THE DISCLOSURE

Several plants, particularly Fabaceae family plants and more particularly *Medicago* spp plants, have a rich content of structures, compounds and molecules of great value, including proteins, which, given their intrinsic properties, may be easily altered by surrounding chemical, physical and microbiological conditions. The present disclosure relates to fractionation processes of plant fragments of economic interest, more particularly of *Medicago* spp plants. The process comprises four distinct fractionations that provides various products which may be directly used as value-added end products and/or be subject to further extraction or purification to obtain high-value compounds or molecules as active ingredients for further development of products intended to be used in various industries. The first fractionation mainly generates macrofibers. The second fractionation mainly generates microfibers. The third fractionation mainly generates products mostly devoid of chloroplasts, such as for example a saponin extract. The fourth fractionation mainly generates chloroplasts, unchanged or slightly altered, suspended in a liquid fraction or not. The preservation of the original and intrinsic qualities of the elements constituting the latter fraction gives it a great commercial interest; this is made possible by the mitigation, at each stage of the process, of chemical, physical and microbiological stresses. This mitigation is mainly based on one or more of the following factors: attenuation of shear forces, resulting from the separation of fibers at the beginning of the process and on the constant use of low energy dissipation equipment, maintaining of temperature at or below 45° C., maintaining of pH above 4 and adding of antioxidant and/or antimicrobial agents at specific process activities. Based on the foregoing, the by-products of one fractionation becomes the raw material for the next fractionation. As such, taken as a whole, the process generates a small volume of liquid waste, containing minimal organic matter, and is easily degradable.

Accordingly, an aspect herein disclosed is a chloroplast suspension having at least one ratio chosen from:
a ratio of chlorophyll/FBPP of about 50 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{FBPP \text{ in (intensity/mg powder)}} \times 10000000,$$

the FBPP intensity being measured by immunoblot,
a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in(mg/g)}}\right)/1000,$$

wherein the Rubisco intensity being measured by immunoblot,
a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in(mg/g)}}\right)/1000,$$

and
a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{FBPP \text{ in intensity/mg}}\right) \times 100.$$

Accordingly, an aspect herein disclosed is a chloroplast suspension comprising chloroplasts and water, the composition having a solid content of at least 25% w/v, wherein the chloroplasts are isolated from Fabaceae family plants,
wherein said chloroplast suspension has at least one ratio chosen from:
a ratio of chlorophyll/FBPP of about 50 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{FBPP \text{ in (intensity/mg powder)}} \times 10000000,$$

the FBPP intensity being measured by immunoblot,
a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{FBPP \text{ in intensity/mg}}\right) \times 100.$$

Another aspect relates to a chloroplast suspension comprising chloroplasts and water, wherein at least 75% of the chloroplasts comprised in the composition are intact e.g. as determined by dynamic light scattering measurement and analysis and wherein the chloroplasts are isolated from Fabaceae family plants,
  wherein said chloroplast suspension has at least one ratio chosen from:
    a ratio of chlorophyll/FBPP of about 50 to about 130, about 80 to about 120, about 90 to about 110, about 95 to about 105, about 97 to about 100 or about 98 to 100, the ratio of chlorophyll/FBPP being the FBPP intensity being $$\frac{\text{chlorophyll in (mg/g)}}{FBPP \text{ in (intensity/mg powder)}} \times 10000000,$$

the FBPP intensity being measured by immunoblot,
    a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
    a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{FBPP \text{ in intensity/mg}}\right) \times 100.$$

Another aspect relates to a chloroplast suspension comprising chloroplasts and water, wherein the suspension has a decrease in saponin content of about 20% to about 95%, about 20% to about 30%, about 20% to about 95%, about 70% to about 90%, about 70% to 80%, about 80% to about 90%, about 90% to about 95%, or more than 90% relative to a reference *Medicago* spp plant
  wherein said chloroplast suspension has at least one ratio chosen from:
    a ratio of chlorophyll/FBPP of about 50 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{FBPP \text{ in (intensity/mg powder)}} \times 10000000,$$

the FBPP intensity being measured by immunoblot,
    a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
    a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{FBPP \text{ in intensity/mg}}\right) \times 100.$$

Another aspect relates to a chloroplast suspension comprising chloroplasts and water, wherein the suspension has a decrease in medicagenic acid saponin content of about 0.3 mg/g to about 2.4 mg/g (dry basis) relative to a reference *Medicago* spp plant,
  wherein said chloroplast suspension has at least one ratio chosen from:
    a ratio of chlorophyll/FBPP of about 50 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{FBPP \text{ in (intensity/mg powder)}} \times 10000000,$$

the FBPP intensity being measured by immunoblot,
a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right)\times 100.$$

Another aspect relates to a chloroplast suspension comprising chloroplasts and water, wherein the suspension has a medicagenic acid saponin content of about 1.0 to about 6.4 mg/g (dry basis), wherein at least 75% of the chloroplasts comprised in the composition are intact e.g. as determined by dynamic light scattering measurement and analysis,
wherein said chloroplast suspension has at least one ratio chosen from:
a ratio of chlorophyll/FBPP of about 50 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{\text{FBPP in (intensity/mg powder)}}\times 10000000,$$

the FBPP intensity being measured by immunoblot,
a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right)\times 100.$$

Another aspect relates to a process for preparing a chloroplast suspension, said process comprising:
pressing Fabaceae family plant fragments to obtain pressed plant fragments;
separating a macrofiber depleted suspension from the pressed plant fragments;
separating a microfiber fraction comprising plant microfibers from the macrofiber depleted suspension;
obtaining a microfiber depleted suspension;
separating chloroplasts from the microfiber depleted suspension;
obtaining the chloroplast suspension; and
optionally washing the chloroplast suspension,
wherein at least 75% or about 75% to about 95% of non-chloroplast cellular content or soluble content outside of chloroplasts is removed from the microfiber depleted suspension, and/or wherein said chloroplast suspension has at least one ratio chosen from:
a ratio of chlorophyll/FBPP of about 50 to about 130, about 80 to about 120, about 90 to about 110, about 95 to about 105, about 97 to about 100 or about 98 to 100, the ratio of chlorophyll/FBPP being the FBPP intensity being $$\frac{\text{chlorophyll in (mg/g)}}{\text{FBPP in (intensity/mg powder)}}\times 10000000,$$

the FBPP intensity being measured by immunoblot,
a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right) \times 100.$$

Another aspect relates to a chloroplast suspension obtained according to a process herein disclosed,
  wherein at least 75% or about 75% to about 95% of non-chloroplast cellular content or soluble content outside of chloroplasts is removed from the microfiber depleted suspension, and/or wherein said chloroplast suspension has at least one ratio chosen from:
    a ratio of chlorophyll/FBPP of about 50 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{\text{FBPP in (intensity/mg powder)}} \times 10000000,$$

the FBPP intensity being measured by immunoblot,
    a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
    a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
    a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right) \times 100.$$

A washed chloroplast suspension having at least one ratio chosen from:
    a ratio of chlorophyll/FBPP of about 50 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{\text{FBPP in (intensity/mg powder)}} \times 10000000,$$

the FBPP intensity being measured by immunoblot,
    a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
    a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
    a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right) \times 100.$$

A washed chloroplast suspension obtained according to a process herein disclosed,
  wherein at least 75% or about 75% to about 95% of non-chloroplast cellular content or soluble content outside of chloroplasts is removed from the microfiber depleted suspension, and/or wherein said chloroplast suspension has at least one ratio chosen from:
    a ratio of chlorophyll/FBPP of about 50 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{\text{FBPP in (intensity/mg powder)}} \times 10000000,$$

the FBPP intensity being measured by immunoblot,
a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right)\times 100.$$

A liquid chloroplast composition that has at least one ratio chosen from:
a ratio of chlorophyll/FBPP of about 50 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{\text{FBPP in (intensity/mg powder)}}\times 10000000,$$

the FBPP intensity being measured by immunoblot,
a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right)\times 100.$$

A liquid chloroplast composition comprising chloroplasts isolated from Fabaceae family plants and suspended in water,
wherein said liquid chloroplast composition has at least one ratio chosen from:
a ratio of chlorophyll/FBPP of about 50 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{\text{FBPP in (intensity/mg powder)}}\times 10000000,$$

the FBPP intensity being measured by immunoblot,
a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right)\times 100.$$

13

A liquid chloroplast composition comprising chloroplasts isolated from Fabaceae family plants and suspended in water, the composition having a solid content of at least 25% w/v,
  wherein said liquid chloroplast composition has at least one ratio chosen from:
    a ratio of chlorophyll/FBPP of about 50 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{FBPP \text{ in (intensity/mg powder)}} \times 10000000,$$

the FBPP intensity being measured by immunoblot,
    a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
    a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
    a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{FBPP \text{ in intensity/mg}}\right) \times 100.$$

A liquid chloroplast composition comprising chloroplasts isolated from Fabaceae family plants and suspended in water, wherein at least 75% of the chloroplasts comprised in the composition are intact e.g. as determined by dynamic light scattering measurement and analysis,
  wherein said liquid chloroplast composition has at least one ratio chosen from:
    a ratio of chlorophyll/FBPP of about 50 to about 130, about 80 to about 120, about 90 to about 110, about 95 to about 105, about 97 to about 100 or about 98 to 100, the ratio of chlorophyll/FBPP being the FBPP intensity being $$\frac{\text{chlorophyll in (mg/g)}}{FBPP \text{ in (intensity/mg powder)}} \times 10000000,$$

14 the FBPP intensity being measured by immunoblot,
    a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
    a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
    a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{FBPP \text{ in intensity/mg}}\right) \times 100.$$

A liquid chloroplast composition comprising chloroplasts isolated from Fabaceae family plants and suspended in water, wherein the composition has a decrease in saponin content of about 20% to about 95%, about 20% to about 30%, about 70% to about 95%, about 70% to about 90%, about 70% to 80%, about 80% to about 90%, about 90% to about 95%, or more than 90% relative to a reference *Medicago* spp plant,
  wherein said liquid chloroplast composition has at least one ratio chosen from:
    a ratio of chlorophyll/FBPP of about 50 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{FBPP \text{ in (intensity/mg powder)}} \times 10000000,$$

the FBPP intensity being measured by immunoblot,
    a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right) \times 100.$$

A liquid chloroplast composition comprising chloroplasts isolated from Fabaceae family plants and suspended in water, wherein the composition has a decrease in medicagenic acid saponin content of about 0.3 mg/g to about 2.4 mg/g (dry basis) relative to a reference *Medicago* spp plant, wherein said liquid chloroplast composition has at least one ratio chosen from:
a ratio of chlorophyll/FBPP of about 50 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{\text{FBPP in (intensity/mg powder)}} \times 10000000,$$

the FBPP intensity being measured by immunoblot,
a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right) \times 100.$$

A liquid chloroplast composition comprising chloroplasts isolated from Fabaceae family plants and suspended in water, wherein the composition has a medicagenic acid saponin content of about 1.0 to about 6.4 mg/g (dry basis), wherein at least 75% of the chloroplast comprised in the composition are intact e.g. as determined by dynamic light scattering measurement and analysis,
wherein said liquid chloroplast composition has at least one ratio chosen from:
a ratio of chlorophyll/FBPP of about 50 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{\text{FBPP in (intensity/mg powder)}} \times 10000000,$$

the FBPP intensity being measured by immunoblot,
a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right) \times 100.$$

Another aspect relates to a ready to use liquid chloroplast composition comprising a composition herein described, and being disposed within a sealed pail or container, optionally filled with $N_2$ or nitrogen.

Another aspect relates to a use of the liquid chloroplast composition herein described, for feeding marine organisms.

Another aspect relates to a use of the liquid chloroplast composition herein described, in the manufacture of food for animals and/or humans.

Another aspect relates to a use of the liquid chloroplast composition herein described, in the manufacture of a cosmetic product.

Another aspect relates to a process for preparing a liquid chloroplast composition comprising chloroplasts suspended in water, said process comprising:
- pressing Fabaceae family plant fragments;
- separating a macrofiber depleted suspension from the pressed plant fragments;
- separating the plant microfibers from the macrofiber depleted suspension;
- obtaining a microfiber depleted suspension;
- separating chloroplasts from the microfiber depleted suspension;
- obtaining the chloroplast suspension;
- washing the chloroplast suspension; and
- conditioning the washed chloroplast suspension to obtain the liquid chloroplast composition, the conditioning comprising at least one step chosen from mixing the chloroplast suspension, adjusting the salinity and/or molarity of the chloroplast suspension, mixing the chloroplast suspension with a formulating agent, a conservation agent, a food supplement, an omega-3 fatty acid, an omega-6 fatty acid, or mixtures thereof, packaging the chloroplast suspension, encapsulating the chloroplast suspension, and mixtures thereof,
- wherein at least 75% of the chloroplasts comprised in the composition are intact e.g. as determined by dynamic light scattering measurement and analysis, and
- optionally wherein the washed chloroplast suspension and/or the liquid chloroplast composition comprise about 90% of the Rubisco content in the chloroplast suspension, wherein at least 75% or about 75% to about 95% of non-chloroplast cellular content or soluble content outside of chloroplasts is removed from the microfiber depleted suspension, and/or wherein said liquid chloroplast composition has at least one ratio chosen from:

a ratio of chlorophyll/FBPP of about 50 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{FBPP \text{ in (intensity/mg powder)}} \times 10000000,$$

the FBPP intensity being measured by immunoblot, a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right) / 1000,$$

wherein the Rubisco intensity being measured by immunoblot, a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right) / 1000,$$

and a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{FBPP \text{ in intensity/mg}}\right) \times 100.$$

Another aspect relates to a liquid chloroplast composition comprising chloroplasts suspended in water, obtained according to the process herein described, wherein at least 75% or about 75% to about 95% of non-chloroplast cellular content or soluble content outside of chloroplasts is removed from the microfiber depleted suspension, and/or wherein said liquid chloroplast composition has at least one ratio chosen from:

a ratio of chlorophyll/FBPP of about 50 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{FBPP \text{ in (intensity/mg powder)}} \times 10000000,$$

the FBPP intensity being measured by immunoblot, a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right) / 1000,$$

wherein the Rubisco intensity being measured by immunoblot, a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right) / 1000,$$

and
a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right) \times 100.$$

Another aspect relates to a dry chloroplast composition comprising chloroplasts isolated from Fabaceae family plants, wherein said dry chloroplast composition has at least one ratio chosen from:
a ratio of chlorophyll/FBPP of about 50 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{\text{FBPP in (intensity/mg powder)}} \times 10000000,$$

the FBPP intensity being measured by immunoblot,
a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right) \times 100.$$

Another aspect relates to a dry chloroplast composition comprising chloroplasts isolated from Fabaceae family plants, wherein said composition has a moisture content of less than about 8%,
and wherein said dry chloroplast composition has at least one ratio chosen from:
a ratio of chlorophyll/FBPP of about 50 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{\text{FBPP in (intensity/mg powder)}} \times 10000000,$$

the FBPP intensity being measured by immunoblot,
a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right) \times 100.$$

A dry chloroplast composition comprising chloroplasts isolated from Fabaceae family plants, wherein at least 75% of the chloroplasts comprised in the composition are intact e.g. as determined by dynamic light scattering measurement and analysis,
and wherein said dry chloroplast composition has at least one ratio chosen from:
a ratio of chlorophyll/FBPP of about 50 to about 130, about 80 to about 120, about 90 to about 110, about 95 to about 105, about 97 to about 100 or about 98 to 100, the ratio of chlorophyll/FBPP being.

$$\frac{\text{chlorophyll in (mg/g)}}{\text{FBPP in (intensity/mg powder)}} \times 10000000,$$

the FBPP intensity being measured by immunoblot,
a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right) \times 100.$$

Another aspect relates to a dry chloroplast composition comprising chloroplasts isolated from Fabaceae family plants, wherein the composition has a decrease in saponin content of about 20% to about 95%, about 20% to about 30%, about 70% to about 95%, about 70% to about 90%, about 70% to 80%, about 80% to about 90%, about 90% to about 95%, or more than 90% relative to a reference *Medicago* spp plant,
and wherein said dry chloroplast composition has at least one ratio chosen from:
a ratio of chlorophyll/FBPP of about 50 to about 130, about 80 to about 120, about 90 to about 110, about 95 to about 105, about 97 to about 100 or about 98 to 100, the ratio of chlorophyll/FBPP being $$\frac{\text{chlorophyll in(mg/g)}}{\text{FBPP in (intensity/mg powder)}} \times 10000000,$$

the FBPP intensity being measured by immunoblot,
a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right) \times 100.$$

Another aspect relates to a dry chloroplast composition comprising chloroplasts isolated from Fabaceae family plants and suspended in water, wherein the composition has a decrease in medicagenic acid saponin content of about 0.3 mg/g to about 2.4 mg/g (dry basis) relative to a reference *Medicago* spp plant,
and wherein said dry chloroplast composition has at least one ratio chosen from:
a ratio of chlorophyll/FBPP of about 50 to about 130, about 80 to about 120, about 90 to about 110, about 95 to about 105, about 97 to about 100 or about 98 to 100, the ratio of chlorophyll/FBPP being $$\frac{\text{chlorophyll in(mg/g)}}{\text{FBPP in (intensity/mg powder)}} \times 10000000,$$

the FBPP intensity being measured by immunoblot,
a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right) \times 100.$$

Another aspect relates to a dry chloroplast composition comprising chloroplasts isolated from Fabaceae family plants and suspended in water, wherein the composition has a medicagenic acid saponin content of about 1.0 to about 6.4 mg/g (dry basis), wherein n at least 75% of the chloroplast comprised in the composition are intact e.g. as determined by dynamic light scattering measurement and analysis, and wherein said dry chloroplast composition has at least one ratio chosen from:
a ratio of chlorophyll/FBPP of about 50 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{\text{FBPP in (intensity/mg powder)}} \times 10000000,$$

the FBPP intensity being measured by immunoblot,
a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right) \times 100.$$

Another aspect relates to a ready to use liquid chloroplast composition comprising the composition herein described, and being disposed within a sealed pail or container, optionally filled with $N_2$ or nitrogen.

Another aspect relates to a use of the dry chloroplast composition herein described, for feeding animals and/or humans.

Another aspect relates to a use of the dry chloroplast composition herein described, in the manufacture of food for animals and/or humans.

Another aspect relates to a use of the dry chloroplast composition herein described, in the manufacture of a nutritional supplement for animals and/or humans.

Another aspect relates to a use of the dry chloroplast composition herein described, in the manufacture of a cosmetic product.

Another aspect relates to a method for feeding marine organisms, said method comprising replacing at least a portion of microalgae and/or cyanobacteria provided in a diet for said marine organisms by the dry chloroplast composition herein described.

Another aspect relates to a process for preparing a dry chloroplast composition, said process comprising:
providing Fabaceae family plant fragments;
separating a macrofiber depleted suspension from the plant fragments;
separating the plant microfibers from the macrofiber depleted suspension;
obtaining a microfiber depleted suspension;
separating chloroplasts from the microfiber depleted suspension;
obtaining the chloroplast suspension;
washing the chloroplast suspension; and
conditioning the washed chloroplast suspension to obtain the dry chloroplast composition,
wherein at least 75% of the chloroplasts comprised in the composition are intact e.g. as determined by dynamic light scattering measurement and analysis, and
optionally wherein the washed chloroplast suspension and/or the dry chloroplast composition comprise about 90% of the Rubisco content in the chloroplast suspension and wherein said liquid chloroplast composition has at least one ratio chosen from:
a ratio of chlorophyll/FBPP of about 50 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{\text{FBPP in (intensity/mg powder)}} \times 10000000,$$

the FBPP intensity being measured by immunoblot,
a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000,$$

and
a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right) \times 100.$$

Another aspect relates to a dry chloroplast composition, obtained according to a process herein described.

Another aspect relates to isolated Fabaceae family plant microfibers, having an average length of about 40 microns to about 200 microns.

Another aspect relates to isolated *Medicago* spp plant microfibers, having an average length of about 40 microns to about 200 microns and having a decrease in saponin content of about 20% to about 95%, about 20% to about 30%, about 70% to about 95%, about 70% to about 90%, about 70% to 80%, about 80% to about 90%, about 90% to about 95%, or more than 90% relative to a reference *Medicago* spp plant.

Another aspect relates to isolated *Medicago* spp plant microfibers, having an average length of about 40 microns to about 200 microns and having decrease in medicagenic acid saponin content of about 0.3 mg/g to about 2.4 mg/g (dry basis) relative to a reference *Medicago* spp plant.

Another aspect relates to isolated *Medicago* spp plant microfibers, having an average length of about 40 microns to about 200 microns and having a medicagenic acid saponin content of about 1.0 to about 6.4 mg/g (dry basis), wherein at least 75% of chloroplasts comprised in the microfibers are intact e.g. as determined by dynamic light scattering measurement and analysis.

Another aspect relates to a plant microfiber composition comprising Fabaceae family plant microfibers and water, the plant microfibers having an average length of about 40 microns to about 200 microns.

Another aspect relates to a plant microfiber composition comprising *Medicago* spp plant microfibers having an average length of about 40 microns to about 200 microns, the composition having a decrease in medicagenic acid saponin content of about 20% to about 95%, about 20% to about 30%, about 70% to about 95%, about 70% to about 90%, about 70% to 80%, about 80% to about 90%, about 90% to about 95%, or more than 90% relative to a reference *Medicago* spp plant.

Another aspect relates to a plant microfiber composition comprising *Medicago* spp plant microfibers having an average length of about 40 microns to about 200 microns, the composition having a decrease in medicagenic acid saponin content of about 0.3 mg/g to about 2.4 mg/g (dry basis) relative to a reference *Medicago* spp plant.

Another aspect relates to a plant microfiber composition comprising *Medicago* spp plant microfibers having an average length of about 40 microns to about 200 microns, the composition having a medicagenic acid saponin content of about 1.0 to about 6.4 mg/g (dry basis), wherein at least 75% of the chloroplasts comprised in the composition are intact e.g. as determined by dynamic light scattering measurement and analysis.

Another aspect relates to a use of the plant microfibers disclosed herein, in the manufacture of food and feed products.

Another aspect relates to a use of the plant microfibers disclosed herein, in the manufacture of a cosmetic product.

Another aspect relates to a use of the plant microfibers disclosed herein as a human and/or animal nutritional supplement.

In yet another aspect, there is provided a process for preparing a Fabaceae family plant microfiber composition, said process comprising:
- providing Fabaceae family plant fragments;
- separating a macrofiber depleted suspension from the plant fragments;
- separating a microfiber fraction comprising plant microfibers from the macrofiber depleted suspension; and
- conditioning the microfiber fraction to obtain the microfiber composition.

In yet another aspect, there is provided a process for extracting at least one compound from Fabaceae family plant microfibers, said process comprising:
- providing Fabaceae family plant fragments;
- separating a macrofiber depleted suspension from the plant fragments;
- separating a microfiber fraction comprising plant microfibers from the macrofiber depleted suspension;
- obtaining a microfiber fraction comprising the plant microfibers; and
- extracting from the plant macrofibers the at least one compound, optionally chosen from proteins, enzymes, peptides, amino acids, fatty acids, fatty alcohols, terpenes, phenols, pigments and mixtures thereof.

Another aspect relates to a use of a microfiber fraction comprising plant microfibers for extracting at least one compound chosen from proteins, enzymes, peptides, amino acids, fatty acids, fatty alcohols, terpenes, phenols, pigments and mixtures thereof.

Another aspect relates to isolated Fabaceae family plant microfibers obtained according to the process herein disclosed.

Another aspect relates to a Fabaceae family plant microfiber composition obtained according to the process herein disclosed.

BRIEF DESCRIPTION OF THE DRAWINGS

In the following drawings, which represent by way of non-limitative examples, various embodiments of the disclosure, wherein n.

DETAILED DESCRIPTION

Figure 1:
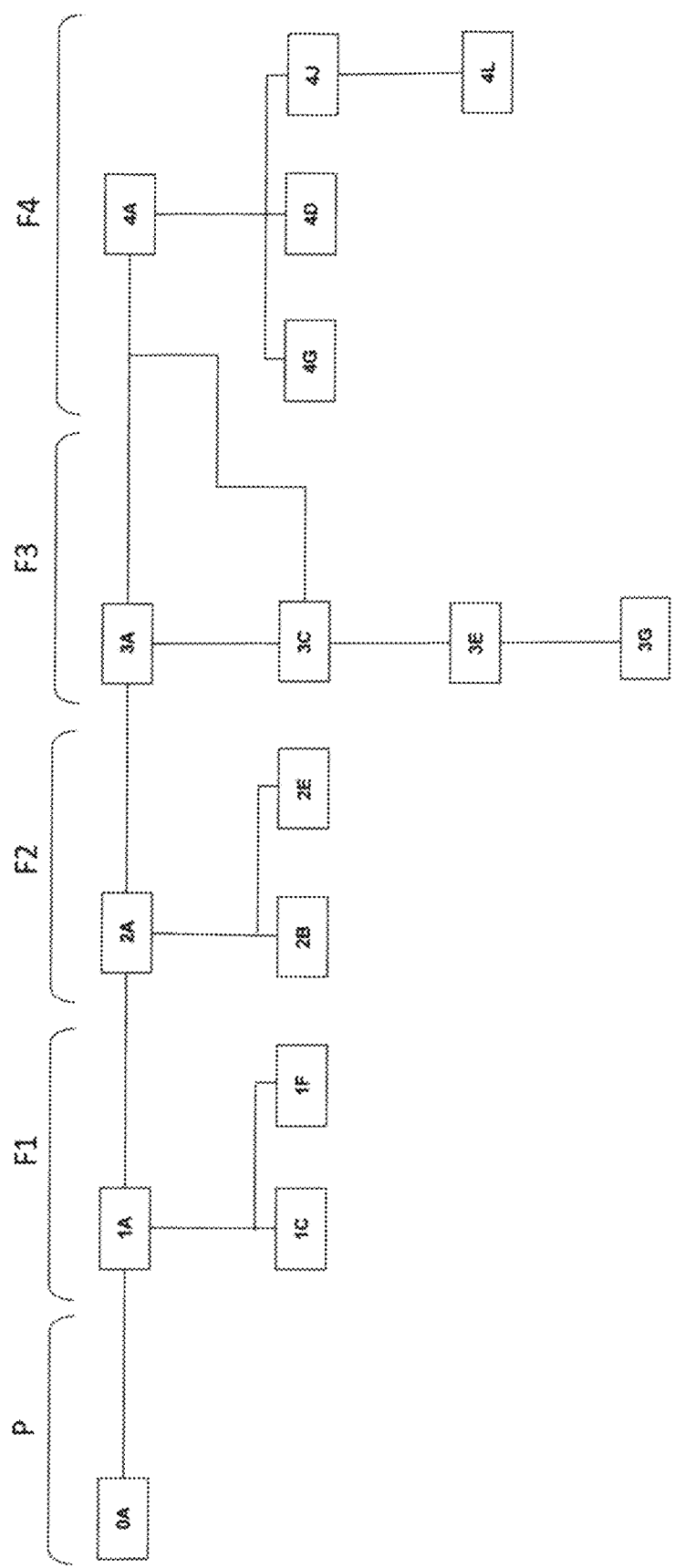
FIG. 1 is a flow sheet diagram of the process herein disclosed according to one embodiment.

Further features and advantages of the disclosure will become more readily apparent from the following description of various embodiments as illustrated by way of examples only and in a non-limitative manner.

As used herein, the term "fibers" means elongate structures composed mainly of cellulose, hemicellulose, and lignin. The level of lignification varies, in particular, according to the plant, the structure of the plant and its growth stage. The fibers play a role in providing support to the plant. They may be isolated or in bundles and be of various length and diameter. As used herein, the term "fibers" (macrofibers and microfibers) refers not only to such elongate structures but also to other structures or aggregates that may be more or less retained by whole or fragmented filiform structures. Depending on the context, more or less bound liquid containing more or less dissolved compounds or molecules may also be found. It should be noted that in this document the term macrofiber may include fibres of any size resulting from a pressing separation activity, for example, while the term microfibre refers mainly to fibres of small size, for example less than 200 microns, resulting from screening separation, for example.

As used herein the terms "plant fragment" or "plant fragments" mean portions or sections of varying lengths of Fabaceae family plant, for example of alfalfa plant, including aerial portions, e.g. stem and leaf portions, preferably more leafy portions of the plants. For example, the plant fragments have a leaf to stem ratio of about 1:1, about 1:1.1, about 1:1.2, about 1:1.3, about 1:1.4 or about 1:1.5 (based on wet weight). For example, the plant fragments contain at least 70% of the chloroplast content in the plant.

As used herein, the term "reference Fabaceae family plant" means a Fabaceae family plant, preferably aerial portions thereof, that has not been processed, pressed, extracted, or otherwise treated or transformed. The reference Fabaceae family plant may, for example, be an unharvested Fabaceae family plant or a Fabaceae family plant that has been cut into smaller fragments. For example, the reference Fabaceae family plant may be the plant fragments 0B harvested prior to processing as described herein (e.g. prior to separating, conditioning, extracting, washing). It will be understood that the reference Fabaceae plant is of the same family, tribe (e.g. Trifolieae), genus, species (e.g. *Medicago sativa*), subspecies (e.g. *Medicago sativa* subsp. *Sativa*) and variety (or cultivar) as the plant to which it is being compared to. For example, if the plant fragments are obtained from a specific alfalfa cultivar, the reference Fabaceae family plant comprises fragments of the same alfalfa cultivar. Similarly, the term "reference *Medicago* spp plant" means a *Medicago* spp plant, preferably aerial portions thereof, that has not been processed, pressed, extracted, or otherwise treated or transformed. The reference *Medicago* spp plant may, for example, be an unharvested *Medicago* spp plant or a *Medicago* spp plant that has been cut into smaller fragments. For example, the reference *Medicago* spp plant may be plant fragments 0B harvested prior to processing as described herein. For example, if the fragments are obtained from a specific alfalfa cultivar, the reference *Medicago* spp plant is of the same alfalfa cultivar. In the context of measuring and comparing the content of a compound e.g. saponin or Rubisco present in the plant to be tested, the reference may also be a known value.

As used herein, the term "saponin" or "saponins" refers to an aglycone or sapogenin unit linked to one or more carbohydrate chains. The aglycone or sapogenin unit consists of either a sterol or the more common triterpene unit. In both the steroid and triterpenoid saponins, the carbohydrate sidechain is usually attached to the 3 carbon of the sapogenin. Saponins possess surface-active or detergent properties because the carbohydrate portion of the molecule is water-soluble, whereas the sapogenin is fat-soluble. Some plant saponins have been shown to inhibit cholesterol absorption from the intestinal lumen in experimental animals and consequently to reduce the concentration of plasma cholesterol. Other saponins have also been shown to have insecticidal properties.

As used herein, the term "medicagenic acid" or "medicagenic acid saponin" means a specific form of saponin obtained from *Medicago* spp, e.g. more particularly from *Medicago sativa* (alfalfa). Medicagenic acid is one of the most abundant saponins found in alfalfa foliage, representing about 50% of total saponin content, depending on the cultivar. It will be understood that saponin content, including medicagenic acid saponin content, may vary in absolute value depending, for example, on the cultivar type. In contrast, the relative concentration of saponin or medicagenic acid saponin (e.g. in terms of decrease in concentration relative to a reference *Medicago* spp plant) from one product to another, resulting from the fractionation process, remains similar regardless of cultivar type. For example, saponin content can be determined using mass spectrometry analysis on a UPLC-MS/MS system e.g. in electrospray mode. For example, quantification of saponin content can be based on commercial standards, for example of medicagenic acid (LGC standard), bayogenin (Cederlane), hederagenin (Sigma Aldrich Canada Ltd) soyasapogenol A (LGC standard) and soyasapogenol B (Sigma Aldrich Canada Ltd).

As used herein, the term "chloroplast content" means the total chloroplast content in a composition, suspension or mixture herein described. The chloroplast content may be determined qualitatively or quantitatively, using any suitable known method, for example using light scattering techniques, using visual inspection under microscopy, spectrophotometric methods for analyzing specific chloroplast pigments (e.g. carotene, xanthophyll, chlorophyll), measuring photosynthesis levels of the chloroplasts (e.g. carbon assimilation and/or oxygen evolution/emission) and measuring levels of proteins, enzymes and/or other molecules solely found in chloroplasts, e.g. immunofluorescent quantitation of Rubisco holoenzyme, specific inner or outer chloroplast membrane proteins or thykaloid lumen or thykaloid membrane proteins. The chloroplast content may be measured in terms of chlorophyll content, for example according to the Official Methods of Analysis of AOAC INTERNATIONAL (2005) 18th Ed., AOAC Official Method 942.04 (Modified). The beta carotene content may be measured for example according to the Official Methods of Analysis, Method 2005.07, AOAC INTERNATIONAL, (modified).

As used herein, the term "solid fraction" means a mixture of structures, compounds and/or molecules, extracted from plant biomass, that is not soluble and that may retain a certain volume of liquid, and/or that is totally or partially bounded to said liquid.

As used herein, the term "liquid fraction" means a liquid extracted from plant biomass, modified or not (e.g. by addition of an acid), that may contain structures and/or compounds in suspension and/or molecules dissolved or not in said liquid.

As used herein, the term "protein content" means the total protein content of a product (e.g. composition, precursor or suspension) herein described. The protein content includes the Rubisco protein content. The protein content includes proteins that are linked or connected to or embedded in plant structures (e.g. membranes), proteins that are wholly soluble, proteins that are naturally present as aggregates in suspension in the liquid fraction, and portions of these proteins that are either partially assembled or partially degraded. The protein content can be measured using recognized methods in the art, for example without limitation protein assays e.g. bicinchoninic acid (BCA) protein assay. The protein content may also be measured according to the Dumas Method or according to the Official Methods of Analysis of AOAC INTERNATIONAL, 18th Ed., Methods 968.06 and 992.15, AOAC INTERNATIONAL, Gaithersburg, MD, USA, (2005) (Modified).

As used herein, the term "lipid content" means the total lipid content of a product (e.g. composition, precursor or suspension) herein described. The lipid content includes triglycerides, phospholipids (including the valuable omega-3 and omega-6 fatty acids) sphingolipids and other membrane lipids and lipid droplets (mainly triacylglycerols). The lipid content can be measured using recognized methods in the art. For example, the fatty acid profile may be measured according to Official Method No. 996.06 of the Official Methods of Analysis of the AOAC INTERNATIONAL (modified), 19th Ed., AOAC INTERNATIONAL: Gaithersburg, Maryland (2012).

As used herein, the term "depleted" means a suspension that is free of such element, or contains less than about 20%, less than about 15%, less than about 10%, less than about 5% or less than about 1% of such element. For example, with reference to the macrofiber depleted suspension 1H, "depleted" means at least an 80% reduction in such macrofibers compared to the plant fragments 0B. Similarly, with reference to the microfiber depleted suspension 2G, "depleted" means at least a 80% reduction in such microfibers compared to the macrofiber depleted suspension 1H. The same reasoning applies to the macrofiber depleted suspension 1H.2 and the microfiber-depleted suspension 2G.2.

As used herein, the term "chloroplast reduced" means a suspension from which at least 50% of the initial chloroplasts have been removed during the process described herein.

As used herein, the term "saponin-enriched powder" means a saponin-containing powder having at least a 5 fold, 10 fold, 15 fold, 20 fold, 25 fold, 30 fold, 40 fold, or 50 fold increase in saponin content compared to the saponin content of a reference Fabaceae family plant in powder form.

As used herein, the term "conditioning" or "conditioned" means any process, or treatment that may be carried out on an intermediate product in view of making an end product suitable for further (e.g. commercial, industrial) use. For example, conditioning comprises minimally packaging a product and optionally further drying, diluting, adding additives and/or supplements. For example, in the context of the microfiber fraction, the conditioning may include in addition to packaging, drying the microfibers to reduce their moisture content and adding a suitable amount of nutritional supplement and other additives.

As used herein, the singular forms "a", "an" and "the" include plural references unless the content clearly dictates otherwise. It should also be noted that the term "or" is generally employed in its sense including "and/or" unless the content clearly dictates otherwise.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms "including", "having" and their derivatives.

Terms of degree such as "substantially", "about" and "approximately" as used herein mean a reasonable amount of deviation of the modified term such that the end result is not significantly changed. These terms of degree should be construed as including a deviation of ±5% or ±10% of the modified term if this deviation would not negate the meaning of the word it modifies.

The definitions and embodiments described in particular sections are intended to be applicable to other embodiments herein described for which they are suitable as would be understood by a person skilled in the art.

The presently disclosed fractionation process has been developed based on the principle of preservation of integrity and quality of the main components of each plant fragments which can generate various end and intermediary products as well as precursors e.g. molecules and compounds presenting a high value for the development of other products following their extraction and purification, if required. It was hypothesized that preserving the integrity of chloroplasts (i.e. major component of leaf cells) would allow to isolate them from the rest of the plant content and preserve the quality of their own components (e.g. Rubisco, membrane lipids, membrane proteins, carotenes, xanthophyll, chlorophyll). Preservation of chloroplast integrity has allowed to separate chloroplast components into one single fraction, and further to wash and condition this fraction in different end products using various methods. Thus, from this chloroplasts-based fraction, it is possible to condition liquid and dry products with high chloroplasts concentration. It is also possible to extract, or release, Rubisco from the non-soluble chloroplast components (e.g. membrane lipids, membrane proteins, membrane bound pigments) and to purify it at the required level, based on the size of Rubisco protein bodies, to produce Rubisco compounds or Rubisco based active ingredients. Furthermore, it was observed that the confinement of the chloroplast components in their original particle form in the one single fraction allowed preservation of chloroplasts as well as valuable essential components in other fractions. The macrofiber fraction contains mainly digestible macrofibers of the plant fragments, suitable for animal nutrition, since an important quantity of saponin was extracted from this solid fraction. The microfiber fraction contains microfibers also beneficial for humans and animals. In addition, these two fractions also contain various value-added molecules or compounds such as fatty alcohols, enzymes, peptides, etc. The remaining fraction is liquid and presents a high saponin concentration which can be extracted and purified in order to develop different saponin-based end products. By preserving chloroplast integrity, it was possible to produce a liquid fraction devoid of major contaminating components of the chloroplast that would otherwise have been released as solubles in the liquid fraction, and impair further treatment of the liquid fraction aimed at isolating valuable soluble compounds.

Figure 2A:
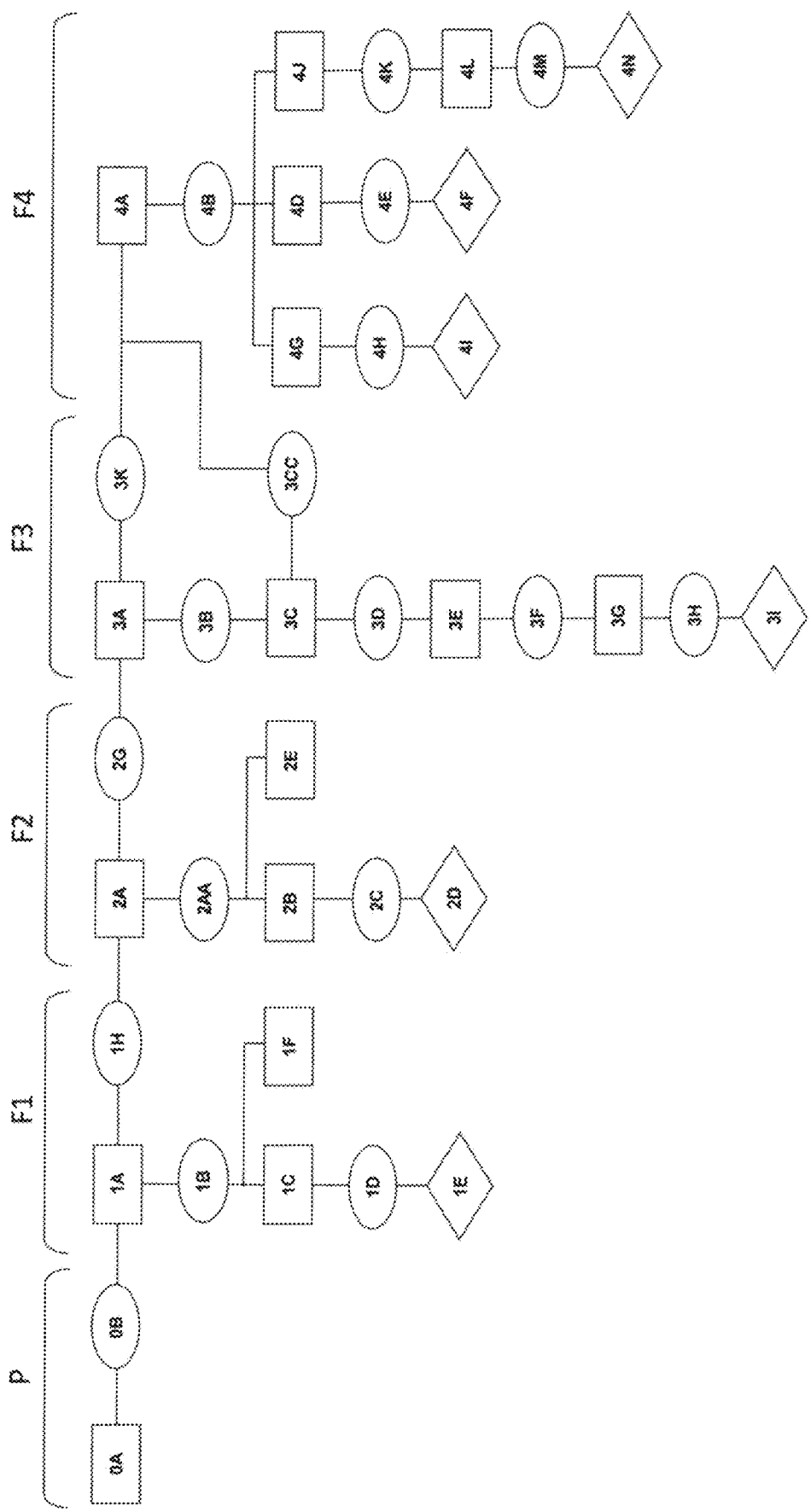
FIG. 2A is a flow sheet diagram of the process herein disclosed according to another embodiment.

The global process is shown in the flow sheet diagram of FIG. 1 and more specifically detailed in the flow sheet diagram of FIG. 2A. Briefly, suitable plants, e.g. alfalfa, are produced and fragmented during biomass preparation 0A and undergo a macrofiber separation 1A in which a liquid fraction is separated from the plant fragments 0B. The resulting macrofiber fraction 1B can be subject to a macrofiber conditioning 1C to obtain a macrofiber composition 1D ready to use as end products and/or to undergo a compound extraction 1F of high value molecules and/or compounds. During microfiber depletion 2A, remaining microfibers are extracted from the liquid fraction i.e. macrofiber depleted suspension 1H, and are subject to a microfiber conditioning 2B to produce a microfiber composition 2C. The microfiber composition 2C is ready to be used as end product for human and animal nutrition 2D. Similar to the macrofiber fraction 1B, the microfiber fraction 2AA may also undergo a compound extraction 2E of high value molecules and/or compounds. The resulting microfiber depleted suspension 2G is subject to a chloroplast separation 3A to remove chloroplasts from the suspension which generates two different suspensions, the chloroplast suspension 3K and the chloroplast reduced suspension 3B. The latter is subject to a suspension clarification 3C to remove remaining proteins, undesirable solubles (e.g. causing off-odor and off-taste) as well as other suspended matters (e.g. 3CC) and can be subject to a compound extraction 3E to extract molecules and compounds, such as saponin. Afterwards, the resulting saponin-enriched powder 3F is obtained and may for example undergo a saponin powder conditioning 3G. The chloroplast suspension 3K undergoes a chloroplast washing 4A followed by a liquid chloroplast conditioning 4G and/or a dry chloroplast conditioning 4D, to obtain a liquid chloroplast composition 4H and/or a dry chloroplast composition 4E, ready to use as end products 4I and 4F, respectively. It should be noted that a compound extraction 4J can be also carried out instead of conditionings 4G and 4D, in whole or in part, to extract Rubisco and/or other molecules and compounds. The resulting Rubisco suspension 4K can undergo a Rubisco conditioning 4L obtain a Rubisco precursor 4M which can be used for further end product development 4N.

Other specific but non-limiting examples will follow. In the flow sheet diagrams of FIGS. 1 to 10B, process activities are identified by rectangles, products (intermediate, precursor, end products) are identified by ovals, and uses of the precursor products and end products are identified by diamonds.

Plant Production P

As shown for example in in FIG. 2A, the plant production P begins with the biomass preparation 0A which comprises cultivating, harvesting and fragmenting plants and which results in fresh plant fragments 0B. This preliminary plant production P is also shown in FIGS. 1, 2B, 3, 4, 5, 6, 7, 8 and 9.

Care is taken during the biomass preparation 0A so that the aerial portion of the plant does not become too lignified. In fact, it is desirable to select biomass (e.g. plant) that contains a desirable leaf to stem ratio. The plants are preferably harvested at a stage where the lower part of the stem has not started to shed leaves and where the stem still shows signs of photosynthesis (green). For example, for alfalfa, this stage is at about 50 cm in height, but can vary significantly between cultivars, weather conditions, soil type, soil density, stand density etc. Regardless of the cultivar, it is desirable that harvest be performed before flowering. Similarly, for other plants species, for example forage grasses, harvest is preferably conducted prior to inflorescence. The general objective is to feed the process with leafy biomass that has a low content in lignified fiber, as such fiber may create excessive shearing during macrofiber separation 1A and microfiber depletion 2A.

Biomass harvest is best performed with a harvester, for example equipped with a cutter bar. As a general principle, harvesters equipped with conditioning devices and/or hammer mills are to be avoided. The objective is to feed the process with plant fragments 0B that have been cut sharply with as little shearing, milling and stripping as possible, in order to minimize releasing of cell content at this early stage of the process. Releasing cell content at this stage would have two effects deleterious to the process principle of preserving integrity. Releasing chloroplasts at this stage would expose them to breakage during plant fragment 0B manipulation and transport. In the same way, releasing cell content at this stage would trigger premature denaturation of valuable components. Examples of denaturation could be, for example, chemical (e.g. oxidation), enzymatic (e.g. proteolysis) or biological (e.g. microbial growth stimulated by release of high energy components). As a precaution, an antioxidant, for example, sodium metabisulfite, may be added to the freshly harvested biomass (e.g. by spraying) to control/reduce oxidation.

It will be understood that while it is preferred to obtain freshly harvested and cut plant fragments 0A, it is not necessary that the process be carried out starting with the biomass preparation 0A and the resulting intermediary product or plant fragments 0B. Other suitable plant fragments or green biomass may be used so long as they have recently (e.g. less than a day) been harvested and cut with as little damage to the chloroplast integrity as possible.

For example, the plant fragments 0B are obtained by cutting at least one plant into fragments. For example, the plant fragments 0B are obtained by using a cutter bar.

For example, the plant fragments 0B have an average length of about 10 mm to about 100 mm. For example, the plant fragments 0B have an average length of about 15 mm to about 85 mm. For example, the plant fragments 0B have an average length of about 20 mm to about 50 mm. For example, the at least one plant is cut prior to inflorescence.

For example, the at least one plant is a Fabaceae family plant. For example, the at least one plant is a plant from the Trifolieae tribe. For example, the at least one plant is from the *Medicago* genus such as *Medicago sativa, Medicago falcata, Medicago polymorpha, Medicago lupulina, Medicago rugosa, Medicago cretacea, Medicago platycarpa, Medicago marina, Medicago rupestris, Medicago secundiflora* or *Medicago truncatula*. For example, the at least one plant is the *Medicago sativa* species or alfalfa. It will be understood that reference herein to *Medicago sativa* includes all subspecies (ssp. or subsp.) of *Medicago sativa* (i.e. *Medicago sativa* ssp). For example, when the at least one plant is *Medicago sativa*, it will be understood that any suitable cultivar or variety may be used, including for example the Symphonie cultivar.

As mentioned herein the total saponin concentration in the plant may vary based on several factors such as tissue type and stage of plant grown. The total saponin concentration also varies from one cultivar to another. For example, some *Medicago sativa* cultivars have a lower content of medicagenic acid saponin e.g. 1.5 mg/g (dry basis) while other *Medicago sativa* cultivars contain a higher content of medicagenic acid saponin e.g. 8 mg/g (dry basis). For example, as described in Example 13 herein, the aerial portions of the Symphonie cultivar has a medicagenic acid content of 3.3 mg/g (dry basis).

For example, the alfalfa plant is cut at a height of about 40 cm to about 60 cm. For example, the alfalfa is cut at a height of about 45 cm to about 55 cm. For example, the alfalfa is cut at a height of about 50 cm.

For example, the plant fragments 0B have an average leaf to stem ratio of about 1:1, of about 1:1.2, of about 1:1.3, of about 1:1.4, of about 1:1.5 (based on wet weight).

For example, the plant fragments 0B are treated with an antioxidant and/or an antimicrobial agent. For example, the antioxidant is citric acid, metabisulfite, optionally sodium metabisulfite or potassium metabisulfite. For example, the antimicrobial agent is citric acid, benzoate, optionally sodium benzoate or potassium benzoate.

For example, the plant fragments 0B are contacted with the antioxidant and/or the antimicrobial agent within 2 hours of harvesting. For example, the plant fragments 0B are contacted with the antioxidant and/or the antimicrobial agent within 1 hour of harvesting. For example, the plant fragments 0B are contacted with the antioxidant and/or the antimicrobial agent within 15 minutes of harvesting. For example, the plant fragments 0B are contacted with the antioxidant and/or the antimicrobial agent within 5 minutes of harvesting. For example, the plant fragments 0B are contacted with the antioxidant and/or the antimicrobial agent at time of harvesting.

First Fractionation F1

Figure 2B:
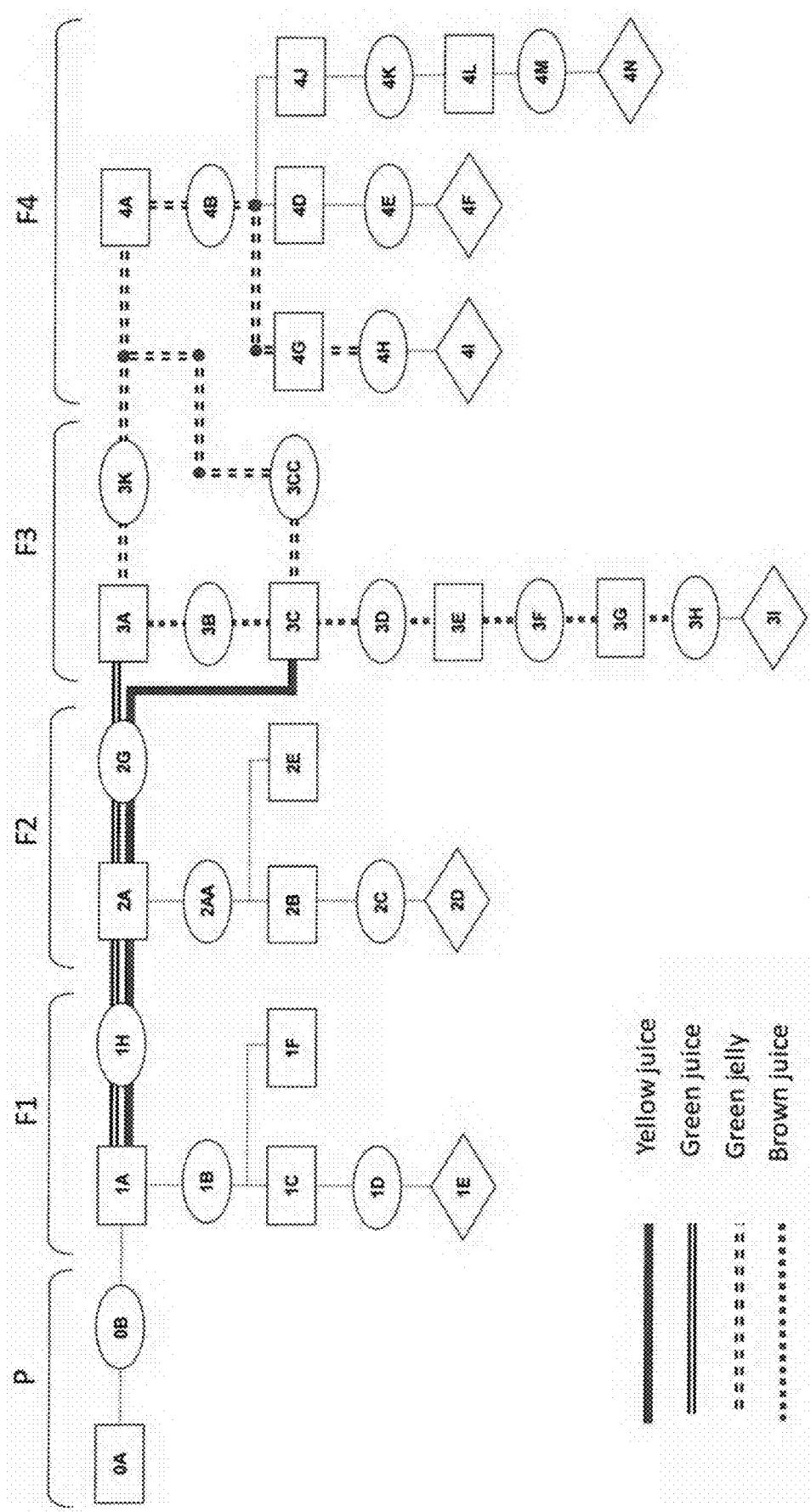
FIG. 2B is a flow sheet diagram of the process according to FIG. 2A, with reference made to operationally used terms, wherein the bold lines refer to the yellow juice; the double lines refer to the green juice; the double stippled lines refer to the green jelly; and the dotted lines refer to the brown juice.
Figure 3:
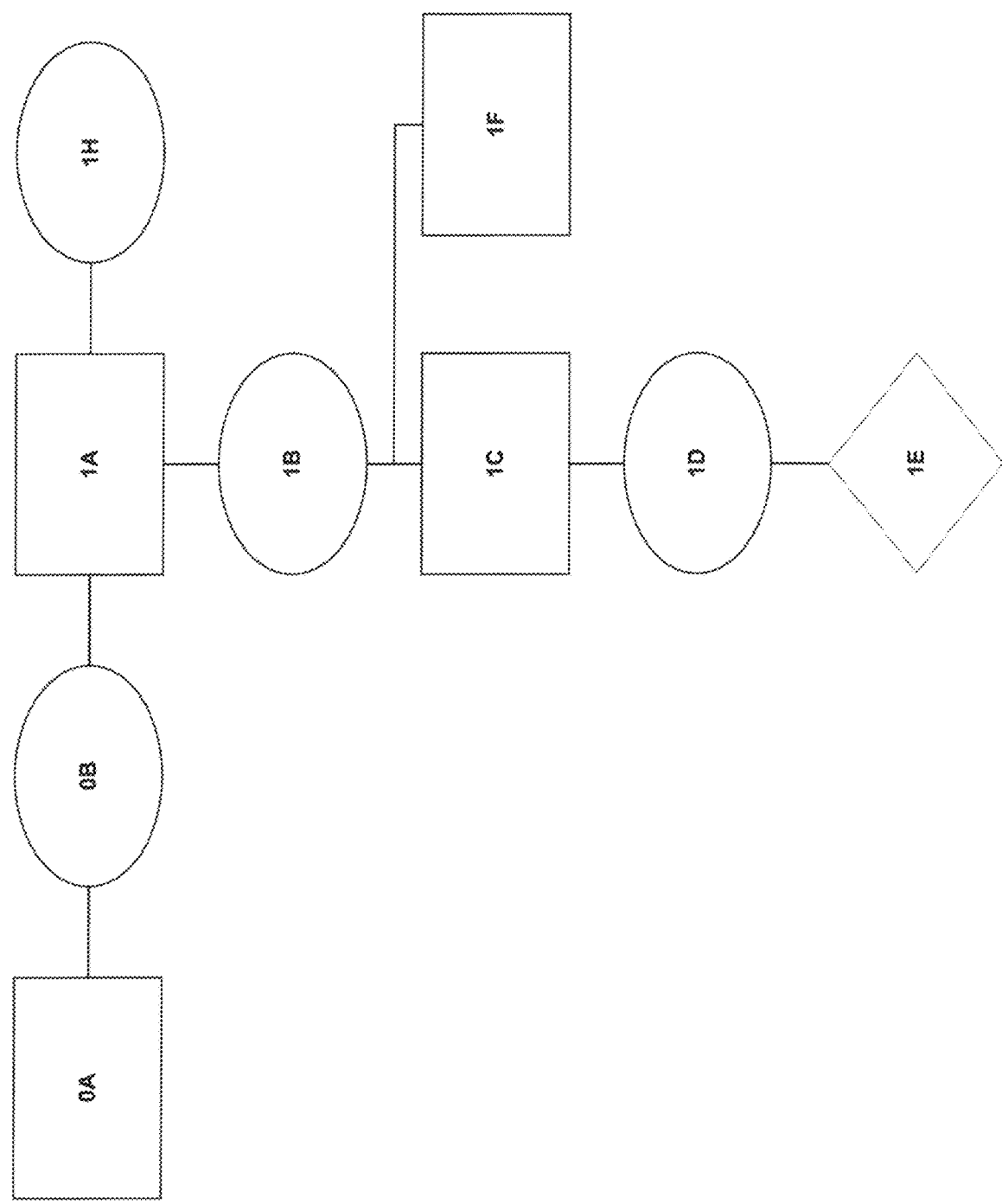
FIG. 3 is a flow sheet diagram detailing the first fractionation F1 and in particular a process of obtaining a macrofiber composition from harvested plants, according to another embodiment.
Figure 4:
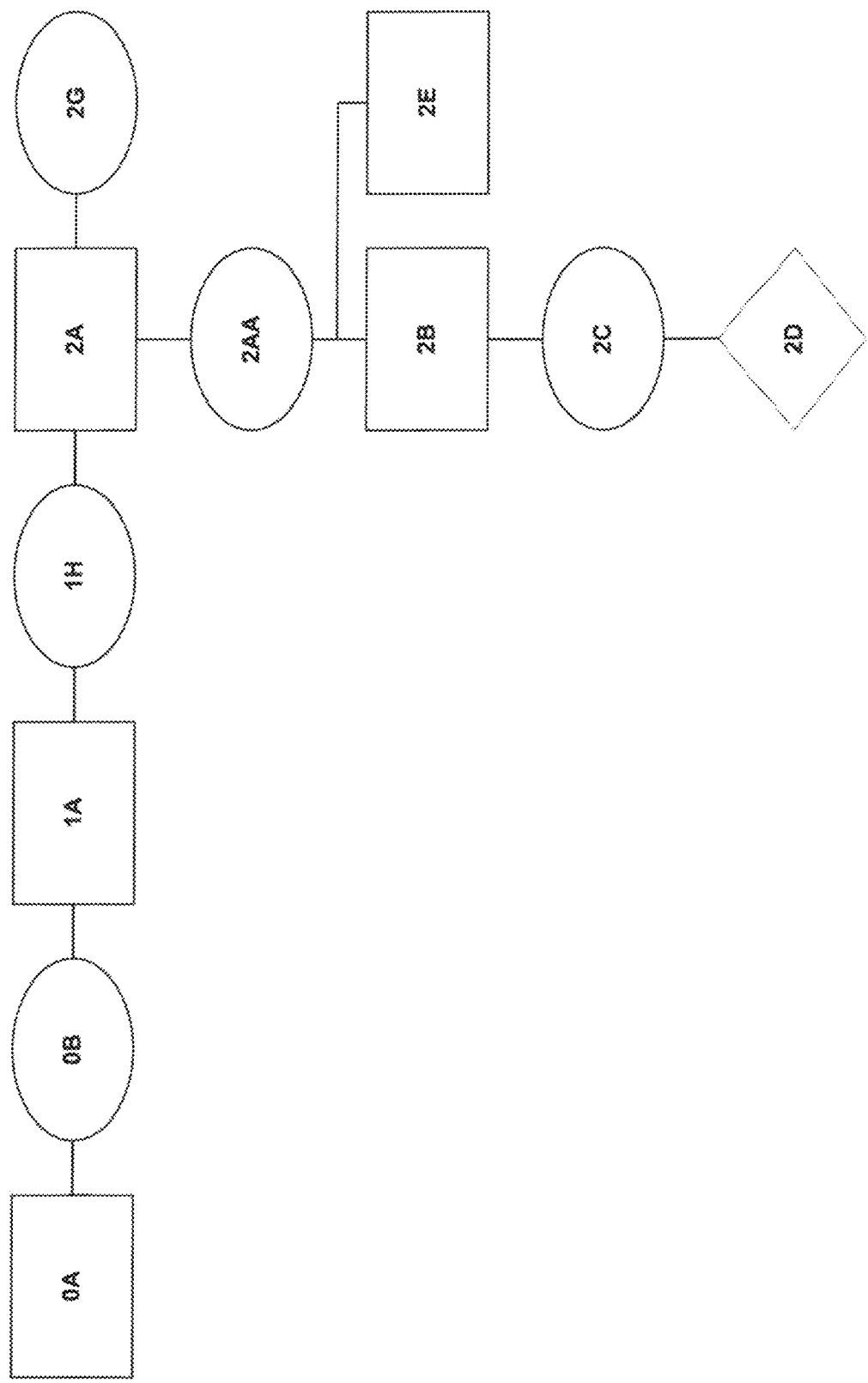
FIG. 4 is a flow sheet diagram detailing the second fractionation F2 and in particular a process of obtaining microfiber composition from harvested plants, according to another embodiment.
Figure 5:
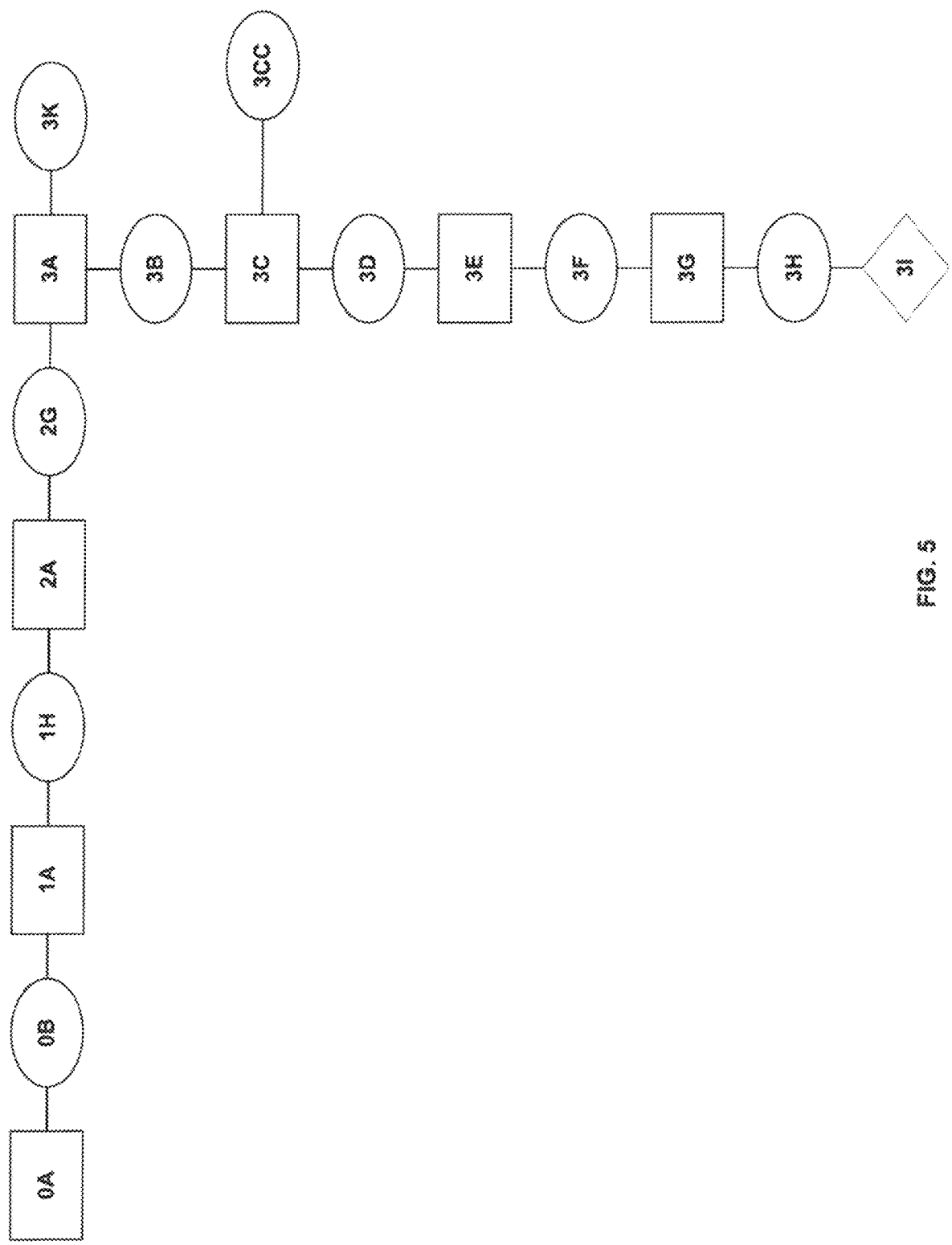
FIG. 5 is a flow sheet diagram detailing the third fractionation F3 and in particular a process of obtaining a saponin precursor from harvested plants, according to another embodiment.
Figure 6:
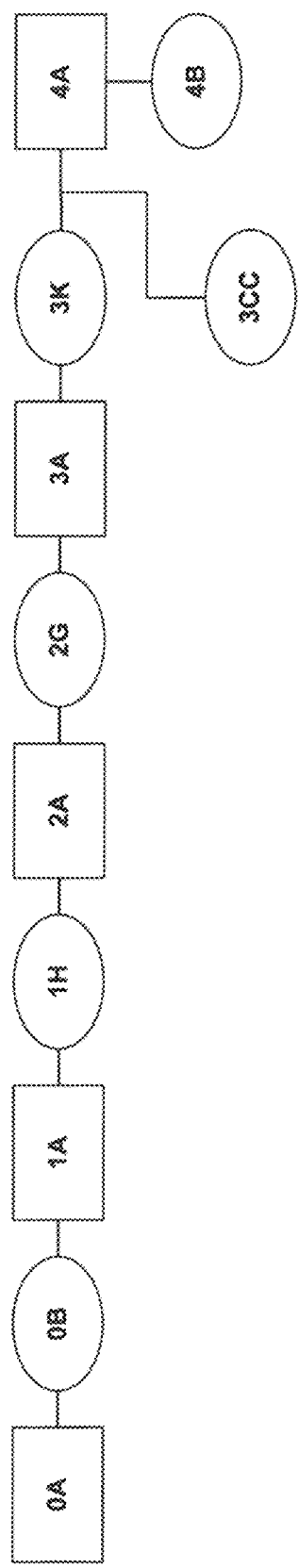
FIG. 6 is a flow sheet diagram detailing the fourth fractionation F4 and in particular a process of obtaining a washed chloroplast suspension from harvested plants, according to another embodiment.
Figure 7:
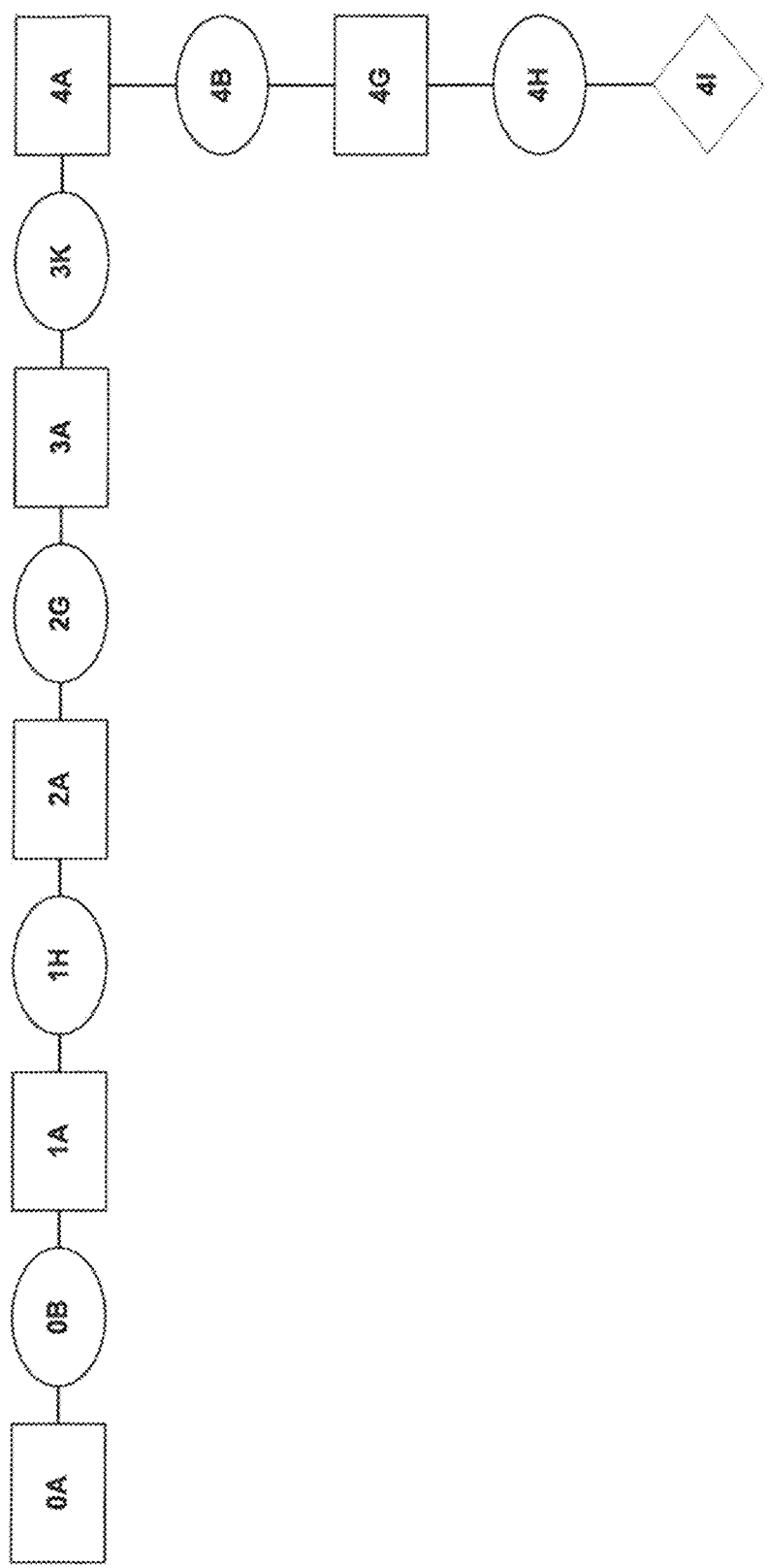
FIG. 7 is a flow sheet diagram detailing the fourth fractionation F4 and in particular a process of obtaining a liquid chloroplast composition from harvested plants, according to another embodiment.
Figure 8:
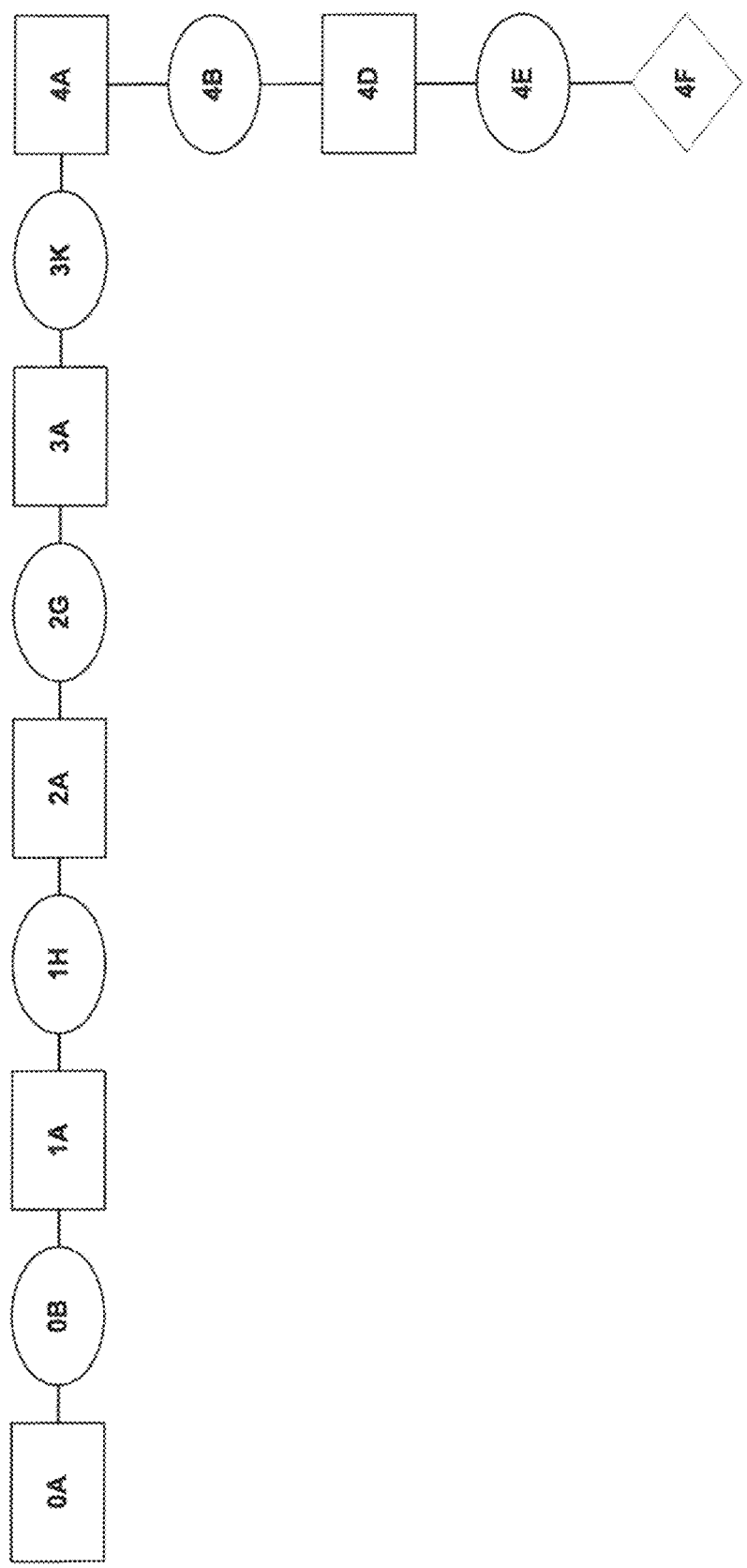
FIG. 8 is a flow sheet diagram detailing the fourth fractionation F4 and in particular a process of obtaining a dry chloroplast composition from harvested plants, according to another embodiment.
Figure 9:
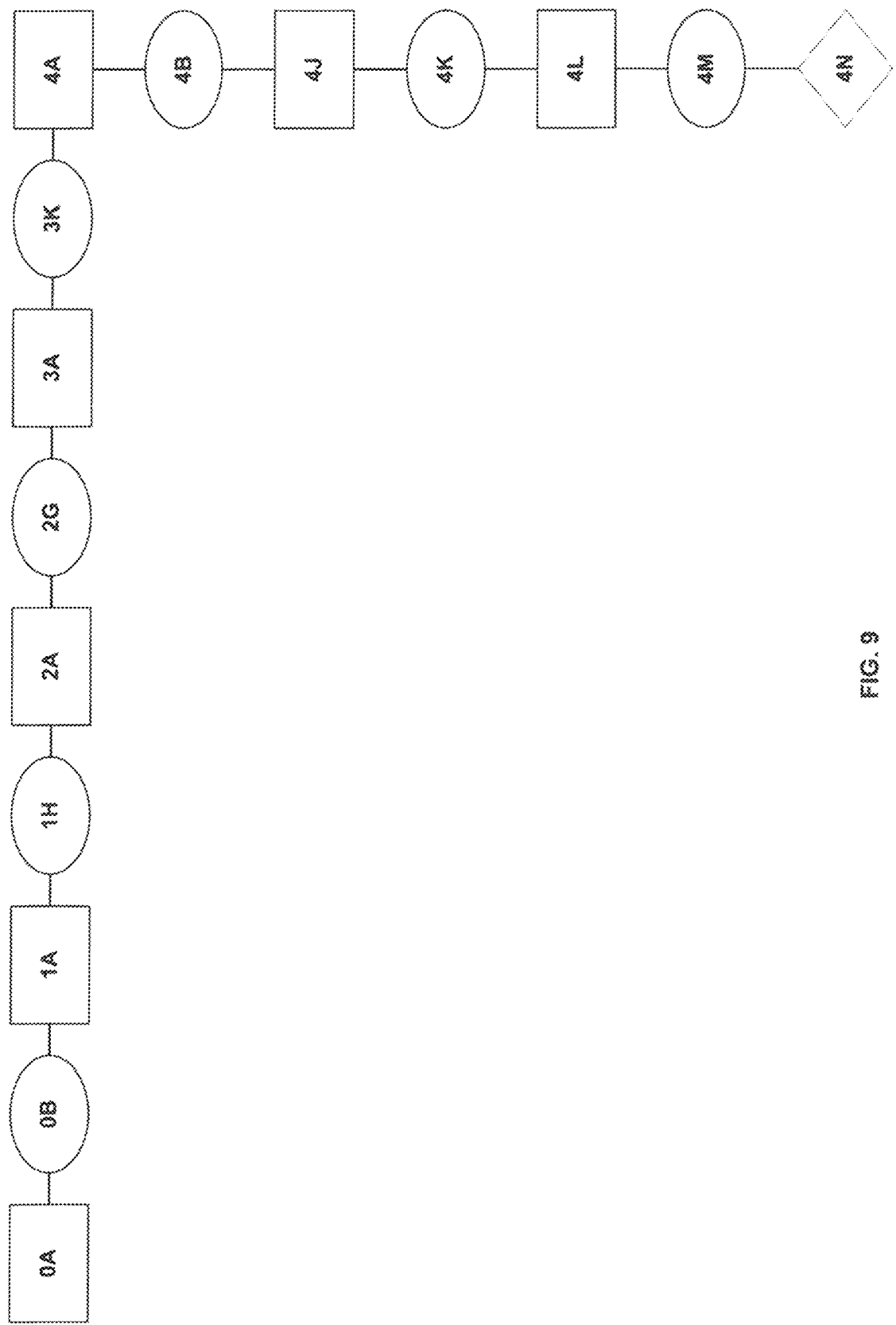
FIG. 9 is a flow sheet diagram detailing the fourth fractionation F4 and in particular a process of obtaining a Rubisco precursor from harvested plants, according to another embodiment.

Referring to FIGS. 2A, 2B and 3, the first fractionation F1 is represented by process activities (rectangle), intermediary or end products (oval) and uses (diamond) from 1A through 1H. The objective of the first fractionation is to separate as much as possible of the liquid fraction from the plant fragments 0B. Upon providing plant fragments 0B (e.g.

fresh plant fragments as described for example above), such fragments are submitted to a macrofiber separation 1A to obtain a macrofiber fraction 1B as well as an extracted macrofiber depleted suspension 1H, which contains inter alia chloroplasts and remaining microfibers. The macrofiber separation 1A can be carried out more than once to extract more valuable molecules, compounds or structures from the macrofiber fraction 1B in the resulting additional suspensions. The resulting macrofiber fraction 1B undergoes a macrofiber conditioning 1C to obtain a macrofiber composition 1D which can be used for animal nutrition 1E.

Macrofiber Separation 1A

It is preferable that the macrofiber separation 1A be performed while avoiding excessive shearing, temperature increases and/or pressure differentials, all conditions that would lead to chloroplast breakage. It is desirable that the separation be carried out quickly as possible after providing the plant fragments 0B, and the temperature not exceed for example 30° C. at the output of the separation device used. The device is suitable for separation as long as the mechanical forces used, or the energy dissipated, preserve chloroplast integrity. Hammer mills and ultrasonic devices are preferably to be avoided as they may create excessive shearing and/or destroy chloroplast membrane integrity. The presently disclosed process is in contrast with other known fractionation processes for photosynthetically active plant biomass wherein the use of excessive mechanical strength results in breakage of chloroplast integrity and release of Rubisco protein component, for example, in the liquid fraction and thus reducing quality of the chloroplast concentrates. Rubisco would then be mixed with all remaining soluble component of the plant cell and its recovery or purification would also become challenging. In addition, use of mechanical conditions that would result in high shearing at this early stage will likely increase biomass temperature, which in turn would result in increased oxidative decay of major nutritional solutes present in the fibrous fractions (macrofiber and microfiber), in the chloroplasts and in the liquid phase, such as for example carotenes, chlorophyll, natural antioxidants (i.e. not antioxidants added to the fractions), anthocyanins, proteins and omega-3 phospholipids, which are all heat labile and pH sensitive.

For example, the separating of the macrofiber depleted suspension 1H is carried out at a temperature of about 42° C. or less. For example, the of separating the macrofiber depleted suspension 1H is carried out at a temperature of about 4° C. to about 42° C. For example, the separating of the macrofiber depleted suspension 1H is carried out at a temperature of about 15° C. to about 38° C. For example, the separating of the macrofiber depleted suspension 1H is carried out at a temperature of about 20° C. to about 34° C. For example, the separating of the macrofiber depleted suspension 1H is carried out at a temperature of about 25° C. to about 34° C.

For example, the separating of the macrofiber depleted suspension 1H is carried out using a press, optionally a screw press or a hydraulic press. For example, the pressure applied is less than about 800 kPa. For example, the pressure applied is about 400 kPa to about 800 kPa. For example, the pressure applied is about 400 kPa to about 750 kPa. For example, the pressure applied is about 400 kPa to about 700 kPa. For example, the pressure applied is about 400 kPa to about 650 kPa. For example, the pressure applied is 400 kPa to about 600 kPa. For example, the pressure applied is about 400 kPa to about 500 kPa.

For example, the separating of the macrofiber depleted suspension 1H is carried out less than 6 hours from the providing of the plant fragments. For example, the separating of the macrofiber depleted suspension 1H is carried out less than 5 hours from the providing of the plant fragments. For example, the separating the of macrofiber depleted suspension 1H is carried out less than 4 hours from the providing of the plant fragments. For example, the separating of the macrofiber depleted suspension 1H is carried out less than 3 hours from the providing of the plant fragments. For example, the separating of the macrofiber depleted suspension 1H is carried out less than 2 hours from the providing of the plant fragments. For example, the separating of the macrofiber depleted suspension 1H is carried out less than 1 hours from the providing of the plant fragments. For example, the separating of the macrofiber depleted suspension 1H is carried out about 1 hour to about 6 hours from the providing of the plant fragments.

For example, the separating of the macrofiber depleted suspension 1H and 1H.2 comprises twice pressing (e.g. 1A.1 and 1A.2) the plant fragments 0B. In this context, the second pressing (1A.2) comprises rehydrating the macrofiber fraction 1B containing the plant macrofibers resulting from the first pressing (1A.2), and extracting from the rehydrated material a second volume of liquid or a second volume of macrofiber depleted suspension 1H.2. For example, the rehydrating comprises adding water and/or a recirculated liquid coming from downstream activities of the global process. For example, the first macrofiber depleted suspension 1H can be used for the second fractionation F2 while the second macrofiber depleted suspension 1H.2 can be subject to a suspension clarification 3C and then can be subject to an extraction of molecules or compounds as performed in the compound extraction 3E in the third fractionation F3. For example, the first and second macrofiber depleted suspensions 1H and 1H.2 can be used, mixed or not, for the second fractionation F2. For example, wherein the plant fragments are twice pressed, the resulting macrofiber fraction 1B comprises macrofibers having undergone a first pressing and/or a second pressing (e.g. 1A.1 and 1A.2).

For example, the process of macrofiber separation 1A comprises providing an antifoaming agent to the plant fragments.

The macrofiber depleted suspension 1H contains suspended structures and/or compounds of small size as well as molecules dissolved therein or not, such as for example saponin. The macrofiber depleted suspension 1H also comprises different solids and solubles of interest such as compounds, molecules and/or further downstream compositions or suspension, with minimal degradation of such compounds or molecules. As further described hereinafter and illustrated in FIG. 10B, a two stage pressing (1A.1 and 1A.2), including watering of the first pressed cake (1B) just upstream of the second pressing stage, permits capturing at a higher rate of such desirable solid and soluble matters, while preserving quality and integrity. A size distribution analysis of the macrofiber depleted suspension 1H indicating that, excluding microfibers included therein and having a length of about 20-200 microns, more than 75% of the solid particles are between 5 and 10 microns, which is the average size of the chloroplast, is an indicator of the quality of the macrofiber separation 1A. Furthermore, a substantial proportion of microfibers that have not been trapped in the macrofiber agglomerates constituting the macrofiber fraction 1B may remain in the macrofiber depleted suspension 1H. As mentioned above, these microfibers have an average size or length between 20 and 200 microns. Finally, it should be noted that the macrofiber depleted suspension 1H may also contain residual antioxidant and/or antimicrobial agent such as for example metabisulfite added in the upstream process to the plant fragments 0B during the biomass preparation 0A.

The macrofiber fraction 1B comprises a variety of structures including macrofibers, microorganisms (e.g. bacteria, yeast, fungi), whole plant cells as well as compounds and/or molecules such as proteins, peptides, amino acids, pigments, all able to retain a certain liquid volume and/or are totally or partially bounded to said liquid. The macrofiber fraction 1B may also contain residual antioxidant and/or antimicrobial agent such as metabisulfite added in the upstream process to the plant fragments 0B during the biomass preparation 0A. Furthermore, it was observed that most of the plant's saponin was carried away by (or dissolved in) the liquid fraction, or macrofiber depleted suspension 1H, which in turn improves the nutritional value and digestibility of the macrofiber fraction 1B.

Unless otherwise indicated, "macrofibers" in the present section refer to macrofibers comprised in the macrofiber fraction 1B, isolated macrofibers and to macrofibers comprised in a macrofiber composition 1D (the latter being further described below).

For example, the macrofiber fraction 1B and macrofiber composition 1D herein disclosed comprise Fabaceae family plant macrofibers. For example, the plant is from the *Medicago* spp. For example, the plant is from the *Medicago sativa* specie (i.e. alfalfa) or subspecies.

For example, the plant macrofibers, macrofiber fraction 1B and/or macrofiber composition 1D have a moisture content of about 50 wt. % to about 75 wt. %. For example, the plant macrofibers, macrofiber fraction 1B and/or macrofiber composition 1D have a moisture content of about 55 wt. % to about 65 wt. %. For example, the plant macrofibers, macrofiber fraction 1B and/or macrofiber composition 1D have a moisture content of about 60 wt. % to about 63 wt. %.

For example, the plant macrofibers, macrofiber fraction 1B and/or macrofiber composition 1D have a decrease in saponin content of about 30% to about 70% relative to a reference *Medicago* spp plant. For example, the plant macrofibers, macrofiber fraction 1B and/or macrofiber composition 1D have a decrease in saponin content of about 50% to about 70% relative to a reference *Medicago* spp plant. For example, the reference *Medicago* spp plant are the plant fragments (0B). For example, the plant macrofibers, macrofiber fraction 1B and/or macrofiber composition 1D have a decrease in saponin content of about 60% to about 65% relative to reference plant fragments (0B). For example, the plant macrofibers, macrofiber fraction 1B and/or macrofiber composition 1D have a decrease in medicagenic acid saponin content of about 50% to about 70% relative to a reference *Medicago* spp plant. For example, the plant macrofibers, macrofiber fraction 1B and/or macrofiber composition 1D have a decrease in medicagenic acid saponin content of about 60% to about 65% relative to a reference *Medicago* spp plant.

For example, the reference *Medicago* spp plant consists of plant fragments 0B. For example, the reference *Medicago* spp plant is alfalfa.

For example, the plant macrofibers, macrofiber fraction 1B and/or macrofiber composition 1D have a saponin content of about 1.0 to 5.0 mg/g (dry basis). For example, the plant macrofibers, macrofiber fraction 1B and/or macrofiber composition 1D have a saponin content of about 1.5 to 4.0 mg/g (dry basis). For example, the plant macrofibers, macrofiber fraction 1B and/or macrofiber composition 1D have a saponin content of less than 1.5 mg/g (dry basis).

For example, the plant macrofibers, macrofiber fraction 1B and/or macrofiber composition 1D have a saponin content of about 0.5 mg/g (dry basis), about 0.6 mg/g (dry basis), about 0.7 mg/g (dry basis), about 0.8 mg/g (dry basis), about 0.1 mg/g (dry basis), about 1.0 mg/g (dry basis), about 1.2 mg/g (dry basis), about 1.4 mg/g (dry basis), about 1.6 mg/g (dry basis), about 1.8 mg/g (dry basis), about 2.0 mg/g (dry basis), about 2.5 mg/g (dry basis), about 3.0 mg/g (dry basis), about 3.5 mg/g (dry basis), about 4.0 mg/g (dry basis), about 4.0 mg/g (dry basis), about 4.5 mg/g (dry basis) or about 5.0 mg/g (dry basis). For example, the saponin is medicagenic acid saponin.

For example, the plant macrofibers, macrofiber fraction 1B and/or macrofiber composition 1D have a protein content of about 10% w/w to about 30% w/w (dry basis). For example, the plant macrofibers, macrofiber fraction 1B and/or macrofiber composition 1D have a protein content of about 12% w/w to about 24% w/w (dry basis). For example, the plant macrofibers, macrofiber fraction 1B and/or macrofiber composition 1D have a protein content of about 15% w/w to about 20% w/w (dry basis). For example, the plant macrofibers, macrofiber fraction 1B and/or macrofiber composition 1D have a protein content of about 16% w/w to about 18% w/w (dry basis).

For example, the plant macrofibers have an average length of about 10 mm to about 100 mm. For example, the macrofibers have an average length of about 10 mm to about 50 mm. For example, at least 75% of the macrofibers have an average length of less than about 20 mm. For example, at least 80% of the macrofibers have an average length of less than about 20 mm.

For example, the antioxidant is metabisulfite, benzoate, optionally sodium metabisulfite, potassium metabisulfite, sodium benzoate or potassium benzoate.

Macrofiber Conditioning 1C

In order to preserve quality and palatability, the macrofiber fraction 1B comprising plant macrofibers, may be conditioned in order to obtain a macrofiber composition 1D, as shown for example in FIGS. 1, 2A, 2B and 3. For example, the conditioning comprises quickly packaging and compressing the macrofiber fraction 1B according to the needs, in receptacles or containers. If care is taken to harvest at an early plant growth stage (e.g. when the plant still displays a high leaf/stem ratio), to cut sharply (e.g. between 10-50 mm), to press the plant fragments 0B under low shearing and pressure differential with limited temperature increase and to package rapidly, e.g. within about 30 minutes or about 1 hour of macrofiber separation 1A, macrofiber conditioning 1C will lead to a macrofiber composition 1D having for example about 60%-65% moisture and having about between 15 and 20% w/w protein content (dry basis). Using a hermetic receptacle or container, fermentation, or ensiling, may bring down the pH of the macrofiber composition 1D to a desired pH, for example below 4.3, within about 3-4 weeks. Alternatively, a bacterial inoculum may be added to the macrofiber fraction 1B prior to packaging during the macrofiber conditioning 1C. A supplement, antioxidant and/or antimicrobial agent can be also be added to the macrofiber fraction 1B prior to packaging.

For example, the macrofiber fraction 1B is conditioned to obtain a macrofiber composition 1D. For example, the conditioning is carried out less than 4 hours from the macrofiber separation 1A. For example, the conditioning is carried out less than 3 hours from the macrofiber separation 1A. For example, the conditioning is carried out less than 2 hours from the macrofiber separation 1A. For example, the conditioning is carried out in about 1 hour to about 4 hours from the macrofiber separation 1A.

For example, the conditioning comprises mixing the macrofiber fraction 1B with an antioxidant and/or an antimicrobial agent. For example, the antioxidant and/or the antimicrobial agent is citric acid, metabisulfite, optionally sodium metabisulfite or potassium metabisulfite. For example, the antioxidant and/or the antimicrobial agent is citric acid, sodium benzoate or potassium metabisulfite.

For example, the conditioning comprises adding a nutritional supplement to the macrofiber fraction 1B.

For example, the conditioning comprises packaging the macrofiber fraction 1B. For example, the conditioning comprises ensiling the macrofiber fraction 1B following packaging. For example, the packaging is carried out less than 6 hours, less than 4 hours, less than 3 hours, less than 2 hours or less than 1 hour from the separating of the macrofiber depleted suspension 1H. For example, the packaging is carried out in about 1 hour to about 6 hours from the separating of the macrofiber depleted suspension 1H.

For example, the conditioning comprises compacting and hermetically sealing the macrofiber fraction 1B in a hermetic receptacle. For example, the conditioning comprises compacting and hermetically sealing the macrofiber fraction 1B in a hermetic receptacle under modified atmosphere or inert atmosphere, optionally $N_2$ or nitrogen.

For example, the macrofiber fraction 1B is compacted at a ratio of about 3:1, For example, the macrofiber fraction 1B is compacted at a ratio of about 2.8:1. For example, the macrofiber fraction 1B is compacted at a ratio of about 2.6:1. For example, the macrofiber fraction 1B is compacted at a ratio of about 2.4:1. For example, the macrofiber fraction 1B is compacted at a ratio of about 2.3:1. For example, the macrofiber fraction 1B is compacted at a ratio of about 2.2:1. For example, the macrofiber fraction 1B is compacted at a ratio of about 2:1. For example, the macrofiber fraction 1B is compacted at a ratio of about 1.8:1. For example, the macrofiber fraction 1B is compacted at a ratio of about 1.5:1.

For example, the macrofiber fraction 1B is hermetically sealed, optionally in a receptable. For example, the receptacle has a capacity of about 20 liters to about 2,000 liters. For example, the receptacle is a polymer pouch or bag, optionally an opaque polymer pouch or bag. For example, the macrofiber fraction 1B is hermetically sealed under modified atmosphere or inert atmosphere, optionally $N_2$ or nitrogen.

For example, the conditioning comprises mixing the macrofiber fraction 1B with an acid, optionally an organic acid.

For example, the conditioning comprises inoculating the macrofiber fraction 1B with *Lactobacillus* bacteria to accelerate fermentation. For example, the conditioning comprises inoculating the macrofiber fraction 1B with *Bacillus* bacteria, e.g. *Bacillus subtilis*, to stimulate a beneficial microbial activity. For example, the fermentation is anaerobic. For example, the fermentation is aerobic.

For example, the macrofiber fraction 1B is fermented for a period of about 2 weeks to about 6 weeks. For example, the macrofiber fraction 1B is fermented for a period of about 3 weeks to about 4 weeks.

Following a fermentation period, the resulting fermented macrofiber composition 1D has lowered pH. For example, the macrofiber composition 1D has a pH between 4.0 and 5.0. For example, macrofiber composition 1D has a pH between 4.0 and 4.5. For example, the macrofiber composition 1D has a pH between 4.0 and 4.4. For example, the macrofiber composition 1D has a pH between 4.0 and 4.3.

For example, the macrofiber composition 1D has a pH of less than about 5.0. For example, the macrofiber composition 1D has a pH of less than about 4.8. For example, the macrofiber composition 1D has a pH of less than about 4.7. For example, the macrofiber composition 1D has a pH of less than about 4.6. For example, the macrofiber composition 1D has a pH of less than about 4.5. For example, the macrofiber composition 1D has a pH of less than about 4.4. For example, the macrofiber composition 1D has a pH of less than about 4.3.

For example, the conditioning comprises adding vitamins and fatty acids to increase the nutritional value of the macrofiber composition 1D as end product.

For example, the macrofiber composition 1D has a moisture content of about 50 wt. % to about 75 wt. %. For example, the macrofiber composition 1D has a moisture content of about 55 wt. % to about 65 wt. %. For example, the macrofiber composition 1D has a moisture content of about 60 wt. % to about 63 wt. %.

For example, the macrofiber composition 1D further comprises water.

As shown in Table 9, the resulting macrofiber composition 1D has a decreased medicagenic acid saponin content compared to plant fragments 0B.

For example, the macrofiber composition 1D has a decrease in saponin content of about 30% to about 70% relative to a reference *Medicago* spp plant. For example, the macrofiber composition 1D has a decrease in saponin content of about 50% to about 65% relative to plant fragments 0B.

For example, the macrofiber composition 1D has a decrease in medicagenic acid saponin content of about 30% to about 70% relative to plant fragments 0B. For example, the macrofiber composition 1D has a decrease in medicagenic acid saponin content of about 40% to about 65% relative to plant fragments 0B. For example, the reference *Medicago* spp plant consists of plant fragments 0B. For example, the reference *Medicago* spp plant is alfalfa. For example, the macrofiber composition 1D has a medicagenic acid saponin content of about 0.4 to 5.5 mg/g (dry basis). For example, the macrofiber composition 1D has a medicagenic acid saponin content of less than 1.5 mg/g (dry basis).

Compound Extraction 1F

Referring to FIGS. 2A, 2B and 3, a compound extraction 1F may be also carried out from the macrofiber fraction 1B to obtain high value molecules and/or compounds. These molecules and/or compounds once extracted can be purified at different levels and used as active ingredients for the development of end products useful in various industries.

For example, the macrofiber fraction 1B can be a source of proteins, enzymes, peptides, amino acids, fatty acids, fatty alcohols, terpenes, phenols and pigments, as shown in the Examples herein.

For example, the macrofiber fraction 1B can be a source of protein, optionally a protein identified any one of Tables 10 to 16. For example, the macrofiber fraction 1B can be a source of peptide. For example, the macrofiber fraction 1B can be a source of fatty alcohol, optionally triacontanol (as shown in Example 14).

The macrofiber composition 1D may be commercialized and used as animal feed 1E namely, as shown in FIGS. 2 and 3.

Second Fractionation F2

As they have been maintained substantially intact during the first fractionation F1, the chloroplasts may be separated from the soluble plant components. However, prior to the chloroplast separation 3A, the macrofiber depleted suspension 1H, obtained from the macrofiber separation 1A, undergoes a second fractionation F2 which comprises inter alia a microfiber depletion 2A as shown in FIGS. 1, 2A, 2B, 4, 5, 6, 7, 8 and 9. The microfiber depletion 2A (or microfiber separation) removes the plant microfibers originating from the macrofiber separation 1A. It was discovered that it is important to remove the microfibers at this stage as these can act as an abrasive during further manipulation of chloroplasts which can in turn affect their integrity. Microfiber depletion 2A provides a microfiber fraction 2AA and a microfiber depleted suspension 2G containing structures, mainly intact chloroplasts, as well as some compounds and molecules, dissolved therein or not. Similar to the macrofiber fraction 1B, the microfiber fraction 2AA may undergo microfiber conditioning 2B to obtain a microfiber composition 2C as end product suitable for human and animal nutrition 2D and/or a compound extraction 2E to extract high value molecules and/or compounds for further end product development 3I.

Microfiber Depletion 2A

Figure 14:
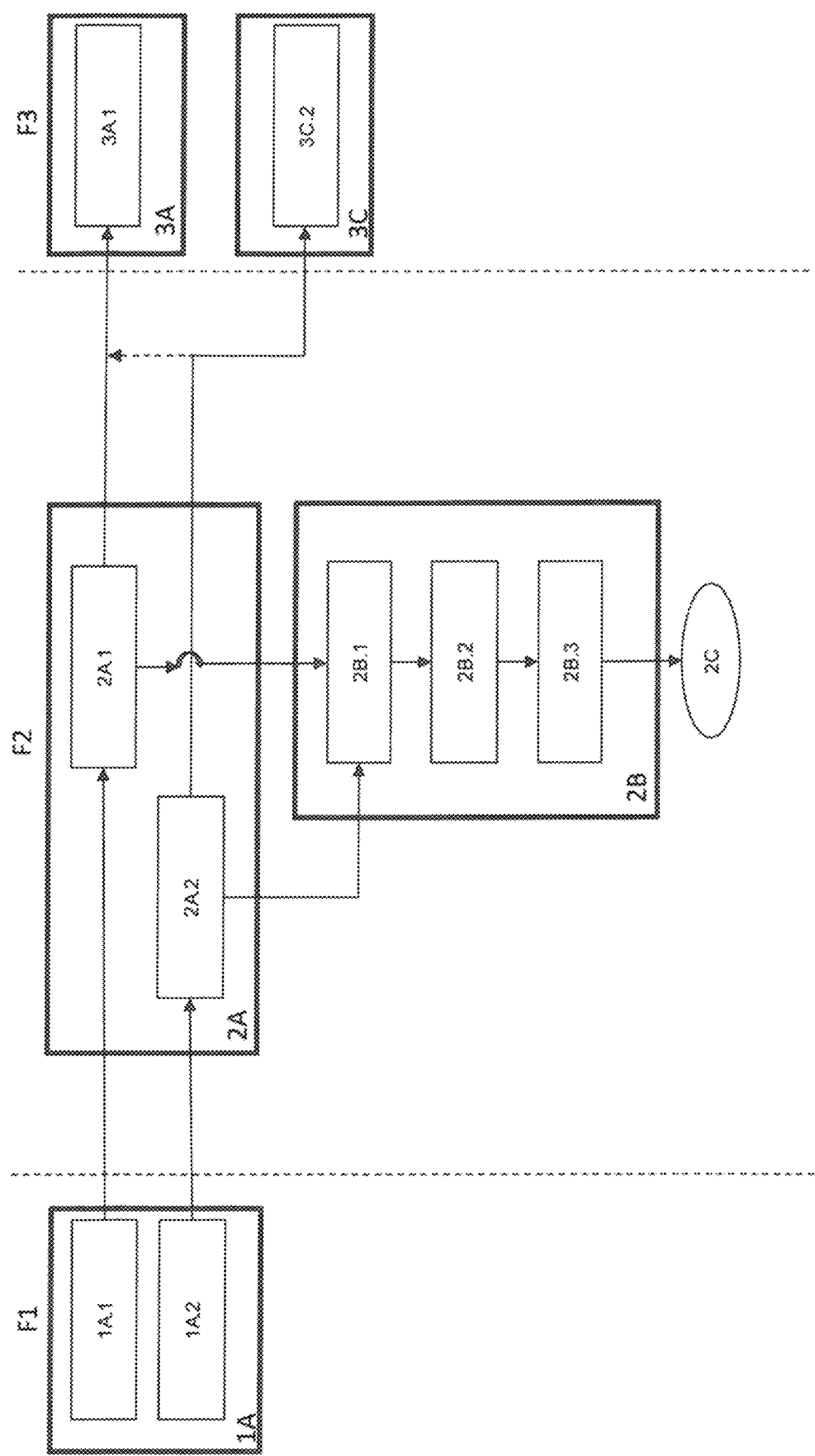
FIG. 14 is a flow sheet diagram of the second fractionation F2, according to an embodiment.

It will be understood that various suitable methods for depleting microfibers from the liquid fraction, or macrofiber depleted suspension 1H, may be used, including for example sieving, pressure sieving, centrifugation and decanting. Where the plant fragments are twice pressed, the microfibers may come from two macrofiber depleted suspensions 1H and 1H.2. FIG. 14 shows an example of this particular process where two macrofiber separations 1A.1 and 1A.2 occur.

For example, the separating the microfiber fraction 2AA comprises separating by sieving, pressure sieving, centrifugation and/or decanting. For example, the separating the microfiber fraction 2AA comprises filtering the macrofiber depleted suspension 1H using a sieve having a size of about 20 microns to about 155 microns. For example, the separating the microfiber fraction 2AA comprises filtering the macrofiber depleted suspension 1H using a sieve having a size of about 30 microns to about 90 microns. For example, the separating the microfiber fraction 2AA comprises filtering the macrofiber depleted suspension 1H using a sieve having a size of about 40 microns to about 90 microns. For example, the separating the microfiber fraction 2AA comprises filtering the macrofiber depleted suspension 1H using a sieve having a size of about 80 microns to about 90 microns.

For example, the separating further comprises separating a second microfiber fraction 2AA from the second macrofiber depleted suspension 1H. For example, the separating the second microfiber fraction 2AA comprises filtering the second macrofiber depleted suspension 1H using a sieve having a size of about 20 microns to about 155 microns, about 30 microns to about 90 microns, about 40 microns to about 90 microns or about 80 microns to about 90 microns. For example, the second microfiber fraction 2AA is combined with the microfiber fraction 2AA.

Similarly to the macrofiber depleted suspension 1H, the microfiber depleted suspension 2G, resulting from the microfiber depletion 2A, contains suspended structures, mainly chloroplasts and/or compounds of small size as well as molecules dissolved therein or not, such as for example saponin. A size distribution analysis of the microfiber depleted suspension 2G produced indicates a sharp distribution profile with a peak between 5-6 microns and with more than 75% of the particles between 4 and 10 microns, which is the average size of the chloroplast. Particle size may be determined using suitable methods for example using Dynamic light scattering to extrapolate their relative volume (as further described in Example 11). This is an indicator of the quality of the macrofiber separation 1A as well as the microfiber depletion 2A in terms of chloroplast integrity. Broken chloroplast fragments would show a broad particle distribution with peaks between 0.5 and 2 microns. It may be also observed remaining smaller microfibers which have a size inferior to the device separation capacity used for the microfiber depletion 2A. It should be noted that the microfiber depleted suspension 2G may also contain residual antioxidant and/or antimicrobial agent, such as citric acid or metabisulfite, added in the upstream process.

Unless otherwise indicated, "microfibers" in the present section refer to microfibers comprised in the microfiber fraction 2AA, to isolated microfibers and to microfibers comprised in a microfiber composition 2C (the latter being further described below).

For example, at least 75% of solid particles in the microfiber depleted suspension 2G have an average size of about 5 to about 10 microns.

The microfiber fraction 2AA and microfiber composition 2C comprise a variety of structures including microfibers (e.g. with a size superior to the device separation capacity), microorganisms (e.g. bacteria, yeast, fungi), whole plant cells, as well as compounds and/or molecules all able to retain a certain liquid volume and/or are totally or partially bounded to said liquid. The microfiber fraction 2AA and microfiber composition 2C comprise may also contain residual antioxidant and/or antimicrobial agent, such as citric acid or metabisulfite, added in the upstream process. Furthermore, it was observed also that most of the plant's saponin was carried away by (or dissolved in) the liquid fraction, or microfiber depleted suspension 2G.

For example, the antioxidant and/or the antimicrobial agent is citric acid, metabisulfite, benzoate, optionally sodium metabisulfite, potassium metabisulfite, sodium benzoate or potassium benzoate.

For example, the microfiber fraction 2AA and microfiber composition 2C comprise Fabaceae family plant microfibers. For example, the plant is from the *Medicago* genus. For example, the plant is from the *Medicago sativa* species (alfalfa).

For example, the microfibers have an average length of about 40 microns to about 300 microns. For example, the microfibers have an average length of about 40 microns to about 200 microns. For example, the microfibers have an average length of about 40 microns to about 160 microns. For example, the microfibers have an average length of about 80 microns to about 200 microns. For example, the microfibers have an average length of about 90 microns to about 180 microns. For example, the microfibers have an average length of about 100 microns to about 160 microns.

For example, the microfiber fraction 2AA has a moisture of about 70 wt. % to about 90 wt. %. For example, the microfiber fraction 2AA has a moisture of about 75 wt. % to about 90 wt. %. For example, the microfiber fraction 2AA has a moisture of about 80 wt. % to about 90 wt. %. For example, the microfiber fraction 2AA has a moisture of about 85 wt. % to about 90 wt. %. For example, the microfiber fraction 2AA has a moisture of about 85 wt. % to about 88 wt. %.

As described in Table 6, nutrients and other components of the presently disclosed microfibers were analyzed and compared to other known foods that are a source of fiber (namely crude wheat bran and dehydrated bananas).

For example, the microfiber fraction 2AA and/or microfiber composition 2C have a protein content of about 20% w/w to about 40% w/w (dry basis). For example, the microfiber fraction 2AA and/or microfiber composition 2C have a protein content of about 25% w/w to about 40 w/w (dry basis). For example, the microfiber fraction 2AA and/or microfiber composition 2C have a protein content of about 25% w/w to about 35% w/w (dry basis). For example, the microfiber fraction 2AA and/or microfiber composition 2C have a protein content of about 30% w/w to about 35% w/w (dry basis).

For example, the microfiber fraction 2AA and/or microfiber composition 2C have a triacontanol content of about 2,000 µg/g (dry basis) for microfibers presenting a humidity content of 92%. For example, the microfiber fraction 2AA and/or microfiber composition 2C have a triacontanol content of about 1,500 µg/g to 3,000 µg/g (dry basis) for fibers microfibers presenting a humidity content of 92%.

For example, the microfiber fraction 2AA and/or microfiber composition 2C have a beta carotene content of about 80 µg/g to about 120 µg/g (dry basis). For example, the microfiber fraction 2AA and/or microfiber composition 2C have a beta carotene content of about 90 µg/g to about 110 µg/g (dry basis).

For example, the microfiber fraction 2AA and/or microfiber composition 2C have a natural antioxidant content of about 300 µmol Trolox Equivalents (TE)/g to about 450 µmol TE/g (dry basis). For example, the microfiber fraction 2AA and/or microfiber composition 2C have a natural antioxidant content of about 300 µmol TE/g to about 400 µmol TE/g (dry basis).

Microfiber Conditioning 2B

The microfiber fraction 2AA, resulting from the microfiber depletion 2A, may undergo a conditioning to preserve the qualities of its constituents and even to increase them. The conditioning comprises for example quickly drying the microfiber fraction 2AA to decrease the total moisture content and thus reduce the oxidation.

For example, the conditioning comprises drying the microfiber fraction 2AA. For example, the resulting microfiber composition 2C has a moisture content of about 5% w/w to about 20% w/w. For example, the microfiber composition 2C has a moisture content of about 6% w/w to about 16% w/w. For example, the microfiber composition 2C has a moisture content of about 8% w/w to about 14% w/w. For example, the microfiber composition 2C has a moisture content of about 1% w/w to about 12% w/w.

According to the needs, a nutritional supplement, an antioxidant, an antimicrobial agent, a conservation agent and/or a microbial inoculum, having beneficial function, may be added to the microfiber fraction 2AA prior to packaging during the microfiber conditioning 2B. The packaging to protect the resulting microfiber composition 2C is selected according to the preservation, transport or end user requirements.

For example, the microfiber conditioning 2B comprises mixing to the microfiber fraction 2AA an antioxidant and/or an antimicrobial agent. For example, the antioxidant and/or the antimicrobial agent is citric acid, metabisulfite, benzoate, optionally sodium metabisulfite, potassium metabisulfite, sodium benzoate or potassium benzoate.

For example, wherein the microfiber conditioning 2B comprises mixing to the microfiber fraction 2AA an omega-3 fatty acid, an omega-6 fatty acid and/or vitamins.

For example, microfiber conditioning 2B comprises inoculating the microfiber fraction 2AA with bacteria. For example, the bacteria is *Lactobacillus* spp and/or *Bacillus* spp (e.g. *Bacillus subtilis*).

In an embodiment, there are provided isolated Fabaceae family plant microfibers obtained according to the process herein disclosed. In another embodiment, there is provided a composition comprising Fabaceae family plant microfibers obtained according to the process herein disclosed. For example, the plant is from the *Medicago* genus. For example, the plant is the *Medicago sativa* species or subspecies.

The resulting microfiber composition 2C is a source of various beneficial dietary nutrients such as proteins, pigments and fiber, and may, for example, be used as a supplement for human and animal nutrition 2D considering its effect on the health and the body performance.

For example, a conservation agent, antioxidant and/or the antimicrobial agent e.g. citric acid, benzoate, metabisulfite and/or other food additive e.g. vitamins, omega-3 fatty acid or omega-6 fatty acid may be added to the microfiber fraction 2AA during the microfiber conditioning 2B.

For example, the conservation agent, antioxidant and/or the antimicrobial agent is citric acid, metabisulfite, benzoate, optionally sodium metabisulfite, potassium metabisulfite, sodium benzoate or potassium benzoate.

For example, the microfiber conditioning 2B comprises packaging the microfiber fraction 2AA in a hermetic receptacle. For example, the receptacle is a polymer pouch, bag or container.

For example, the microfiber conditioning 2B comprises hermetically sealing the microfiber fraction 2AA under vacuum or in a hermetic receptacle optionally under modified atmosphere or inert atmosphere, optionally $N_2$ or nitrogen.

For example, the microfiber conditioning 2B comprises packaging the microfiber fraction 2AA in an opaque receptacle to block the light and thus reduce the oxidation.

For example, the microfiber conditioning 2B comprises drying the microfibers to a moisture content of about 5 wt. % to about 20 wt. %, about 6 wt. % to about 16 wt. %, about 8 wt. % to about 14 wt. % or about 10 wt. % to about 12 wt. %.

Compound Extraction 2E

Referring to FIGS. 1, 2A, 2B and 4, a compound extraction 2E can be also carried out from the microfiber fraction 2AA to obtain high value molecules and/or compounds. These molecules and/or compounds, once extracted, can be purified at different levels and used as active ingredients for the development of end products useful in various industries.

For example, the microfiber fraction 2AA can be a source of proteins, enzymes, peptides, amino acids, fatty acids, fatty alcohols, terpenes, phenols, pigments and mixtures thereof, as shown in the Examples herein.

For example, as shown in Example 14, the microfiber fraction 2AA can be a source of triacontanol presenting recognized biostimulation effect on plants.

For example, the microfiber fraction 2AA can be a source of protein, optionally a protein identified any one of Tables 10 to 16. For example, the microfiber fraction 2AA can be a source of peptide.

Third Fractionation F3

After removing microfibers in the second fractionation F2, the third fractionation F3 can be achieved, as shown for example in FIGS. 1, 2A, 2B and 5. Similar to the previous fractionations, the third fractionation F3 is represented by process activities (rectangle), intermediary and precursor products (oval) and uses (diamond) from 3A through 3K. The objective of the third fractionation F3 is to separate, as much as possible, intact chloroplasts from the microfiber depleted suspension 2G as well as to generate a chloroplast reduced suspension 3B, containing various dissolved components and/or molecules inter alia saponins. To do so, the microfiber depleted suspension 2G undergoes a chloroplast separation 3A, optionally using different approaches or techniques, to obtain a chloroplast suspension 3K and a chloroplast reduced suspension 3B. The latter suspension may undergoes a suspension clarification 3C, optionally using different methods, to remove contaminants to obtain a clarified suspension 3D and a second chloroplast suspension 3CC. Finally, from this clarified suspension 3D, a compound extraction 3E may be carried out to obtain inter alia a saponin-enriched powder 3F which undergoes a saponin powder conditioning 3G resulting in a saponin precursor 3H. This precursor can be used for further end product development 3I.

Chloroplast Separation 3A

It will be understood that various suitable methods for separating chloroplast from a liquid fraction comprising chloroplasts, for example the microfiber depleted suspension 2G as starting material, may be used including, for example, centrifugation, tangential flow filtration (TFF), flocculation/decanting, sedimentation, filtration, and equivalent methods. In all cases, chloroplast separation 3A should avoid excessive shearing, temperature increase, pressure variation, molarity variation and other conditions causing chloroplast breakage and consequently dispersion of soluble components of the chloroplasts in the liquid suspension (e.g. chloroplast reduced suspension 3B). Care is also taken to maintain the pH within physiological ranges, (e.g. above 4.5) to prevent coagulation of soluble components (mostly proteins) found within or outside the chloroplasts. For pH adjustment, when required, it is preferable to use mild or weak "natural" organic acids. Co-precipitation of cellular components and chloroplasts is also to be avoided.

For example, the chloroplast separation 3A may be carried out by acidifying the microfiber-depleted suspension 2G to a pH of about 4.8 to about 5.0 and separating its components by centrifugation (e.g. at 10,000 g).

For example, the chloroplasts may also be separated by tangential flow filtration, optionally using a filter of 300 kDa and/or 0.2 micron.

For example, the chloroplast separation 3A is carried out at a temperature of about 4° C. to about 45° C. For example, the chloroplast separation 3A is carried out at a temperature of about 4° C. to about 40° C. For example, the chloroplast separation 3A is carried out at a temperature of about 15° C. to about 42° C. For example, the chloroplast separation 3A is carried out at a temperature of about 20° C. to about 38° C. For example, the chloroplast separation 3A is carried out at a temperature of about 20° C. to about 34° C. For example, the chloroplast separation 3A is carried out at a temperature of about 20° C. to about 37° C. For example, the separating the chloroplasts is carried out at a temperature of about 25° C. to about 34° C.

For example, the separating the chloroplasts from the microfiber depleted suspension comprises sedimenting the chloroplasts and optionally isolating the sedimented chloroplasts. For example, the chloroplasts are sedimented by acidifying the microfiber depleted suspension 2G to a pH of about 4.0 to about 5.5. For example, the chloroplasts are sedimented by acidifying the microfiber depleted suspension 2G to a pH of about 4.2 to about 5.2. For example, the chloroplasts are sedimented by acidifying the microfiber depleted suspension 2G to a pH of about 4.4 to about 5.2. For example, the chloroplasts are sedimented by acidifying the microfiber depleted suspension 2G to a pH of about 4.6 to about 5.2. For example, the chloroplasts are sedimented by acidifying the microfiber depleted suspension 2G to a pH of 4.8 to about 5.2. For example, the acidifying comprises mixing the microfiber depleted suspension 2G with an acid. For example, citric acid or other 4-C or 5-C organic acids may be used for this purpose.

For example, the sedimented chloroplasts are isolated by centrifugation at a force of about 2,000 g to about 15,000 g. For example, the sedimented chloroplasts are isolated by centrifugation at a force of about 2,000 g to about 10,000 g. For example, the sedimented chloroplasts are isolated by centrifugation at a force of about 4000 g to about 12,000 g. For example, the sedimented chloroplasts are isolated by centrifugation at a force of about 10,000 g.

As mentioned above, the chloroplast separation 3A will yield two fractions, namely a chloroplast suspension 3K and a chloroplast reduced suspension 3B (as shown for example in FIGS. 2A, 2B, 5, 6, 7, 8 and 9).

The chloroplast suspension 3K may contain more than 75% of intact chloroplasts when compared to the initial chloroplast level as observed e.g. under Dynamic light scattering in the plant fragments 0B. The chloroplast suspension 3K also contains about 30% of solid content (w/v) representing 30% of the initial volume introduced during chloroplast separation 3A, and a high level of protein (e.g. from 25 to 50%). It should be noted that the chloroplasts suspension 3K may also contain residual antioxidant and/or antimicrobial agent, such as metabisulfite and/or an organic acid (such as citric acid), added in the upstream process.

The chloroplast reduced suspension 3B still contains about 30% of the green material (e.g. chloroplasts) from the initial volume observed in the microfiber depleted suspension 2G, and other residual protein, sugar, plant structures, characterized by about a 6.5% w/v solid content and about 3% w/w (dry basis). This fraction also contains soluble material including more than 70% of the medicagenic acid saponins contained in the microfiber depleted suspension 2G. Similarly to the chloroplast suspension 3K, the chloroplast reduced suspension 3B may also contain residual antioxidant and/or antimicrobial agent, such as citric acid, metabisulfite and/or organic acid (such as citric acid), added in the upstream process.

A size distribution analysis of the two fractions (3B and 3K) demonstrates that the chloroplasts contained therein are mostly intact chloroplasts at an average of 5-7 μm with limited aggregation due to acidification. Intactness of chloroplast physical structure is maintained up to this stage of the process flow by strict control of mechanical, biological and chemical stresses during process. The combination of biomass maturity upon harvest, mild but efficient biomass conditioning, low-shearing and low-differential pressure during mechanical disruption, control of temperature (e.g. >4° C. and <34° C.) in the press, weak organic acids for acidification, control of pH (e.g. 4.8<pH<5.1) during acidification and/or control of temperature during centrifugation are desirable in maintaining chloroplast integrity. Maintaining chloroplast integrity sequesters chloroplast components within the chloroplast. Protecting chloroplast integrity allows the mechanical separation of whole chloroplasts from the liquid fraction in one sedimentation activity. This is important to the continuity of the process flow as it also allows the mechanical separation of one important protein component of the plant leaf material, Rubisco (ribulose bis-phosphate carboxylase), which is the major chloroplast protein and the most important plant protein with regards to nutrition. In such highly controlled process limitations and performances, some other specific products could be selectively obtained, in quantity with high purity, as carotenes, chlorophyll, antioxidants, omega-3 phospholipids.

Chloroplast Clarification 3C

The chloroplast reduced suspension 3B contains some solids, such as chloroplasts and/or other green material of small dimension, and is clarified via suspension clarification 3C to selectively separate soluble material, such as medicagenic acid saponins. The obtained clarified suspension 3D is ready for use in compound extraction 3E. The clarifying can be carried out by centrifugation, tangential flow filtration (TFF), ultrafiltration, flocculation/decanting or equivalent method therefor. For flocculation/decanting, it will be understood that suitable methods are based on the use of an organic agent. Combinations of any of the foregoing methods may be used to separate the chloroplast reduced suspension 3B. It should be noted that size distribution can be used at this stage to verify that greater than 75% of particles in the resulting retentate remain between about 4-7 microns for acidified material. It should be noted that the suspension clarification 3C can also be carried out for the microfiber depleted suspension 2G.2 resulting of the subactivity 2A.2 if occurring, as described in FIGS. 14 and 15.

In another embodiment, with reference to FIGS. 2A and 2B, chloroplasts remaining in the chloroplast reduced suspension 3B can be separated directly from other low-molecular weight components using TFF (e.g. ceramic, hollow fiber, membrane, cross-flow). Care should be taken to avoid use of TFF at low molecular cut-off to keep out soluble components in the retentate, for example lower than 300 kDa, and at a temperature higher than 34° C. or lower than 4° C. and without addition of any organic acid. This prevents altering the chloroplast integrity in the second chloroplast suspension 3CC and provides a sterile filtrate (e.g. clarified suspension 3D). Maintaining the temperatures below 34° C. also preserves the biochemical integrity of the valuable components (for example but without restriction for the second chloroplast suspension 3CC, carotenes, chlorophyll, antioxidants, anthocyanins, proteins, omega-3 phospholipids). Finally, this clarifying method requires that the flows of recirculation be adjusted to restrict shearing, and because of this, about 70% of the loaded volume is contained in the filtrate (e.g. clarified suspension 3D) characterized by a solid content lower than 1% w/v.

For example, the suspension clarification 3C is carried out by filtration at low molecular cut-off weight between 200-600 kDaltons. For example, the suspension clarification 3C is carried out is carried out at low molecular weight cut-off between 200-500 kDaltons. For example, the suspension clarification 3C is carried out is carried out at low molecular weight cut-off between 200-400 kDaltons. For example, the suspension clarification 3C is carried out is carried out at low molecular weight cut-off 300 kDaltons As per the hereinabove embodiment, the first fraction resulting from the suspension clarification 3C (or 3C.1 as referred to in FIG. 10B), i.e. the second chloroplast suspension 3CC (as shown in FIGS. 2A, 2B and 10B) may contain intact chloroplasts represented by particles in the range of 4-10 microns for example as observed by Dynamic Light scattering, about 40% w/v of solid content representing 20% of the initial volume introduced in suspension clarification 3C and a high level of protein (e.g. from 45 to 55% dry weight basis). It should be noted that the second chloroplast suspension 3CC may also contain residual antioxidant and/or antimicrobial agent, such as metabisulfite and/or organic acid (such as citric acid), added in the upstream process. The second chloroplast suspension 3CC is, as per its physical, physiological and organic characteristics, similar to the chloroplast suspension 3K obtained after chloroplast separation 3A and may be further processed accordingly.

Referring more particularly to FIG. 10B, a similar second chloroplast suspension 3CC may also be obtained resulting from suspension clarification 3C.2 of the microfiber depleted suspension 2G.2, similar to the microfiber depleted suspension 2G, but obtained from the second pressing 1A.2 when the microfiber depleted suspension 2G is obtained from first pressing 1A.1. This additional second chloroplast suspension 3CC is, per its physical, physiological and organic characteristics similar to chloroplast suspension 3K, and therefore similar to the first second chloroplast suspension 3CC, obtained after suspension clarification 3C.1 and will be further processed accordingly.

As mentioned above, the second fraction resulting from the suspension clarification 3C, i.e. the clarified suspension 3D (as shown in FIGS. 2A, 2B and 5 and 10B) still contains soluble material including more than 50% of the medicagenic acid saponins contained in the microfiber depleted suspension 2G, as well as soluble proteins, sugars, characterized by less than 3, optionally less than 1% w/v of solid content. This clarified suspension 3D is sterile after the removing of microorganisms by suspension clarification 3C. Similarly to the second chloroplast suspension 3CC, the clarified suspension 3D may also contain residual antioxidant and/or antimicrobial agent, such as metabisulfite and/or organic acid (such as citric acid), added in the upstream process.

For example, the process further comprises separating 2A.2 the microfibers from the second macrofiber depleted suspension 1H.2 to obtain a second microfiber depleted suspension 2G.2, clarifying 3C.2 the second microfiber depleted suspension 2G.2, optionally by centrifugation, ultrafiltration and/or tangential flow filtration to obtain a second suspension clarification 3C.2 and combining the second suspension clarification 3CC with the clarified suspension 3D.

For example, the clarifying the chloroplast reduced suspension 3B (or 2G.2) is carried out at a temperature of about 15° C. to about 42° C., about 20° C. to about 40° C., about 20° C. to about 38° C., about 20° C. to about 34° C., about 25° C. to about 35° C., about 30° C. to about 35° C. or about 25° C. to about 34° C. For example, the suspension clarification 3C is carried out at a temperature of about 20° C. to about 40° C. For example, the suspension clarification 3C is carried out at a temperature of about 25° C. to about 35° C. For example, the suspension clarification 3C is carried out at a temperature of about 30° C. to about 35° C.

Compound Extraction 3E and Subsequent Activities

Referring to FIGS. 1, 2A, 2B and 15, a compound extraction 3E can be also carried out from the clarified suspension 3D to obtain high value molecules and/or compounds. These molecules and/or compounds, once extracted, may be purified and/or conditioned to obtain a precursor which can be used as active ingredient for the development of end products useful in various industries.

Figure 15:
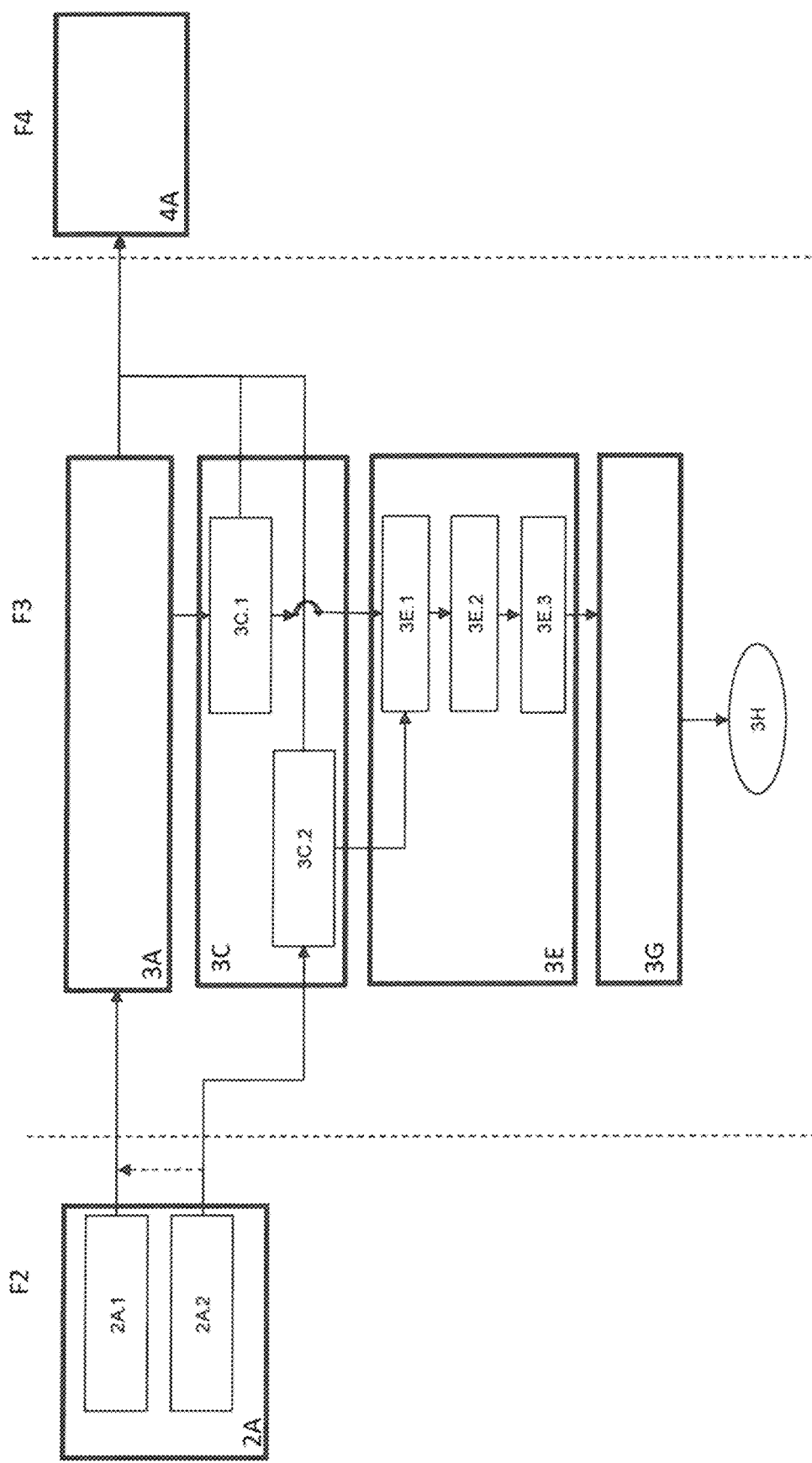
FIG. 15 is a flow sheet diagram of the third fractionation F3, according to an embodiment.

For example, the clarified suspension 3D can be a source of terpene such as saponin. For example, the clarified suspension 3D can be a source of saponin e.g. medicagenic acid sponin, which could be an active ingredient for the development of various types of end products. FIG. 15 illustrates the extraction and the conditioning allowing to obtain a saponin precursor 3H to be used as a basis for the development of various end products. Example 13 details the distribution of medicagenic acid saponins in various fractions. Methods of extracting saponin using solid phase extraction are described in International Patent Application No. PCT/CA2007/001255 entitled MEDICAGENIC ACID SAPONIN AND USES THEREOF, filed Jul. 13, 2007, which is incorporated herein by reference in its entirety.

For example, the clarified suspension 3D or chloroplast reduced suspension 3B is a source of fatty alcohol such as triacontanol, as shown in Example 14.

For example, the clarified suspension 3D can be a source of protein, optionally a protein identified any one of Tables 10 to 16. For example, the clarified suspension 3D can be a source of peptide.

For example, the process for preparing a saponin precursor 3H further comprises mixing the chloroplast reduced composition with an antimicrobial agent and/or an antioxidant, optionally sodium metabisulfite or citric acid.

For example, the extracting the saponin-enriched powder 3F comprises isolating and/or concentrating the saponin content in the chloroplast reduced composition, optionally using high-performance liquid chromatography, distillation and/or spray drying.

For example, the extracting the saponin-enriched powder 3F is carried out at a temperature of about 15° C. to about 42° C., about 20° C. to about 38° C., about 20° C. to about 34° C. or about 25° C. to about 34° C.

For example, the resulting saponin-enriched powder 3F may be conditioned. For example, the conditioning comprises packaging the saponin-enriched powder 3F. For example, the saponin-enriched powder 3F is hermetically sealed, optionally in a receptacle. For example, the receptacle is a polymer pouch or bag, optionally an opaque polymer pouch or bag. For example, the saponin-enriched powder 3F is hermetically sealed under modified atmosphere or inert atmosphere, optionally $N_2$ or nitrogen.

For example, the saponin precursor 3H comprises a saponin content of about 50 mg/g to about 180 mg/g (dry basis). For example, the saponin precursor 3H comprises a saponin content of about 3% to about 6% (dry basis).

For example, the saponin is medicagenic acid saponin.

For example, the saponin precursor 3H herein disclosed may be used in the manufacture of an insecticide, as shown in Example 9. The saponin precursor 3H may also be used in the manufacture of a nutraceutical, a cosmetic product and/or a pharmaceutical agent. For example the saponin precursor 3H is used as an insecticide, a nutraceutical and/or a pharmaceutical agent.

Fourth Fractionation F4

The fourth fractionation F4 is directed to washing chloroplasts in order to condition them into end products (as shown for example in FIGS. 1, 2A, 2B, 6, 7, 8 and 9) and/or to use them as a source of valuable compounds following extraction. The fourth fractionation F4 is represented by process activities (rectangle), intermediary, end and precursor products (oval) and uses (diamond) from 4A to 4N. The fourth fractionation F4 comprises a chloroplast washing 4A, whose purpose is to obtain as much as possible cleaned intact chloroplasts from the chloroplast suspension 3K mainly, but also from the second chloroplast suspension 3CC. To do so different methods may be used to remove residual contaminants such as structures and/or compounds of small size as well as molecules, dissolved therein or not, so as to obtain a washed chloroplast suspension 4B. Afterward, this suspension may undergo a liquid chloroplast conditioning 4G and/or a dry chloroplast conditioning 4D, to obtain a liquid chloroplast composition 4H, and/or a dry chloroplast composition 4E, respectively, both of which may be suitable for human and animal nutrition 4I and 4F. The washed chloroplast suspension 4B may also undergo a compound extraction 4J to generate for example a Rubisco suspension 4K. This suspension may undergo Rubisco conditioning 4L to obtain a Rubisco precursor 4M which can be used for further end product development 4N.

Chloroplast Washing 4A

The different chloroplast suspensions 3K generated by the previous fractionation F3 may still contain some residual materials and can be washed in order for the chloroplasts to be selectively separated from other components, such as volatiles, phenolics and saponins, that are deemed undesirable from a dietary perspective, mainly due to their potential toxicity, off-taste and off-odor. Thus, the chloroplast washing 4A allows to obtain a washed chloroplast suspension 4B ready to undergo chloroplast conditionings 4G and 4D as well as for compound extraction 4J.

Chloroplast separation 3A is limited in its capacity to concentrate clean chloroplasts. In addition, it was discovered that when chloroplasts become too concentrated, their manipulation may create excessive shearing. A solid chloroplast content of about 30-35% may be obtained by centrifugation, tangential flow filtration (TFF) or flocculation/decanting. But, at such concentrations, there remains significant amounts of soluble contaminants in the chloroplast suspension 3K. Similarly, sedimentation of chloroplasts, by centrifugation, will provide a concentrate with 30% of the initial volume of the chloroplast suspensions 3K introduced in the centrifuge and with a 35% solid content.

As chloroplasts in all the different chloroplast suspensions 3K remain substantially intact throughout the earlier fractionations, they can undergo chloroplast washing 4A for further cleaning and concentrating. To do so, the main chloroplast suspensions 3K, the second chloroplast suspension 3CC, and/or the chloroplast suspension 3CC coming from the chloroplast clarification sub-activity related to the second pressing carried out during macrofiber separation 1A (as shown in FIG. 10B), may be diluted in water or osmoticum (with minimum shearing) and sedimented again. The use of either water or osmoticum is guided by the objective of the extent of the washing activity. The average osmotic potential of the macrofiber depleted suspension 1H obtained from pressing the plant fragments 0B is equivalent to about 0.6 M (monovalent salt). This osmotic potential is isotonic for chloroplasts; however, chloroplasts can endure variations between 0.25M-0.7M (equivalent for monovalent salt) for limited amounts of time. Thus, diluting a chloroplast suspension 3K in about 2.5 times its volume in water would bring the osmotic potential to about 0.25M, which is tolerable for chloroplasts. With such a dilution rate, the chloroplast integrity can be maintained which allows retaining within the chloroplasts the Rubisco protein and other valuable chloroplast soluble compounds, which may be further extracted during compound extraction 4J.

Diluting repeatedly in water or diluting in larger volumes of water will bring the chloroplast osmotic potential to a value lower than 0.25M which may cause chloroplast breakage (e.g. due to hypo-osmotic conditions). The larger the volume of water used for dilution (in a single step or in repeated steps), the lower the amount of soluble components will be present (e.g. phenolics, saponins) in the final washed chloroplast suspension 4B. If more extensive washing is required, osmoticum solutions are then used to maintain osmotic potential at higher than 0.25M.

The chloroplast washing 4A also allows the content of the washed chloroplast suspension 4B to be highly reproducible, from one batch to another, removing the undesirable compounds that exist in different concentrations depending of certain variables. In fact, chloroplasts have a content that will vary only slightly (as the relative abundance of its internal components is linked to one major physico-biochemical function). In contrast, the content in soluble low molecular weight components (LMWC) of a leaf cell will vary significantly depending on its physiological status, e.g. due to stress (cold, heat, salt) or developmental status. As soluble LMWC vary, and if significant amounts of soluble components around the chloroplasts are present in the final chloroplast preparation, the composition of this preparation as a final product will vary accordingly, except if appropriate washing occurs to remove LMWC.

After dilution of a given chloroplast suspension 3K, the chloroplast re-separation or concentration can be carried out using various suitable methods such as centrifugation, tangential flow filtration (TFF), flocculation/coagulation and equivalent methods therefor. Similar to the chloroplast separation 3A, the chloroplast washing 4A should be be performed under conditions avoiding excessive shearing, temperature increases, pressure variation, molarity variation and all other conditions that would lead to chloroplast breakage and cause dispersion of soluble components of the chloroplasts in the entire suspension (e.g. washed chloroplast suspension 4B).

In an embodiment, the chloroplast washing 4A may be carried out as follows. A chloroplast suspension 3K, or a mixture of different chloroplast suspensions 3K and 3CC, is diluted to a ratio of about 1:3 (1 volume of chloroplast suspension to 3 final volume) and subsequently separated by centrifugation (e.g. at 10,000G). For example, 300 L of chloroplast suspension 3K will be diluted to 900 L of total final volume with water.

For example, the washing comprises diluting the chloroplast suspension 3K and re-isolating the chloroplasts.

For example, the main chloroplast suspension 3K is diluted at a liquid:chloroplast suspension 3K ratio of about 1 to about 5. For example, the chloroplast suspension 3K is diluted at a liquid:chloroplast suspension 3K ratio of about 1.5 to about 4. For example, the chloroplast suspension 3K is diluted at a liquid:chloroplast suspension 3K ratio of 3. For example, the chloroplast suspension 3K is re-suspended at a liquid:suspension ratio of about 2 to about 3.

For example, the re-suspended chloroplast suspension 3K has a molarity of about 0.2 M to about 0.7 M or about 0.25 M to about 0.6 M. For example, the re-isolating comprises centrifugation, coagulation, flocculation and/or sedimentation of the re-suspended chloroplast composition.

For example, the re-isolating of the chloroplasts from the diluted chloroplast suspension 3K comprises centrifugation, tangential flow filtration (TFF), flocculation/decanting.

For example, the re-isolating from the diluted chloroplast suspension 3K (or mixtures thereof) comprises centrifuging the diluted suspension at a force of about 4,000 g to about 15,000 g. For example, the re-isolating comprises centrifuging the diluted chloroplast suspension 3K involved at a force of about 2,000 g to about 10,000 g. For example, the re-isolating comprises centrifuging the diluted chloroplast suspension 3K involved at a force of about 4,000 g to about 10,000 g. For example, the re-isolating comprises centrifuging the diluted chloroplast suspension 3K at a force of about 10,000 g.

For example, the washing comprises twice re-suspending (or diluting) and re-isolating the chloroplasts from the initial chloroplast suspension 3K.

The washed chloroplast suspension 4B resulting from the chloroplast washing 4A mainly comprises structures, compounds, and molecules of protein and lipid nature, unaltered or slightly altered, suspended or dissolved in a liquid phase. It should be noted that the washed chloroplast suspension 4B may also contain residual antioxidant and/or antimicrobial agent, such as metabisulfite and/or organic acid (such as citric acid), added in the upstream process. The desirable preservation of the original and intrinsic qualities of the elements constituting this product is made possible by the mitigation, at each stage of the upstream process, of chemical, physical, microbiological and biochemical stresses.

Thus, referring now to FIGS. 1, 2A, 2B, 7, 8 and 9, the resulting washed chloroplast suspension 4B may be further processed to condition end products and/or to extract high value molecules and/or compounds for further end product development 4N.

For example, the conditioning (4D or 4G) comprises mixing the chloroplast suspension 3K, optionally the washed chloroplast suspension 4B, with a conservation agent/antioxidant, optionally sodium metabisulfite, an omega-3 fatty acid, an omega-6 fatty acid, vitamins, or mixtures thereof.

The washed chloroplast suspension 4B has a solid content of about 40% (w/w), an intact chloroplast content >90%, at least about 50% of solid particles comprised therein having an average size of about 4 microns to about 10 microns, a protein content of about 50% w/w (dry basis), a lipid content of about 11.5% w/w (dry basis), a Ribulose-1,5-bisphosphate carboxylase/oxygenase (Rubisco) content of about 90% of the chloroplast suspension 3K, an antioxidant content of greater than about 22,000 µmole TE/100 g and a beta-carotene content of greater than about 5 mg/g.

The chloroplast content may be used to measure the integrity and purity of the chloroplasts in the washed chloroplast suspension 4B. To obtain a more precise evaluation of chloroplast integrity, the ratios between specific chloroplast components, for example, the ratio between thylakoid-associated pigments (such as carotene or chlorophyll) and Rubisco (the major stroma protein component), may be used as an indicator. Similarly, the ratios between specific chloroplast components (for example Rubisco, carotene, chlorophyll) and specific cellular (cytosolic) components (for example actin or enzymes of the gluconeogenesis pathway) may be used to measure the purity of the washed chloroplast suspension 4B and to identify impurities. Finally, it should be noted that immunological markers available in commercial kits (for example from Agrisera) may also be used to assess the purity of the washed chloroplast suspension 4B. Such immunological markers may be specific for example for enzymes contained in chloroplast (e.g. Rubisco).

For example, the washed chloroplast suspension 4B, the liquid chloroplast composition 4H and/or the dry chloroplast composition 4E further comprise an antioxidant, an antimicrobial agent, optionally a bacteriostatic or a bactericide, a fungicide, or mixtures thereof.

For example, the washed chloroplast suspension 4B further comprises omega-3 fatty acids (e.g. eicosapentaenoic acid or docosahexaenoic acid), omega-6 fatty acids, vitamins, or mixtures thereof.

For example, the washed chloroplast suspension 4B further comprises one or more organic acid, optionally chosen from citric acid, malic acid, succinic acid, and lactic acid. For example, the organic acid is a mild organic acid, optionally having a pH between 5 and 7.

For example, the washed chloroplast suspension 4B has a moisture content of about 80% to about 90%. For example, the washed chloroplast suspension 4B has a moisture content of about 82% to about 88%. For example, the washed chloroplast suspension 4B has a moisture content of about 84% to about 86%. For example, the washed chloroplast suspension 4B has a moisture content of about 85%.

For example, the washed chloroplast suspension 4B has a dry matter content of about 15%.

For example, the washed chloroplast suspension 4B has a pH of less than about 5.0. For example, the washed chloroplast suspension 4B has a pH of less than about 4.8. For example, the washed chloroplast suspension 4B has a pH of less than about 4.7. For example, the washed chloroplast suspension 4B has a pH of less than about 4.6. For example, the suspension has a pH of less than about 4.5. For example, the washed chloroplast suspension 4B has a pH of less than about 4.4. For example, the washed chloroplast suspension 4B has a pH of less than about 4.3. For example, the washed chloroplast suspension 4B has a pH of less than about 4.2.

For example, the washed chloroplast suspension 4B has a solid content of about 25% w/v to about 50% w/v. For example, the washed chloroplast suspension 4B has a solid content of about 25% w/v to about 45% w/v. For example, the washed chloroplast suspension 4B has a solid content of about 30% w/v to about 45% w/v. For example, the washed chloroplast suspension 4B has a solid content of about 35% w/v to about 40% w/v. For example, the washed chloroplast suspension 4B has a solid content of about 30 wt. % to about 50 wt. %, about 35 wt. % to about 45 wt. %, about 37 wt. % to about 43 wt. % or about 39 wt. % to about 51 wt. %.

For example, the washed chloroplast suspension 4B has a high proportion of intact chloroplast over total solids present, for example has a chloroplast content over total solids present of at least about 50% w/w to about 99% w/w (dry basis). For example, the washed chloroplast suspension 4B has a chloroplast content of at least about 60% w/w to about 99% w/w (dry basis). For example, the washed chloroplast suspension 4B has a chloroplast content of at least about 70% w/w to about 99% w/w (dry basis). For example, the washed chloroplast suspension 4B has a chloroplast content of at least about 75% w/w to about 99% w/w (dry basis). For example, the washed chloroplast suspension 4B has a content of at least about 75% w/w to about 97.5% w/w (dry basis). For example, wherein at least about 40 wt. % to about 90 wt. %, at least about 50 wt. % to about 90 wt. %, at least about 60 wt. % to about 90 wt. %, at least about 70 wt. % to about 90 wt. % or at least about 75 wt. % to about 90 wt. % of the solid content consists of chloroplasts.

For example, at least about 95% of solid particles comprised in the washed chloroplast suspension 4B have an average size of about 3 microns to about 10 microns. For example, at least about 90% of solid particles comprised in the washed chloroplast suspension 4B have an average size of about 4 microns to about 10 microns. For example, at least about 80% of solid particles comprised in the washed chloroplast suspension 4B have an average size of about 4 microns to about 6 microns. For example, at least about 75% of solid particles comprised in the washed chloroplast suspension 4B have an average size of about 4 microns to about 5 microns. For example, at least about 90% of solid particles comprised in the washed chloroplast suspension 4B have an average size of about 3 microns to about 5 microns. For example, at least about 50%, about 60%, about 70%, about 80% or about 90% of solid particles comprised in the composition have an average size of about 5 microns to about 10 microns.

For example, at least about 70% of the chloroplasts are intact chloroplasts e.g. as determined by dynamic light scattering measurement and analysis. For example, at least about 75% of the chloroplasts are intact chloroplasts e.g. as determined by dynamic light scattering measurement and analysis. For example, at least about 80% of the chloroplasts are intact chloroplasts. For example, at least about 85% of the chloroplasts are intact chloroplasts. For example, at least about 90% of the chloroplasts are intact chloroplasts. For example, at least about 95% of the chloroplasts are intact chloroplasts.

For example, at least about 50%, about 60%, about 70%, about 80% or about 90% of the chloroplasts have a preserved outer membrane integrity. For example, at least about 50%, about 60%, about 70%, about 80% or about 90% of the chloroplasts have a preserved inner membrane integrity. For example, at least about 50%, about 60%, about 70%, about 80% or about 90% of the chloroplasts have maintained metabolic activity as compared to chloroplasts comprised in a reference Fabaceae family plant.

For example, the washed chloroplast suspension 4B has a protein content greater than 45% w/w (dry basis). For example, the washed chloroplast suspension 4B has a protein content of about 45% w/w to about 55% w/w (dry basis). For example, the washed chloroplast suspension 4B has a protein content of about 48% w/w to about 55% w/w (dry basis). For example, the washed chloroplast suspension 4B has a protein content of about 48% w/w to about 53% w/w (dry basis).

For example, the washed chloroplast suspension 4B has a Rubisco content of about 90% of the Rubisco content in the chloroplast suspension 3K.

For example, the washed chloroplast suspension 4B has a lipid content of about 5% w/w to about 25% w/w (dry basis). For example, the washed chloroplast suspension 4B has a lipid content of about 10% w/w to about 25% w/w (dry basis). For example, the washed chloroplast suspension 4B has a lipid content of about 10% w/w to about 20% w/w (dry basis).

For example, the washed chloroplast suspension 4B has a lipid/protein ratio of about 0.2 to 0.4.

For example, the washed chloroplast suspension 4B has an omega-3 fatty acid content, optionally an eicosapentaenoic acid and/or a docosahexaenoic acid content, of greater than about 1% w/w (dry basis) or greater than about 2% w/w (dry basis). For example, the washed chloroplast suspension 4B has an omega-3 fatty acid content of about 2% w/w to about 10% w/w (dry basis). For example, the washed chloroplast suspension 4B has an omega-3 fatty acid content of about 2% w/w to about 6% w/w (dry basis).

For example, the washed chloroplast suspension 4B has an omega-6 fatty acid content of greater than about 1% w/w (dry basis). For example, the washed chloroplast suspension 4B has an omega-6 fatty acid content of about 1% w/w to about 10% w/w (dry basis). For example, the washed chloroplast suspension 4B has an omega-6 fatty acid content of about 1% w/w to about 4% w/w (dry basis).

For example, the washed chloroplast suspension 4B has an omega-3 fatty acid/omega-6 fatty acid ratio of about 1.5 to about 3.

For example, the washed chloroplast suspension 4B has a natural antioxidant content of greater than about 20,000 µmole TE/100 g. For example, the washed chloroplast suspension 4B has a natural antioxidant content of about 20,000 µmole TE/100 g to about 24,000 000 µmole TE/100 g.

For example, the washed chloroplast suspension 4B has a chlorophyll content of greater than about 20 mg/g (dry basis), greater than about 25 mg/g or greater than about 30 mg/g (dry basis).

For example, the washed chloroplast suspension 4B has a beta-carotene content of greater than about 5.0 mg/g (dry basis). For example, the washed chloroplast suspension 4B has a beta-carotene content of greater than about 300,000 IU/100 g.

For example, the washed chloroplast suspension 4B has a xanthophyll lutein content of greater than about 1.6 mg/g (dry basis).

For example, the washed chloroplast suspension 4B has a saponin content 10 to about 15% (dry basis) relative to the original saponin content in the plant fragments 0B or to a reference *Medicago* spp plant.

For example, the washed chloroplast suspension 4B has a medicagenic acid acid content of less than about 3.0 mg/g (dry basis).

Dry Chloroplast Conditioning 4D

The washed chloroplast suspension 4B, resulting from the chloroplast washing 4A, may be dried to preserve the qualities of its constituents and even to increase them. The washed chloroplast suspension 4B is smoothly dried to decrease the total moisture content and thus reduce the oxidation and the water activity (aw). The drying is carried out by spray drying, drum drying, freeze-drying, atomization, fluidized bed or other methods equivalent therefor. The preferable drying temperature is 45° C. or less. The resulting dry chloroplast composition 4E has a chloroplast content of at least 75%, a moisture content of less than about 12% and a water activity (aw) lower than 1. According to the needs and prior to the packaging, the dry chloroplast composition 4E can be mixed with a formulation agent (e.g. a thickening agent, a dispersing agent, a gelling agent, a thinning agent or others), a conservation agent, a nutritional supplement and/or beneficial microorganism. The packaging to protect the final dry chloroplast composition 4E is selected according to the preservation, transport or client requirements.

Unlike the dry chloroplast composition 4E herein disclosed, other known existing green protein/pigment products, for example sold in pellets, are produced by coagulation at high temperatures and alkalinization or acidification of the liquid obtained after a high pressure mechanical extraction. This process destroys the chloroplast integrity and releases Rubisco in the soluble fraction. Such products also contain contaminants from the soluble fraction that coagulate with fragmented chloroplast components. They are also heated during the pelleting step. Dried alfalfa juices are produced through pressing and spray-drying with the use of carriers. Thus, they may contain undesirable components of the soluble fraction diluting the positive value of some ingredients.

For example, the conditioning may comprise granulating and/or encapsulating the dry chloroplast composition. For example, encapsulating can be achieved using known methods. For example, the dry chloroplast composition 4E may be mixed with suitable food grade binder, lubricant, antioxidant etc. to form a mixture. The mixture may be granulated in the form of granules and the granules may be encapsulated in capsules, optionally opaque/light-impermeable capsules. Optionally, the capsule is made of food grade materials. In other embodiments, the mixture forms a suspension and the suspension can be directly encapsulated, optionally in opaque/light-impermeable capsules.

In an embodiment, the washed chloroplast suspension 4B is dried by air using 2 spray dryers which can operate 24 h. The drying temperature is set at 45° C. or less and allows reducing moisture level from about 85% to about 6-10%. A resulting dry chloroplast composition 4E having a bright green color is ready for use as a chloroplast concentrate.

For example, the conditioning comprises mixing the chloroplast suspension 3K, optionally the washed chloroplast suspension 4B, with a conservation agent/antioxidant, optionally sodium metabisulfite, an omega-3 fatty acid, an omega-6 fatty acid, vitamins, or mixtures thereof.

For example, wherein the conditioning comprises drying the washed chloroplast suspension 4B at a temperature of 45° C. or less. For example, the conditioning comprises drying the washed chloroplast suspension 4B at a temperature between 20° C. and 44° C.

For example, the drying is carried out using spray drying, drum drying, freeze-drying, atomization or a fluidized bed.

For example, the conditioning comprises mixing the chloroplast composition with a formulating agent (e.g. a thickening agent, a dispersing agent, a gelling agent, a thinning agent), a conservation agent, a food supplement, an omega-3 fatty acid (e.g. eicosapentaenoic acid or docosahexaenoic acid), an omega-6 fatty acid, or mixtures thereof.

For example, the composition may be packaged in a 5 kg bag to 20 kg sealed pail, under nitrogen blanket and provide a shelf life of several years.

For example, the conditioning comprises packaging the chloroplast composition under modified atmosphere or inert atmosphere, optionally $N_2$ or nitrogen.

For example, conditioning comprises packaging the chloroplast composition in a polymer pouch or bag, optionally an opaque polymer pouch or bag.

For example, conditioning comprises granulating the chloroplast composition. For example, conditioning comprises encapsulating the chloroplast composition in a capsule, optionally an opaque capsule. For example, conditioning comprises granulating and encapsulating the chloroplast composition.

In an embodiment, there are provided dry chloroplast composition 4E produced from Fabaceae family plant obtained according to the process herein disclosed. For example, the plant is from the *Medicago* genus. For example, the plant is from the *Medicago sativa* specie or subspecies.

For example, the dry chloroplast composition 4E has a moisture content of less than about 4%, less than about 3%, less than about 2% or less than about 1%.

For example, the dry chloroplast composition 4E is in powder form. For example, the dry chloroplast composition 4E is in granular form.

For example, the dry chloroplast composition 4E is in encapsulated form. For example, the composition is encapsulated in a capsule, optionally an opaque capsule.

For example, a nutritional supplement e.g. vitamins, omega-3 fatty acid (e.g. eicosapentaenoic acid or docosahexaenoic acid), an omega-6 fatty acid, or mixtures thereof may be added to the dry chloroplast composition 4E.

For example, the dry chloroplast composition 4E further comprises an antioxidant, an antimicrobial agent, optionally a bacteriostatic or a bactericide, a fungicide, or mixtures thereof. For example, the antioxidant and/or the antimicrobial agent is citric acid, metabisulfite, benzoate, optionally sodium metabisulfite, potassium metabisulfite, sodium benzoate or potassium benzoate.

For example, the dry chloroplast composition 4E further comprises omega-3 fatty acids (e.g. eicosapentaenoic acid or docosahexaenoic acid), omega-6 fatty acids, vitamins, or mixtures thereof.

For example, at least about 40 wt. % to about 90 wt. %, at least about 50 wt. % to about 90 wt. %, at least about 60 wt. % to about 90 wt. %, at least about 70 wt. % to about 90 wt. % or at least about 75 wt. % to about 90 wt. % of the solid content consists of chloroplasts.

For example, at least about 50%, about 60%, about 70%, about 80% or about 90% of solid particles comprised in the dry chloroplast composition 4E have an average size of about 5 microns to about 10 microns.

For example, at least about 50%, about 60%, about 70%, about 80% or about 90% of the chloroplasts have a preserved inner membrane integrity. For example, at least about 50%, about 60%, about 70%, about 80% or about 90% of the chloroplasts have a preserved outer membrane integrity.

For example, at least about 50%, about 60%, about 70%, about 80% or about 90% of the chloroplasts have maintained metabolic activity as compared to chloroplasts comprised in a reference Fabaceae family plant.

For example, the dry chloroplast composition 4E has a protein content of about 45 wt. % to about 55 wt. %, about 48 wt. % to about 55 wt. % or about 48 wt. % to about 52 wt. %.

For example, the dry chloroplast composition 4E has a Rubisco content of about 90% of the Rubisco content in the chloroplast suspension 3K.

For example, the dry chloroplast composition 4E has a beta-carotene content of greater than about 300,000 IU/100 g. For example, the composition has a chlorophyll content of greater than about 20 mg/g, greater than about 25 mg/g or greater than about 30 mg/g. For example, the composition has a xanthophyll lutein content of greater than about 1.6 mg/g.

For example, the dry chloroplast composition 4E has a natural antioxidant content of greater than about 20,000 µmole TE/100 g. For example, the composition has a natural antioxidant content of about 20,000 000 µmole TE/100 g to about 24,000 000 µmole TE/100 g.

For example, the dry chloroplast composition 4E has a lipid content of about 5 wt. % to about 15 wt. %, about 10 wt. % to about 15 wt. % or about 10 wt. % to about 12 wt. %.

For example, the dry chloroplast composition 4E has an omega-3 fatty acid content, optionally an eicosapentaenoic acid and/or a docosahexaenoic acid content, of greater than about 2 wt. %. For example, the composition has an omega-3 fatty acid content of about 2 wt. % to about 10 wt. % or about 2 wt. % to about 6 wt. %.

For example, the dry chloroplast composition 4E has an omega-6 fatty acid content of greater than about 1%. For example, the composition has an omega-6 fatty acid content of about 1% to about 10% or about 1% to about 4%. For example, the composition has an omega-3 fatty acid/omega-6 fatty acid ratio of about 1.5 to about 3.

For example, the dry chloroplast composition 4E has a lipid/protein ratio of about 0.2 to about 0.4.

For example, the dry chloroplast composition 4E has a pH of less than about 5.0, less than about 4.8, less than about 4.7, less than about 4.6, less than about 4.5, less than about 4.4, less than about 4.3 or less than about 4.2.

Considering the content of the dry chloroplast composition 4E, it can be beneficially used for human and animal nutrition 4F. Table 7 below provides an example of the main characteristics that can be obtained compared with those of other products existing in the market.

In an aspect, there is provided a use of the dry chloroplast composition 4E herein disclosed, for feeding marine organisms.

In an aspect, there is provided a use of the dry chloroplast composition 4E herein disclosed, in the manufacture of food for animals or humans. In an aspect, there is provided a use of the dry chloroplast composition 4E herein disclosed, as food for animals or humans.

In an aspect, there is provided a use of the dry chloroplast composition 4E herein disclosed, in the manufacture of a nutritional supplement.

In an aspect, there is provided a use of the dry chloroplast composition 4E herein disclosed, in the manufacture of a cosmetic product.

In an aspect, there is provided a method for feeding marine organisms, said method comprising replacing at least a portion of microalgae provided in a diet for said marine organisms by the rehydrated dry chloroplast composition 4E herein disclosed.

Liquid Chloroplast Conditioning 4G

The washed chloroplast suspension 4B, resulting from the chloroplast washing 4A, may also undergo a liquid conditioning 4G to provide in specific markets a liquid chloroplast composition 4H as end product. The liquid chloroplast composition 4H can be the washed chloroplast suspension 4B used as such without further modification or diluted in water or other liquids compatible with the final uses targeted and ensuring the integrity of the chloroplasts. When used as such without further modification, the resulting liquid chloroplast composition 4H presents a moisture content of about 85% which corresponds to that of the washed chloroplast suspension 4B. According to the needs and prior to the packaging, the liquid chloroplast composition 4H can be mixed with a formulation agent (e.g. a thickening agent, a dispersing agent, a gelling agent, a thinning agent or others), a conservation agent, a nutritional supplement and/or beneficial microorganism. The resulting composition should present a molarity ensuring the integrity of the chloroplasts which is close to 0.25-0.7 M. Finally, the packaging to protect the final liquid chloroplast composition 4H is selected according to the preservation, transport or client requirements.

Similarly to the dry chloroplast conditioning 4D, the liquid chloroplast conditioning 4G may also comprise encapsulating the chloroplasts in a capsule, optionally an opaque capsule. Encapsulating the compositions herein disclosed can be achieved using known methods. To have a liquid end product the resulting capsules are then resuspended in a liquid compatible with the final uses.

For example, the conditioning comprises mixing the chloroplast suspension, optionally the washed chloroplast suspension 4B, with a conservation agent/antioxidant, optionally sodium metabisulfite, an omega-3 fatty acid, an omega-6 fatty acid, vitamins, or mixtures thereof.

For example, the conditioning comprises adjusting the salinity and/or molarity of the chloroplast suspension. For example, the salinity of the chloroplast suspension is adjusted to about 2% to about 4%, optionally to about 3.5%.

For example, the molarity of the chloroplast suspension is adjusted to about 0.25M to about 0.7M, optionally to about 0.6M.

For example, the conditioning comprises mixing the chloroplast suspension with a formulating agent (e.g. a thickening agent, a dispersing agent, a gelling agent, a thinning agent), a conservation agent, a food supplement, an omega-3 fatty acid (e.g. eicosapentaenoic acid or docosahexaenoic acid), an omega-6 fatty acid, or mixtures thereof.

For example, the conditioning comprises packaging the chloroplast suspension under modified atmosphere or inert atmosphere, optionally $N_2$ or nitrogen.

For example, the conditioning comprises packaging the chloroplast suspension in a polymer pouch or bag, optionally an opaque polymer pouch or bag.

For example, the conditioning comprises encapsulating the chloroplast suspension in a capsule, optionally an opaque capsule.

In an embodiment, there is provided a liquid chloroplast composition 4H produced from Fabaceae family plant obtained according to the process herein disclosed. For example, the plant is from the *Medicago* genus. For example, the plant is from the *Medicago sativa* specie or subspecies.

In an embodiment, there is provided a liquid chloroplast composition 4H, comprising chloroplasts suspended in water obtained according to the process herein disclosed.

For example, the process further comprises encapsulating the Liquid chloroplast composition 4H in water in a capsule, optionally an opaque capsule.

For example, the water is saline water.

For example, the liquid chloroplast composition 4H has a dry matter content of at least 15 w/w %.

For example, the liquid chloroplast composition 4H further comprises an antioxidant, an antimicrobial agent, optionally a bacteriostatic or a bactericide, a fungicide, or mixtures thereof. For example, the composition further comprises an antioxidant and/or an antimicrobial agent. For example the antioxidant and/or the antimicrobial agent is citric acid, metabisulfite, benzoate, optionally sodium metabisulfite, potassium metabisulfite, sodium benzoate or potassium benzoate.

For example, the liquid chloroplast composition 4H further comprises omega-3 fatty acids (e.g. eicosapentaenoic acid or docosahexaenoic acid), omega-6 fatty acids, vitamins, or mixtures thereof.

For example, the liquid chloroplast composition 4H has a solid content of about 30 wt. % to about 50 wt. %, about 35 wt. % to about 45 wt. %, about 37 wt. % to about 43 wt. % or about 39 wt. % to about 51 wt. %.

For example, at least about 40 wt. % to about 90 wt. %, at least about 50 wt. % to about 90 wt. %, at least about 60 wt. % to about 90 wt. %, at least about 70 wt. % to about 90 wt. % or at least about 75 wt. % to about 90 wt. % of the solid content consists of chloroplasts.

For example, at least about 50%, about 60%, about 70%, about 80% or about 90% of solid particles comprised in the liquid chloroplast composition 4H have an average size of about 5 microns to about 10 microns.

For example, at least about 50%, about 60%, about 70%, about 80% or about 90% of the chloroplasts have a preserved outer membrane integrity. For example, at least about 50%, about 60%, about 70%, about 80% or about 90% of the chloroplasts have a preserved inner membrane integrity.

For example, at least about 50%, about 60%, about 70%, about 80% or about 90% of the chloroplasts have maintained metabolic activity as compared to chloroplasts comprised in a reference Fabaceae family plant. For example, at least about 50%, at least about 60%, at least about 70% or at least about 80% of the chloroplasts are intact chloroplasts e.g. as determined by dynamic light scattering measurement and analysis.

For example, the liquid chloroplast composition 4H has a protein content greater than 45 wt. %. For example, the liquid chloroplast composition 4H has a protein content of about 45 wt. % to about 55 wt. %, about 48 wt. % to about 55 wt. % or about 48 wt. % to about 52 wt. %.

For example, the liquid chloroplast composition 4H has a Rubisco content of about 90% of the Rubisco content in the chloroplast suspension 3K.

For example, the liquid chloroplast composition 4H has a beta-carotene content of greater than about 300,000 IU/100 g. For example, the liquid chloroplast composition 4H has a chlorophyll content of greater than about 20 mg/g, greater than about 25 mg/g or greater than about 30 mg/g. For example, the liquid chloroplast composition 4H has a xanthophyll lutein content of greater than about 1.6 mg/g.

For example, the liquid chloroplast composition 4H has a natural antioxidant content of greater than about 20,000 µmole TE/100 g. For example, the liquid chloroplast composition 4H has a natural antioxidant content of about 20,000 000 µmole TE/100 g to about 24,000 000 µmole TE/100 g.

For example, the liquid chloroplast composition 4H has a lipid content of about 5 wt. % to about 15 wt. %, about 10 wt. % to about 15 wt. % or about 10 wt. % to about 12 wt. %.

For example, the liquid chloroplast composition 4H has an omega-3 fatty acid content, optionally an eicosapentaenoic acid and/or a docosahexaenoic acid content, of greater than about 2 wt. %. For example, the liquid chloroplast composition 4H has an omega-3 fatty acid content of about 2 wt. % to about 10 wt. % or about 2 wt. % to about 6 wt. %.

For example, the liquid chloroplast composition 4H has an omega-6 fatty acid content of greater than about 1%. For example, the liquid chloroplast composition 4H has an omega-6 fatty acid content of about 1% to about 10% or about 1% to about 4%.

For example, the liquid chloroplast composition 4H has an omega-3 fatty acid/omega-6 fatty acid ratio of about 1.5 to about 3.

For example, the liquid chloroplast composition 4H has a lipid/protein ratio of about 0.2 to about 0.4.

For example, the liquid chloroplast composition 4H has a moisture content of about 80% to about 90%, about 82% to about 88%, about 84% to about 86% or about 85%.

For example, the liquid chloroplast composition 4H has a dry matter content of about 15%.

For example, the liquid chloroplast composition 4H has a pH of less than about 5.0, less than about 4.8, less than about 4.7, less than about 4.6, less than about 4.5, less than about 4.4, less than about 4.3 or less than about 4.2.

For example, the liquid chloroplast composition 4H has a protein content greater than 50 wt. % and a chlorophyll content greater than about 25 mg/g, wherein at least 75% of the chloroplasts are intact chloroplasts e.g. as determined by dynamic light scattering measurement and analysis.

For example, the liquid chloroplast composition 4H has a molarity of about 0.2 M to about 0.7 M or about 0.25 M to about 0.7 M.

For example, the liquid chloroplast composition 4H is encapsulated in a capsule, optionally an opaque capsule.

For example, the salinity of the liquid chloroplast composition 4H is adjusted to about 3% to about 4%. For example, the salinity of the liquid chloroplast composition 4H is adjusted to about 3.5%. For example, the molarity of the liquid chloroplast composition 4H is adjusted to about 0.5M to about 0.7M. For example, the molarity of the liquid chloroplast composition 4H is adjusted to about 0.6M.

Considering that the content of the liquid chloroplast composition 4H is similar to that of the dry chloroplast composition 4E, the liquid end products resulting from the process can also be beneficially used for human and animal nutrition 4I.

In an embodiment, the use of the liquid chloroplast composition 4H isolated from fabaceae family plants herein disclosed is for the manufacture of food for animals or humans.

In another embodiment, the use of liquid chloroplast composition 4H isolated from fabaceae family plants is for feeding marine organisms.

In another embodiment, the use of liquid chloroplast composition 4H isolated from fabaceae family plants in the manufacture of a cosmetic product.

Use of chloroplasts isolated from fabaceae family plants in the manufacture of an aqueous suspension in water.

Use of chloroplasts isolated from fabaceae family plants as a replacement or alternative to microalgeae and/or cyanobacteria in a human or animal diet.

For example, the microalgae is *chlorella*. For example, the cyanobacteria is *spirulina*.

A method for feeding marine organisms, said method comprising replacing at least a portion of microalgae and/or cyanobacteria provided in a diet for said marine organisms by the liquid chloroplast composition 4H described herein.

In a further embodiment, the use of chloroplasts isolated from Fabaceae family plants is for the manufacture of an aqueous suspension in water as liquid chloroplast composition 4H ready to use.

In another embodiment, the use of liquid chloroplast composition 4H isolated from fabaceae family plants is for a replacement or alternative to *Spirulina, Chlorella* and/or other micro algea or cyanobacteria in a human or animal diet.

In an embodiment, there is provided a method for feeding marine organisms, said method comprising replacing at least a portion of microalgae provided in a diet for said marine organisms by liquid chloroplast composition 4H isolated from a plant of fabaceae family plant.

Compound Extraction 4J and Subsequent Activities

Referring to FIGS. 1, 2A, 2B, 9 and 16, a compound extraction 4J can be also carried out from the washed chloroplast suspension 4B to obtain high value molecules and/or compounds. These molecules and/or compounds, once extracted, could be purified at different levels and/or conditioned to obtain a precursor which can be used as active ingredient for the development of end products dedicated to various industries or can be considered as an end product in itself depending the commercial context.

For example, the washed chloroplast suspension 4B can be a source of protein, optionally a protein identified any one of Tables 10 to 16. For example, the washed chloroplast suspension 4B can be a source of peptide.

For example, the washed chloroplast suspension 4B can be a source of enzyme such as Rubisco.

Figure 16:
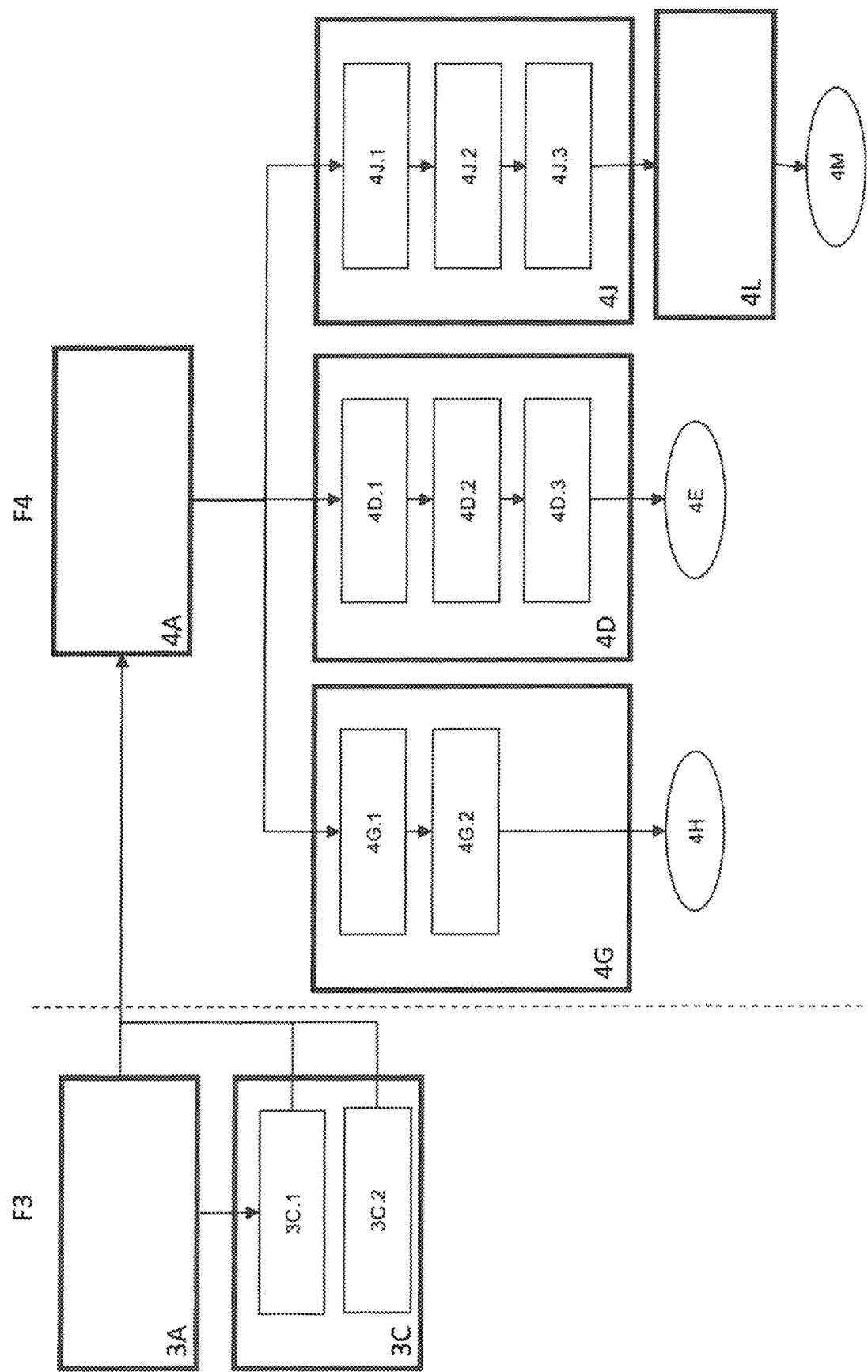
FIG. 16 is a flow sheet diagram of the fourth fractionation F4, according to an embodiment.

For example, the washed chloroplast suspension 4B can be a source of Rubisco which could be an active ingredient for the development of various types of end products. FIG. 16 illustrates the extraction and the conditioning allowing to obtain a Rubisco precursor 4M to be used as a basis for the development of various end products.

For example, the separating the Rubisco from the chloroplasts is carried out at a temperature of less than about 34° C.

For example, the separating the Rubisco from the chloroplasts comprises fractioning the chloroplasts to solubilize the Rubisco and isolating the soluble Rubisco. For example, the solubilizing the Rubisco comprises rupturing the outer and/or inner chloroplast membranes to release the Rubisco, optionally via osmotic shock and/or sonication.

For example, the isolating the soluble Rubisco comprises filtering out insoluble chloroplast components (e.g. thykaloid membranes), optionally using tangential flow filtration at 0.2 microns porosity. For example, the filtering the Rubisco suspension 4K is carried out using tangential flow filtration, filtration, flocculating and/or decanting. For example, the filtering the Rubisco suspension 4K comprises twice filtering the Rubisco suspension 4K.

For example, the conditioning comprises adding to the Rubisco suspension 4K a food grade protective agent, optionally metabisulfite or benzoate and/or one or more complementary ingredient.

For example, the conditioning comprises drying the Rubisco suspension 4K, optionally using spray drying, drum drying, freeze-drying, atomization or a fluidized bed. For example, the drying the temperature is maintained at or below 45° C., optionally between 15° C. and 40° C. or between 20° C. and 35° C.

Valorization of Biomass

Numerous plants can display a content rich in desirable compounds, whether they may be useful in nutritional, medical or industrial applications. By their presence of amino acids or peptides, many of these compounds can be protein compounds and as such their intrinsic qualities may be readily altered by modifying their chemical, physical and/or microbial environments. The presently disclosed process relates to sequential fractionation of plant biomass. Four distinct fractions may be obtained and various structures, compounds or molecules that are desirable may be further isolated and conditioned.

- The first fraction i.e. the first solid fraction can comprise mostly large fibers and structures (e.g. macro fibers).
- The second fraction i.e. the second solid fraction can comprise mostly fibers of small size (e.g. microfibers).
- The third fraction can comprise mostly compounds and molecules (e.g. saponin precursor 3H) that are low in protein, whether in suspension or dissolved in a liquid phase.
- The fourth fraction can comprise mostly proteic or peptidic structures, compounds and molecules, unaltered or slightly altered (e.g. dry chloroplast, liquid chloroplast, Rubisco precursor), in suspension or dissolved in the liquid phase.

Figure 10A:
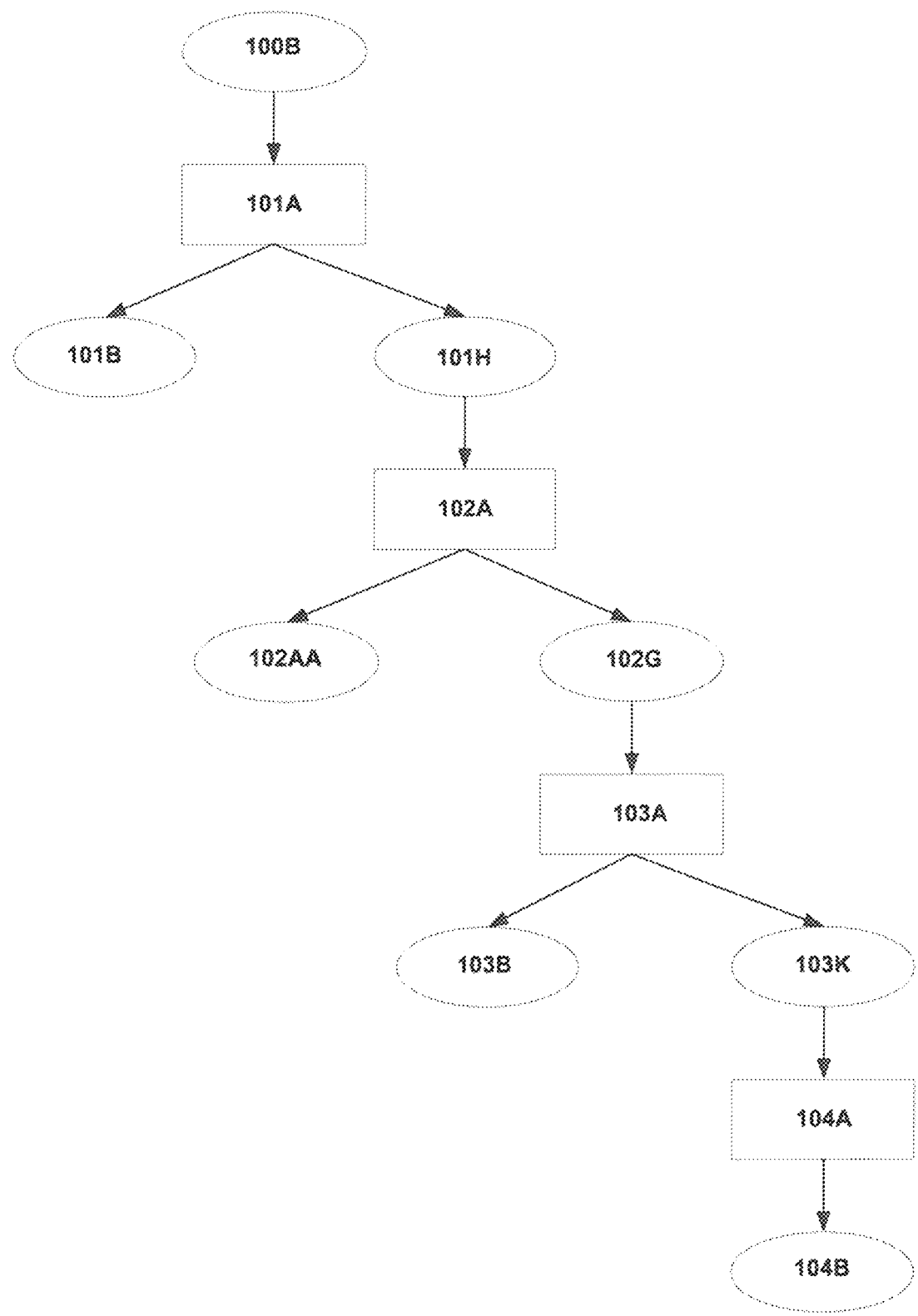
FIG. 10A is a mainstream flow sheet diagram of a process of recovering plant components according another embodiment.
Figure 10B:
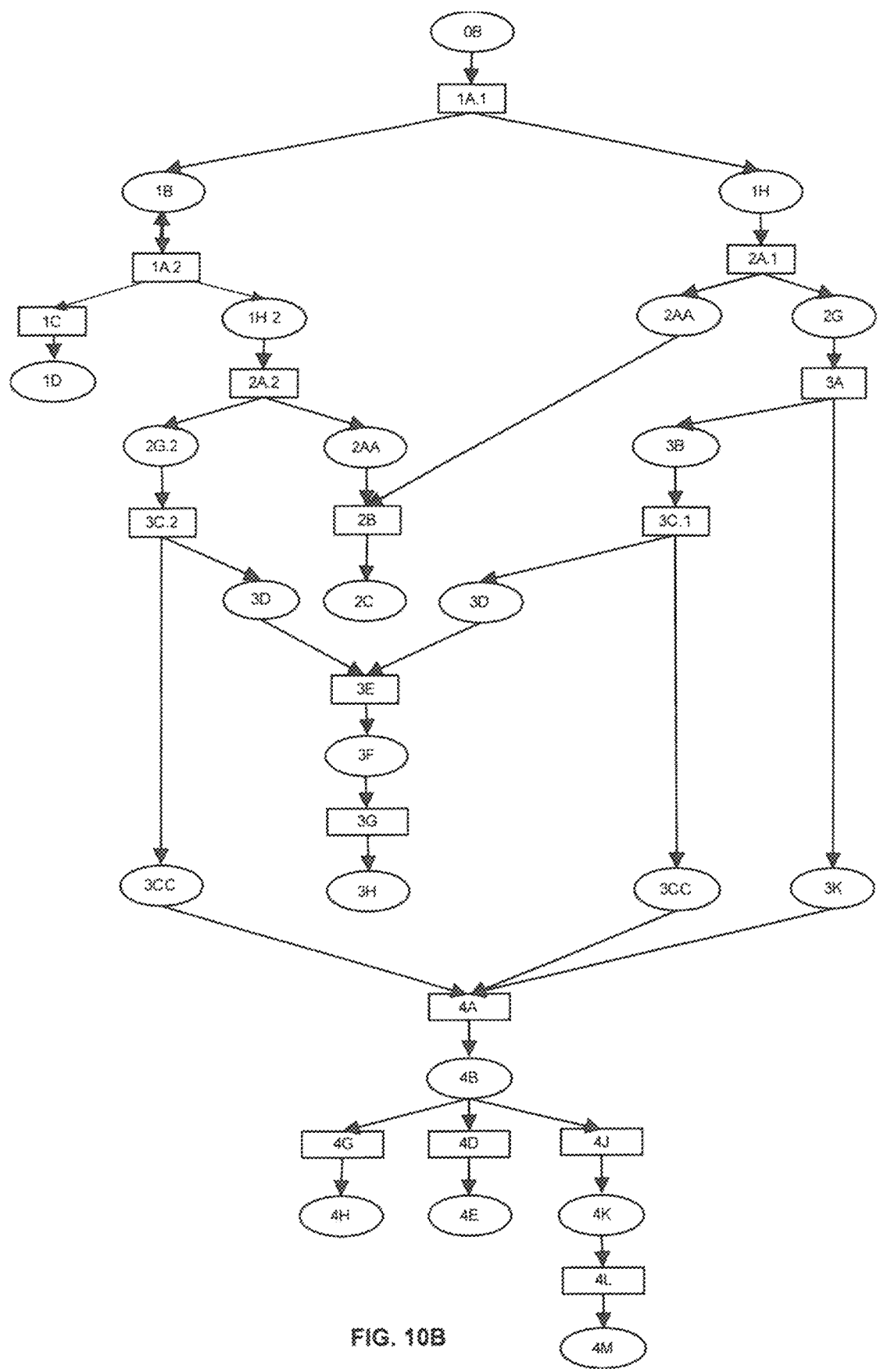
FIG. 10B is a comprehensive flow sheet diagram of a recovering plant components according another embodiment.

Preserving the original and intrinsic qualities of the compounds contained in the above-mentioned fractions presents is economically desirable. This process can be achieved by mitigating, at each of the activities, chemical, physical and microbial stresses, including:

- mitigating shearing forces during the biomass separation of fibers and structures having a size greater than 4 microns, and using equipment dissipating low amounts of energy throughout the process activities;
- maintaining low temperature conditions e.g. 45° C. or less;
- maintaining pH conditions above 4; and
- adding at specific points in the process antioxidant and/or antimicrobial agents Accordingly, a process of recovering plant components (mainstream) is described in FIG. 10A (where process activities are indicated by rectangles and products are indicated by ovals). Specifically, plant fragments 100B undergo an extraction 101A whereby a first solid fraction 101B containing fibers and a first liquid fraction 101H are obtained. The first liquid fraction 101H undergoes a second extraction 102A to obtain a second solid fraction 102AA containing microfibers and a second liquid fraction 102G. The second liquid fraction 102G undergoes a third extraction 103A to obtain a chloroplast depleted fraction 103B and a protein-enriched fraction 103K. In some embodiments, an antioxidant and/or an antimicrobial agent is added to the first solid fraction 101B, the second solid fraction 102AA, the protein-depleted fraction 103B or the protein-enriched fraction 103K.

The process comprises at least one of the following: 1) extracting from the plant or fragment thereof using a pressure of less than about 800 kPa (optionally 600 kPa); 2) maintaining during the process a temperature at or below 45° C. (optionally 37° C.); or 3) extracting from the second liquid fraction while maintaining a pH above about 4.5 (optionally above 4.8).

For example, the process comprises extracting from the plant or fragment thereof using a pressure of less than about 800 kPa (optionally 600 kPa); maintaining during the process a temperature below about 43° C. (optionally 37° C.); and extracting from the second liquid fraction while maintaining a pH above about 4.5 (optionally above 4.8).

In contrast to FIG. 10A which presents the main process activities, FIG. 10B presents a comprehensive view of the detailed fractionation process including intermediate, precursor and end products as well as fractionation process activities and sub-activities. Each and every process activity has to respect physical, chemical and biological conditions in order to obtain a high quality end product.

For example, the process is a continuous process or a semi-continuous process. For example, the process is continuous and the amount of plant fragments used is greater than about 50 metric tons/hour.

In some embodiments, in a process of preparing a chloroplast suspension of the present disclosure, at least 75% or about 75% to about 95% of non-chloroplast cellular content can be removed from the microfiber depleted suspension. For example, at least 75%, at lest 80%, at least 85%, at least 90%, or at least 95% of non-chloroplast cellular content is removed from the microfiber depleted suspension. In some embodiments, in a process of preparing a chloroplast suspension of the present disclosure, substantially all of non-chloroplast cellular content can be removed from the microfiber depleted suspension.

In some embodiments, in a process of preparing a chloroplast suspension of the present disclosure, at least 75% or about 75% to about 95% of soluble content outside of chloroplast can be removed from the microfiber depleted suspension. For example, at least 75%, at lest 80%, at least 85%, at least 90%, or at least 95% of soluble content outside of chloroplast is removed from the microfiber depleted suspension. In some embodiments, in a process of preparing a chloroplast suspension of the present disclosure, substantially all of soluble content outside of chloroplast can be removed from the microfiber depleted suspension.

In some embodiments, in a process of preparing a liquid chloroplast composition of the present disclosure, at least 75% or about 75% to about 95% of non-chloroplast cellular content can be removed from the microfiber depleted suspension. For example, at least 75%, at lest 80%, at least 85%, at least 90%, or at least 95% of non-chloroplast cellular content is removed from the microfiber depleted suspension. In some embodiments, in a process of preparing a liquid chloroplast composition of the present disclosure, substantially all of non-chloroplast cellular content can be removed from the microfiber depleted suspension.

In some embodiments, in a process of preparing a liquid chloroplast composition of the present disclosure, at least 75% or about 75% to about 95% of soluble content outside of chloroplast can be removed from the microfiber depleted suspension. For example, at least 75%, at lest 80%, at least 85%, at least 90%, or at least 95% of soluble content outside of chloroplast is removed from the microfiber depleted suspension. In some embodiments, in a process of preparing a liquid chloroplast composition of the present disclosure, substantially all of soluble content outside of chloroplast is removed from the microfiber depleted suspension.

In some embodiments, the chloroplast suspension of the present disclosure obtained according to a process of the present disclosure has at least 75% or about 75% to about 95% of non-chloroplast cellular content removed from the microfiber depleted suspension. For example, at least 75%, at lest 80%, at least 85%, at least 90%, or at least 95% of non-chloroplast cellular content is removed from the microfiber depleted suspension. In some embodiments, the chloroplast suspension of the present disclosure obtained according to a process of the present disclosure has substantially all of non-chloroplast cellular content removed from the microfiber depleted suspension.

In some embodiments, the chloroplast suspension of the present disclosure obtained according to a process of the present disclosure has at least 75% or about 75% to about 95% of soluble content outside of chloroplast removed from the microfiber depleted suspension. For example, at least 75%, at lest 80%, at least 85%, at least 90%, or at least 95% of soluble content outside of chloroplast is removed from the microfiber depleted suspension. In some embodiments, the chloroplast suspension of the present disclosure obtained according to a process of the present disclosure has substantially all of soluble content outside of chloroplast removed from the microfiber depleted suspension.

In some embodiments, the liquid chloroplast composition of the present disclosure obtained according to a process of the present disclosure has at least 75% or about 75% to about 95% of non-chloroplast cellular content removed from the microfiber depleted suspension. For example, at least 75%, at lest 80%, at least 85%, at least 90%, or at least 95% of non-chloroplast cellular content is removed from the microfiber depleted suspension. In some embodiments, the liquid chloroplast composition of the present disclosure obtained according to a process of the present disclosure has substantially all of non-chloroplast cellular content removed from the microfiber depleted suspension.

In some embodiments, the liquid chloroplast composition of the present disclosure obtained according to a process of the present disclosure has at least 75% or about 75% to about 95% of soluble content outside of chloroplast removed from the microfiber depleted suspension. For example, at least 75%, at lest 80%, at least 85%, at least 90%, or at least 95% of soluble content outside of chloroplast is removed from the microfiber depleted suspension. In some embodiments, the liquid chloroplast composition of the present disclosure obtained according to a process of the present disclosure has substantially all of soluble content outside of chloroplast removed from the microfiber depleted suspension.

In some embodiments, the chloroplast suspension of the present disclosure has a ratio of chlorophyll/FBPP of about 70 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{FBPP \text{ in (intensity/mg powder)}} \times 10000000,$$

wherein the FBPP intensity is measured by immunoblot.

In some embodiments, the chloroplast suspension of the present disclosure has a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity is measured by immunoblot.

In some embodiments, the chloroplast suspension of the present disclosure has a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000.$$

In some embodiments, the chloroplast suspension of the present disclosure has a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right)\times 100.$$

In some embodiments, the liquid chloroplast composition of the present disclosure has a ratio of chlorophyll/FBPP of about 70 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{\text{FBPP in (intensity/mg powder)}}\times 10000000,$$

wherein the FBPP intensity is measured by immunoblot.

In some embodiments, the liquid chloroplast composition of the present disclosure has a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity is measured by immunoblot.

In some embodiments, the liquid chloroplast composition of the present disclosure has a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about it 4.7 ng/mg, the ratio of Rubisco/chlorophyll being $$\left(\frac{\text{Rubisco in ng/mg powder}}{\text{chlorophyll in (mg/g)}}\right)/1000.$$

In some embodiments, the liquid chloroplast composition of the present disclosure has a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right)\times 100.$$

In some embodiments, in a use of the present disclosure of a chloroplast suspension of the present disclosure, the chloroplast suspension of the present disclosure has a ratio of chlorophyll/FBPP of about 70 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{\text{FBPP in (intensity/mg powder)}}\times 10000000,$$

wherein the FBPP intensity is measured by immunoblot.

In some embodiments, in a use of the present disclosure of a chloroplast suspension of the present disclosure, the chloroplast suspension of the present disclosure has a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity is measured by immunoblot.

In some embodiments, in a use of the present disclosure of a chloroplast suspension of the present disclosure, the chloroplast suspension of the present disclosure has a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000.$$

In some embodiments, in a use of the present disclosure of a chloroplast suspension of the present disclosure, the chloroplast suspension of the present disclosure has a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right)\times 100.$$

In some embodiments, in a use of the present disclosure of a liquid chloroplast composition of the present disclosure, the liquid chloroplast composition of the present disclosure has a ratio of chlorophyll/FBPP of about 70 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{FBPP \text{ in (intensity/mg powder)}} \times 10000000,$$

wherein the FBPP intensity is measured by immunoblot.

In some embodiments, in a use of the present disclosure of a liquid chloroplast composition of the present disclosure, the liquid chloroplast composition of the present disclosure has a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity is measured by immunoblot.

In some embodiments, in a use of the present disclosure of a liquid chloroplast composition of the present disclosure, the liquid chloroplast composition of the present disclosure has a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000.$$

In some embodiments, in a use of the present disclosure of a liquid chloroplast composition of the present disclosure, the liquid chloroplast composition of the present disclosure has a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{FBPP \text{ in intensity/mg}}\right) \times 100.$$

In some embodiments, in a process of preparing a chloroplast suspension of the present disclosure, the chloroplast suspension has a ratio of chlorophyll/FBPP of about 70 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{FBPP \text{ in (intensity/mg powder)}} \times 10000000,$$

wherein the FBPP intensity is measured by immunoblot.

In some embodiments, in a process of preparing a chloroplast suspension of the present disclosure, the chloroplast suspension has a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity is measured by immunoblot.

In some embodiments, in a process of preparing a chloroplast suspension of the present disclosure, the chloroplast suspension has a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000.$$

In some embodiments, in a process of preparing a chloroplast suspension of the present disclosure, the chloroplast suspension has a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{FBPP \text{ in intensity/mg}}\right) \times 100.$$

In some embodiments, in a process of preparing a liquid chloroplast composition of the present disclosure, the liquid chloroplast composition has a ratio of chlorophyll/FBPP of about 70 to about 130, about 80 to about 120, about 90 to about 110, about 95 to about 105, about 97 to about 100 or about 98 to 100, the ratio of chlorophyll/FBPP being $$\frac{\text{chlorophyll in (mg/g)}}{FBPP \text{ in (intensity/mg powder)}} \times 10000000,$$

wherein the FBPP intensity is measured by immunoblot.

In some embodiments, in a process of preparing a liquid chloroplast composition of the present disclosure, the liquid chloroplast composition has a ratio of Rubisco/chlorophyll of about 25 to about 65, about 30 to about 60, about 35 to about 55, about 40 to about 50, or about 43 to about 49, the ratio of Rubisco/chlorophyll being $$\left(\frac{\text{Rubisco in intensity}}{\text{chlorophyll in (mg/g)}}\right)/1000,$$

wherein the Rubisco intensity is measured by immunoblot.

In some embodiments, in a process of preparing a liquid chloroplast composition of the present disclosure, the liquid chloroplast composition has a ratio of Rubisco/chlorophyll of about 2.5 ng/mg to about 6.5 ng/mg, about 3.0 ng/mg to about 6.0 ng/mg, about 3.5 ng/mg to about 5.5 ng/mg, about 4.0 ng/mg to about 5.0 ng/mg, or about 4.3 ng/mg to about 4.7 ng/mg, the ratio of Rubisco/chlorophyll being $$\left(\frac{\text{Rubisco in ng/mg powder}}{\text{chlorophyll in (mg/g)}}\right)/1000.$$

In some embodiments, in a process of preparing a liquid chloroplast composition of the present disclosure, the liquid chloroplast composition has a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{\text{FBPP in intensity/mg}}\right) \times 100.$$

In some embodiments, the process of the present disclosure removes about 20% to about 95%, about 20% to about 30%, about 70% to about 95%, about 70% to about 90%, about 70% to 80%, about 80% to about 90%, about 90% to about 95%, or more than 90% of saponin is removed from the Fabaceae family plant fragments.

It can be appreciated by a person skilled in the art that the initial ratios and the amounts of impurities and cellular contents may vary depending on the different cultivar.

While a description was made with particular reference to the specific embodiments, it will be understood that numerous modifications thereto will appear to those skilled in the art. The scope of the claims should not be limited by specific embodiments and examples provided in the present disclosure and accompanying drawings, but should be given the broadest interpretation consistent with the disclosure as a whole.

EXAMPLES

Example 1—Overall Description of the Industrial Process

Figure 11:
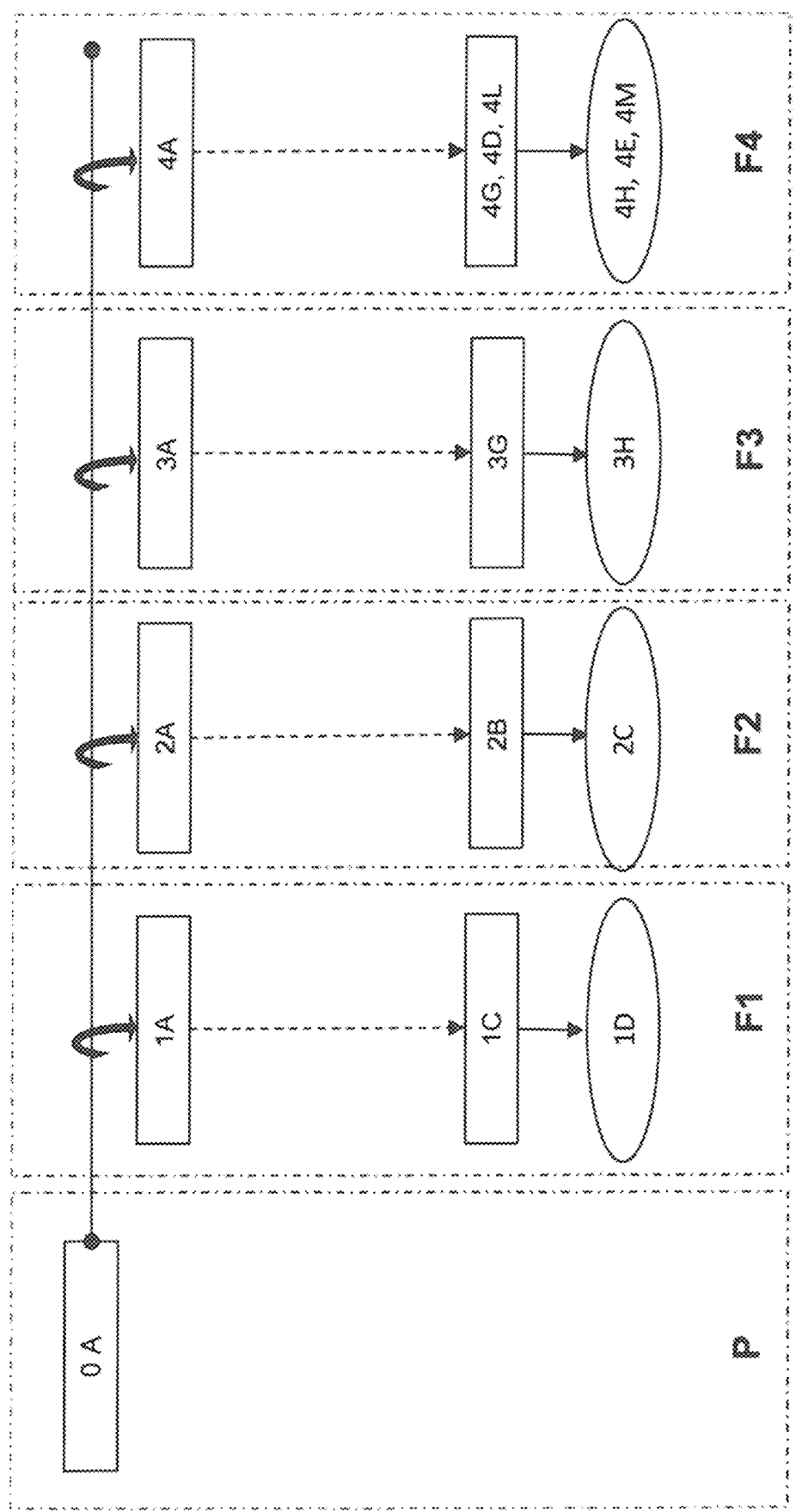
FIG. 11 is a flow sheet diagram of the overall industrial process, including the plant preparation and the four fractionations, according to an embodiment.

In FIG. 11, the five main process activities of the industrial process are described in brief.

In the production stage P, alfalfa grown over 4,000 hectares of agricultural land, is harvested and chopped to produce 160,000 metric tons of fresh plant fragment 0B (e.g. *Medicago sativa*).

In the first fractionation F1, the plants fragments 0B may undergo physical separation 1A and subsequent physical, chemical or biological conditioning 1C to obtain about 72,000 (60,000-80,000) metric tons of macrofiber composition 1D (ready to use end product #1).

In the second fractionation F2, the macrofiber depleted suspension 1H may undergo microfiber depletion 2A to obtain a microfiber fraction 2AA and subsequent physical, chemical or biological conditioning 2B to obtain about 1,000 (800-1,200) metric tons of microfiber composition 2C (ready to use end product #2).

In the third fractionation F3, the microfiber depleted suspension may undergo chloroplast separation 3A to obtain a chloroplast reduced suspension 3B and subsequent physical, chemical and mechanical conditioning 3G to obtain about 375 (150-500) metric tons of saponin precursor 3H to carry out end products development (precursor product #1)

In the fourth fractionation F4, the chloroplast suspension 3K may undergo chloroplast washing 4A to obtain a washed chloroplast suspension 4B comprising a high protein content as well as other components and molecules may be used as a biosourced precursor. Further physical, chemical or biological conditioning 4D, 4G, respecting food grade requirements inter alia, may be carried out so as to obtain about 2,400 (2,000-4,000) metric tons of dry chloroplast composition 4E and/or liquid chloroplast composition 4H (ready to use end product #3 and ready to use end product #4) while the same washed chloroplast suspension, as hereinabove, may undergo a different route of Rubisco conditioning 4L to obtain a Rubisco precursor 4M useful to carry out end products development (precursor product #2).

In sum, using this process, commercial (ready to use) end products 1D, 2C, 4E, 4H, and precursor products (biosourced industrial precursors) 3H and 4M may be obtained, in one embodiment.

Example 2—Biomass Preparation (0A)

Figure 12:
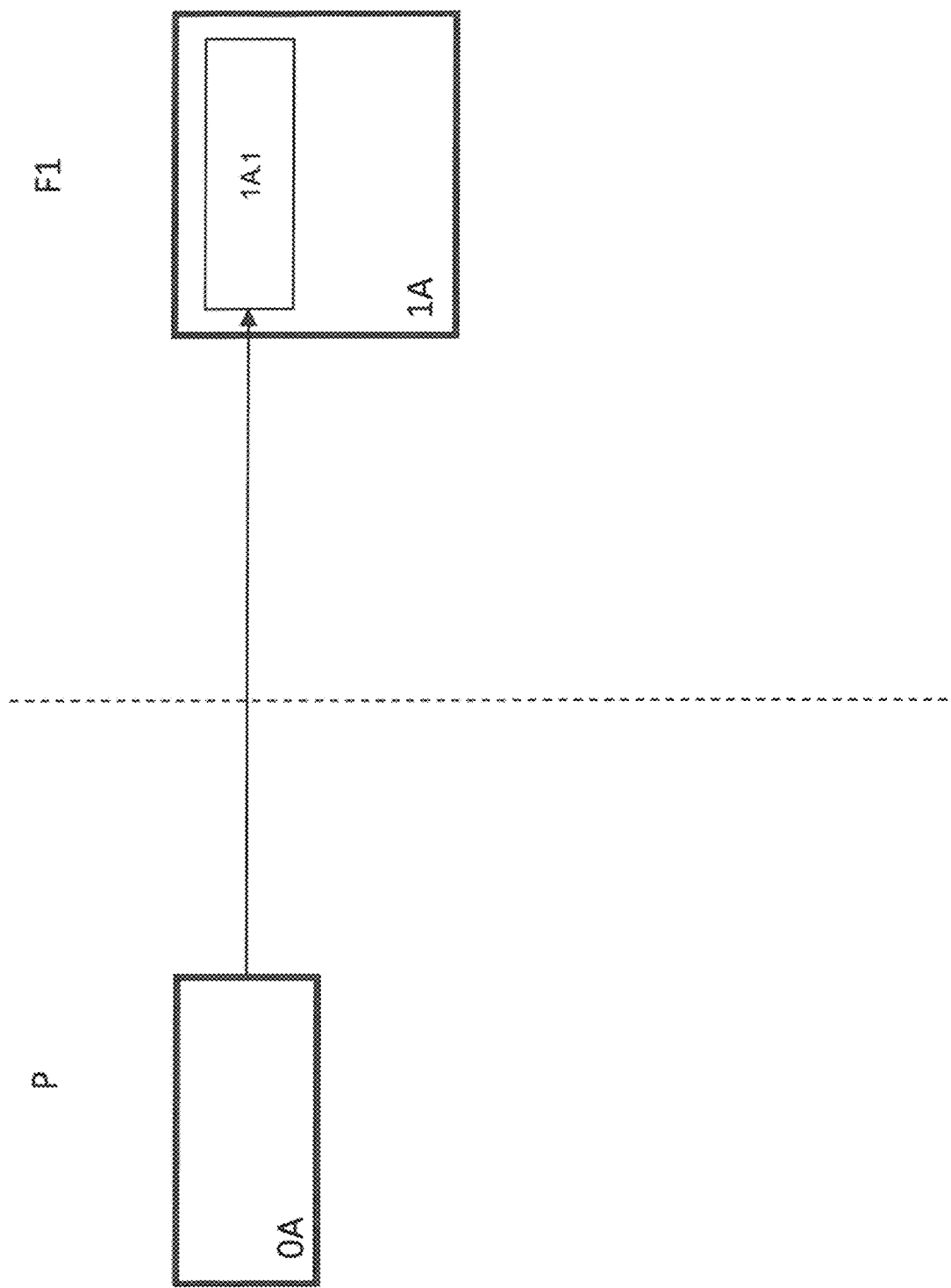
FIG. 12 is a flow sheet diagram of the preparation P of the plant input, according to an embodiment.

Biomass preparation 0A is illustrated particularly in the flow sheet diagram in FIG. 12 as well as in the flow sheet diagrams in FIGS. 1 to 9.

Biomass preparation 0A is related to plant production P. Alfalfa (*Medicago sativa*), in particular the Symphonie cultivar, is cultivated over about 4,000 hectares of agricultural land. The decision to harvest is based on a plurality of factors, including satellite surveys (further confirmed by site surveys), a suitable leaf to stem ratio (e.g. of 1:1 based on wet weight), a suitable plant height (e.g. 50 to 60 cm), the right specifications described hereinabove are generally obtained after a period of 28 to 35 days following a previous harvest.

Biomass preparation 0A starts by harvesting; harvest is conducted using 2 harvesters comprising 18×20 metric ton trailers. The truck loading time is about 20 minutes and a one-way trip to the plant may take from about 30 minutes to 2 hours. Uploading the harvest into a plant hopper may take for example about 20 minutes. Thus, in these conditions, the time from harvest to first fractionation F1 (activity 1A) can be about 4 hours. Using the following process, up to 100 metric tons per hour of alfalfa may be harvested, chopped and conditioned, and the harvest may be carried out 16 hours per day, for example 100 days per year.

Upon harvesting plant fragments 0B measuring about 10-100 mm, mostly about 20 mm in length, sodium metabisulfite ($Na_2S_2O_5$) at a concentration of about 10% (100 g/L) is added to the alfalfa fragments at a rate of about 5 liters per metric ton of alfalfa fragments.

The truck is weighed to compute the biomass input. The facility comprises two plant hoppers that can operate in parallel. Using conveyors, the plant fragments 0B are moving there way to fed directly into the intake of next fractionation stage.

The plant fragments 0B are about 2 cm in length, comprise leaves and stems, may be produced at a rate of about 160,000 cubic tons per year (100 cubic meters per hour, 16 hours per day, 100 days per year). The plant fragments have a shelf life of less than about 4 hours, have a moisture content of about 82% and may be mixed with sodium metabisulfite.

Example 3—First Fractionation (Activity 1A to Product 1H)

In this first fractionation F1, the freshly obtained plant fragments 0B undergo a two stage press ($1^{st}$ stage pressing and $2^{nd}$ stage pressing) to separate fiber components from liquid fractions. The first fractionation is detailed in FIG. 13 and also referred to in FIGS. 1 to 10B.

Figure 13:
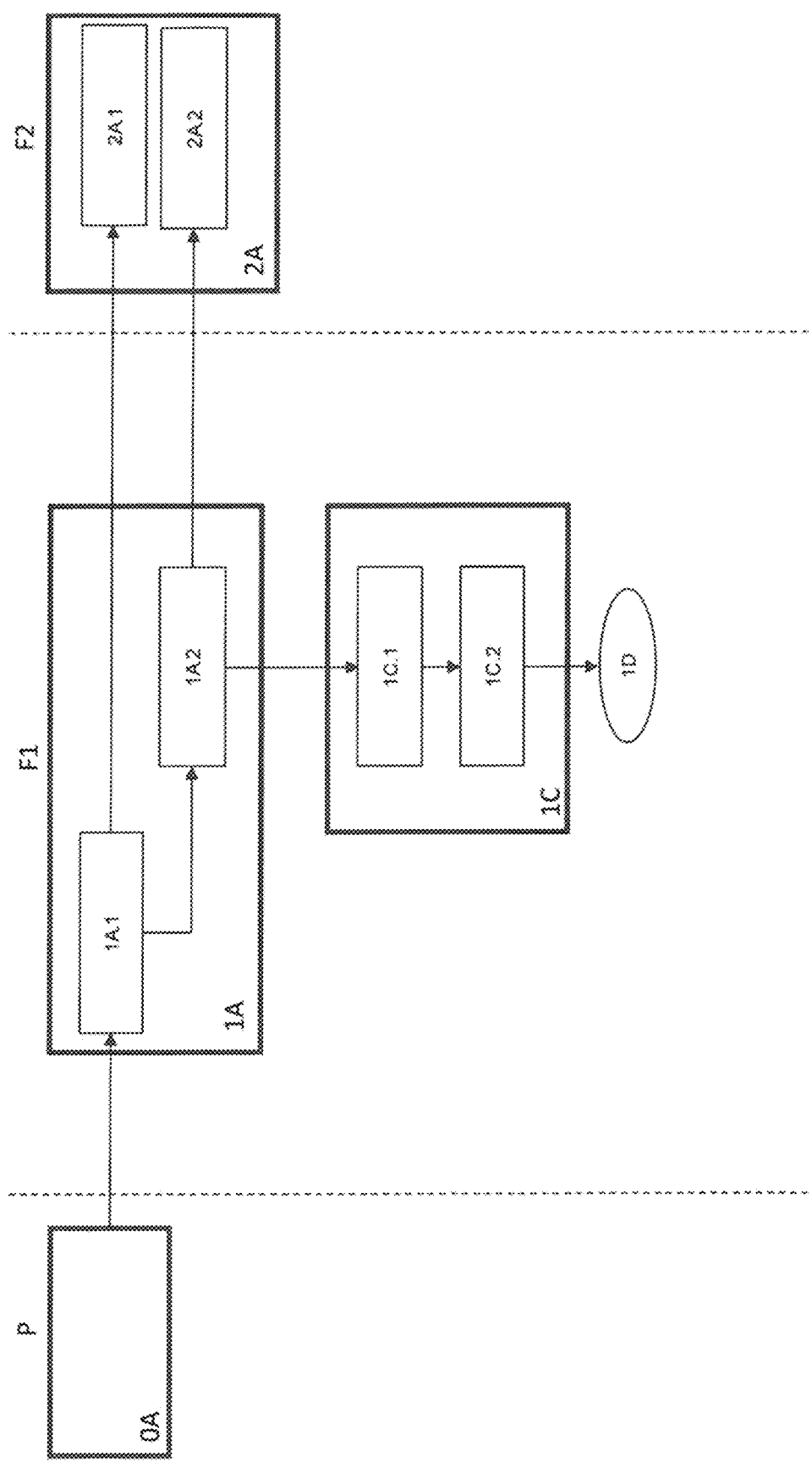
FIG. 13 is a flow sheet diagram of the first fractionation F1, according to an embodiment.

Referring now to FIG. 13, in the macrofiber separation 1A, plant fragments 0B are fed into 4 screw presses (e.g twin screw press), each press having a 30 metric tons per hour capacity, providing a total input capacity of more than 100 metric tons per hour. The plant fragments 0B are fed into the top of the presses using conveyors and/or distributors. About 200-300 ppm of antifoaming agent (in vegetable oil) is added at the lower end of the screw chamber. The back cone device applies a pressure of no greater than about 80 psi to build a restriction on the pressed cake moving out to better extract the liquid fraction from the plant fragment 0B. Upon pressing the fragments, a macrofiber depleted suspension 1H (operationally called green juice) (see also FIG. 2B describing the fractionation processes with reference to operationally used terms), is obtained at a rate of about 55 cubic meters per hour, and pressed cake, e.g. plant macrofiber fraction 1B, are obtained at a rate of about 45 metric tons per hour.

The pressed cake is the result of the $1^{st}$ pressing (1A.1) in the macrofiber separation 1A, as shown in FIG. 13. 45 metric tons of pressed cake will be further combined with about 50 $m^3$ of liquid (half of this liquid being fresh water and the other half recirculated process water coming from compound extraction 3E or elsewhere. The rehydrated pressed cake, having a moisture content of about 80%, may undergo a $2^{nd}$ stage pressing (1A.2) in order to extract more compounds from the initial plants fragments 0B. To do so, the pressed cake obtained from the $1^{st}$ stage pressing (1A.1) is rehydrated and fed into the top of the second train of presses (e.g. twin or single screw press) using conveyors and/or distributors. If required after observation of the presence of foam in excess, less than about 200 ppm of antifoaming agent (in vegetable oil) is added at the lower end of the screw chamber. The back cone device applies a pressure of no greater than about 80 psi to build a restriction on the pressed cake moving out to better extract the liquid fraction from the rehydrated pressed cake. Upon pressing the cake, a macrofiber depleted suspension 1H.2 (operationally called yellow juice) is obtained at a rate of about 57 cubic meters per hour, and a macrofiber fraction 1B, comprising plant macrofibers, is obtained at a rate of about 38 metric tons per hour.

The macrofiber depleted suspension 1H free flowing in the press bottom tank comprises about 11-15% suspended solids, is at a temperature of less than about 30° C., has a bright green color and may comprise some residual foaming. It may have a shelf life of about 16 hours if refrigerated (e.g. at 4° C.). At this stage, no preservative is added to the liquid fraction. The macrofiber depleted suspension 1H is subsequently pumped to microfiber depletion 2A in the second fractionation.

The macrofiber depleted suspension 1H.2 (as seen in FIG. 10B), from the $2^{nd}$ stage pressing, is free flowing in the press tank and comprises about 6-8% suspended solids. It is at a temperature of less than about 34° C., has a pale green color and may comprise some residual foaming. At this stage, no preservative is added to the liquid fraction. The macro fiber depleted suspension 1H.2 is subsequently pumped to microfiber depletion 2A.2 in the second fractionation. Care should be taken that even if the two macrofiber depleted suspensions, 1H and 1H.2 have some similar specifications, differences exist (e.g. solids content, moisture, protein content) such that the two downstream processes, microfiber depletion, 2A.1 and 2A.2, respectively, will be different. As an alternative, the two macrofiber depleted suspension 1H and 1H.2 may be processed in a single batch, if being driven by market demands for ready to use end products 4H and 4E or for saponin precursor 3H production.

The macrofiber fraction 1B (e.g. $2^{nd}$ stage solid pressed cake) has a moisture content of about 63%, is at a temperature of less than 34° C. and has a faded green color. It may have a shelf life of about 4 hours. The macrofiber fraction 1B is deposited onto conveyors and moved to macrofiber conditioning 1C (e.g. biological, chemical and physical conditioning).

Still referring to FIG. 13, macrofiber conditioning 1C starts by a biological conditioning (1C.1) of the macrofiber fraction 1B, adding inoculum (e.g. commercial bacterial inoculum) 2 g/metric ton of macrofiber fraction 1B in order to accelerate the ensiling of the macrofiber fraction 1B. The pH will decline within a 3-4 week period to about 4.3. By that time, the material will be stabilized by the lactic fermentation and oxidation and fermentation will be stopped/reduced for a long period of time (e.g.: 12 months).

It is important to stop fermentation upon reaching desired pH and, to stop oxidation by sealing the package of the macrofiber fraction 1B. In order to that, the macrofiber fraction 1B treated with the inoculum will be compressed (e.g. ratio 2.2:1) and packed (1C.2) in a sealed plastic bag (e.g. 40 kg bag or bigger bag) to be stored for a long period (e.g. 8-12 months). The result of it is the macrofiber composition 1D which is the ready-to-use end product #1.

Example 4—Second Fractionation (Activity 2A to Product 2G)

Microfiber depletion 2A comprises removing microfibers from the macrofiber depleted suspension 1H (operationally called green juice) and the macrofiber depleted suspension 1H.2 (operationally called yellow juice), both obtained from the first fractionation F1. These activities are illustrated particularly in FIG. 14 as well as in FIGS. 1, 2A, 2B, 4-10B.

Referring to FIG. 14, the macrofiber depleted suspension 1H (e.g. green juice) is pumped from the press bottom tank to microfiber depletion 2A (train #1). The macrofiber depleted suspension 1H is fed into 4 micro rotary screen filters, each having a capacity of about 15 cubic meters per hour. The filter comprises a 86 micron screen and free flow equipment is used. The resulting output consists of a microfiber-depleted suspension 2G (e.g. filtered green juice) at a rate of about 52 cubic meters per hour and microfiber fraction 2AA at a rate of about 3.3 metric tons per hour. The microfiber-depleted suspension 2G (at a temperature of about less than about 30° C.) is pumped to refrigerated tanks and can be stored for 16 hours e.g. at 4° C. It comprises about 10 to 16% of suspended solids and has a high protein content. The microfiber-depleted suspension 2G is subsequently pumped to the third fractionation F3 detailed below. The solid microfibers 2AA (further described below) are deposited onto conveyors. Separately, the macrofiber depleted suspension 1H.2 undergoes a similar micro-fiber depletion 2A.2 (train #2) as the liquid fraction 1H. It is filtered through 4 micro rotary screen filters, each having a capacity of about 15 cubic meters per hour. The filter comprises a 86 micron screen and free flow equipment is used. The resulting output consists of microfiber-depleted suspension 2G.2 (operationally called filtered yellow juice) at a rate of about 57 cubic meters per hour and microfiber fraction 2AA at a rate of about 1.7 metric tons per hour. The second microfiber-depleted suspension 2G.2 (maintained at a temperature of about less than about 30° C.) is pumped into refrigerated tanks and can be stored for 16 hours at 4° C. This filtered yellow juice (e.g. 2G.2) comprises about 6% of suspended solids. It is pumped to the third fractionation F3 detailed below. The solid microfibers 2AA are deposited onto conveyors.

Both microfiber fractions, obtained from filtering the macrofiber depleted suspension 1H (e.g. macrofiber depleted green juice) and macrofiber depleted suspension 1H.2 (e.g. yellow juice) are combined together to form the microfiber fraction 2AA. These microfibers have a moisture content of about 88%, a high protein content, a bright green color and a shelf like of about 4 hours.

Still referring to FIG. 14, the microfibers are produced at a rate of about 5 metric tons per hour and can be further conditioned according to the desired application. They may be further formulated 2B.1, for example be mixed with a liquid, or dried at low temperature 2B.2 (e.g. any solid in the dryer staying less than about 43° C.) using e.g. one or more rotary dryers, thus decreasing the moisture content from about 88% to less than about 12%. The dried microfibers are then packaged under air vacuum 2B.3 and are ready to be used as microfiber composition 2C (or as a nutritional supplement). These ready to use microfibers may be produced at a rate of about 650 (600 to 800) kg per hour and have a moisture content of about 11.5%. They have a shelf life of several years and can be packaged in for example 5 kg or 10 kg sealed bags.

Example 5—Third Fractionation (Activity 3A to Product 3K)

The third chloroplast separation 3A comprises isolating main chloroplast suspension 3K and a chloroplast reduced suspension 3B and is detailed in the flow sheet diagrams of FIG. 15 as well as in FIGS. 1, 2A, 2B and 5-10B.

Firstly, the microfiber-depleted suspension 2G (e.g. operationally called filtered green juice) contained in refrigerated tanks is acidified at the output of the tanks by mixing it with citric acid (acid concentration of 50%) at a flow of 18 L per hour (i.e. 400 ppm) in the 52 cubic meters of microfiber-depleted suspension 2G. The final pH ranges from about 4.8 to about 5.1.

The acidified suspension is then pumped out to 3 centrifuges to undergo chloroplast separation 3A, using 3 centrifuges, each having a minimum 5 000 L per hour concentrate output capacity and spinning at 10 000 G. The carry-over of the $1^{st}$ stage centrifugation is a liquid supernatant, the chloroplast reduced suspension 3B, produced at a rate of 33 cubic meters per hour. The concentrated jelly is the main chloroplast suspension 3K (operationally called green raw jelly containing chloroplasts) and is produced at a rate of 19 cubic meters per hour. The carry-over liquid from the chloroplast separation 3A is pumped out to trucks to be recycled back to agricultural lands as an organic liquid fertilizer and water balance contribution.

The main chloroplast suspension 3K has a green color, and comprises intact chloroplasts e.g. more than 75%-97% of the chloroplasts present are intact, and about 30% suspended solids. The temperature of the suspension is less than 34° C. and the shelf life may be increased to about 16 hours by refrigerating the suspension (e.g. at 4° C.). At this stage, no preservative is added. The unwashed chloroplast suspension is subsequently pumped to the fourth fractionation F4.

Now referring to FIG. 10B and FIG. 15, the chloroplast reduced suspension 3B (operationally called brown juice) still comprises some green pigment from residual chloroplasts and comprises about 3% of suspended solids. The temperature of the suspension is less than 34° C. and the shelf life is about 4 hours. The chloroplast reduced suspension 3B undergoes a chloroplast clarification 3C in Train #1 (3C.1) via tangential flow filtration (TFF), using multi-cell equipment, with about 80% retentate recirculation and 300 kDa porosity (ceramic). A filtrate, named the clarified suspension 3D, is produced at a rate of about 25 cubic meters per hour and undergoes a compound extraction 3E. A retentate is produced at a rate of about 8 cubic meters per hour. The retentate consists of a liquid second chloroplast suspension 3CC (e.g. a second chloroplast suspension) and comprises a high protein content and about 40% suspended solids. Its temperature is less than about 34° C. and can be stored for about 16 h when refrigerated (e.g. at 4° C.). This liquid second chloroplast suspension 3CC is then combined with the main chloroplast suspension 3K and pumped to the fractionation F4 described below.

The microfiber-depleted suspension 2G.2 (e.g. the mirofiber-depleted suspension obtained from the subactivity 2A.2 during the second fractionation) is reused given that it has a low protein content and it is a source of saponins. Filtration using TFF is carried out in the chloroplast clarification 3C in Train #2 (3C.2), at a rate of about 55 cubic meters per hour, using multi-cell equipment, at about 90% retentate recirculation and 300 kDa porosity (ceramic). A retentate, produced at a rate of 3 cubic meters per hour, corresponds to the second chloroplast suspension 3CC and comprises about 40% suspended solids. This second chloroplast suspension 3CC is also similar to main chloroplast suspension 3K. The two sources of 3CC, after 3C.1 and 3C.2, and the main chloroplast suspension 3K are mixed together prior introducing in forth fractionation F4 (as shown in FIG. 10B).

From suspension clarification 3C.2, a filtrate clarified suspension 3D is produced at a rate of about 52 cubic meters per hour. Both filtrates from 3C.2 and 3C.1 are combined together to form the clarified suspension 3D (e.g. sterile brown juice) produced at a total rate of about 77 cubic meters per hour, is sterile, comprising less than about 1% solid content and having a high saponin content.

To separate the saponin, as shown in FIG. 15, the clarified suspension 3D undergoes compound extraction 3E, starting by high-performance liquid chromatography (HPLC) using C18 XAD columns (3E.1). The clarified suspension 3D is fed to the columns at a rate of about 77 cubic meters per hour. A sequential process of loading, washing methanol (MeOH)/water, methanol (MeOH) eluting is carried out, followed by column cleaning prior next loading. A saponin concentrate in MeOH (3E.1) is obtained at a rate of about 15 cubic meters per hour. MeOH is then distilled (3E.2) from the concentrate so as to obtain a saponin concentrate paste (with about 20% residual MeOH). This saponin concentrate paste is spray dried (MeOH) (3E.3) and the resulting product is a saponin-enriched powder 3F produced at a rate of 100 kg (50-200) per hour and has a moisture of about 6 to 8%. In the saponin-enriched powder 3F the content in Medicagenic acid saponin is higher than 1%, generally higher than 3% and lower than 6%. The saponin-enriched powder 3F is enriched in medicagenic acid saponin, by washing out the soya saponins in favour of medicagenic acid saponin which is considered to have more interesting further applications. The saponin-enriched powder 3F is transferred to saponin powder conditioning 3G The saponin-enriched powder 3F, during conditioning, is packed and sealed under vacuum conditions in 1-5 kg bags to be stored for variable periods have a shelf life of several years. The saponin precursor 3H may be further: a) formulated to be used as pesticide/insecticide and/or b) processed in order to purify medicagenic acid saponin at a higher level (equal or >65%), then used, in combination or not with other nutraceutical compound or micro ingredient, as a nutraceutical molecule that may be useful for specific disease control.

The liquid remaining from compound extraction 3E (3E.1) is a sterile liquid comprising less than 1% suspended solids. About 25 cubic meters per hour of this liquid is recirculated back to $2^{nd}$ stage pressing 1A.2 as described in example 3 above, while about 50 cubic meters per hour of the liquid flowing through 3E.1 is recycled back to agricultural lands as organic liquid fertilizer.

Example 6—Fourth Fractionation (Activity 4A to Product 4M)

The fourth fractionation F4 is directed to the further separation of chloroplast and is detailed in the flow sheet diagram of FIG. 16 as well as in FIGS. 1, 2A, 2B and 6-10B.

The chloroplast suspensions obtained in the third fractionation F3, namely from the main chloroplast suspension 3K and as well from second chloroplast suspensions 3CC, from 3C.1 and 3C.2, are combined in a mixing tank to which fresh water (at a rate of about 60 cubic meters per hour) is added. The mixture obtained is produced at a rate of about 90 cubic meters per hour and is pumped to a chloroplast washing 4A, similar to chloroplast separation 3A, that uses 3 centrifuges, each having a minimum 5 000 L per hour output capacity and spinning at 10 000 G. The outputs of the $2^{nd}$ stage centrifugation include a carry-over produced at a rate of 74 cubic meters per hour and a washed chloroplast suspension 4B produced at a rate of 16 cubic meters per hour).

The washed chloroplast suspension 4B has a high protein, lipid, pigment and antioxidant content and 30-40% w/v solid content, 10-15% w/w (dry basis), 85-90% moisture, green color, residual anti-oxidation after 1A.1, residual citric acid after 3A.1, intact chloroplasts greater than 90%. The washed chloroplast suspension 4B may undergo solid chloroplast conditioning 4D and/or liquid chloroplast conditioning 4G and/or compound extraction 4J.

The washed chloroplast suspension 4B may undergo a solid chloroplast conditioning 4D. In this scenario, referring now to FIG. 16, the washed chloroplast suspension 4B undergoes first a conditioning 4D.1 in which some micro-ingredients or food grade preservatives may be added (solid or liquid formulas) to the washed chloroplast suspension 4B based on desired needs.

The formulated chloroplast suspension is transferred from 4D.1 to 4D.2 to be dried (air) using 2 spray dryers which can operate 24 h. The chloroplast suspension transferred from 4D.1 is 85% moisture and undergoes by pumping in the spray dryer with air heated at a temperature not exceeding 150° C. The cyclonic process will be constantly monitored in order to ensure that the end powder temperature, after evaporation of water, remains below 43° C. the result is a chloroplast powder with about 6% (6-8%) moisture.

Resulting from 4D.2, the chloroplast powder is produced at a rate of 2.4 (1.6-2.5) metric tons per hour, having a bright green color and sensitive to light, moisture and needing to be sealed or packed in bags or pails blocking light. The chloroplast powder is suitable for human consumption as food and micro-ingredient. The chloroplast powder may be packaged (4D.3) in vacuum packed in 1 kg, 2 kg and 5 kg bags or 20L food grade pail. Special care will be taken to secure vacuum, possibly under nitrogen blanket and has a shelf life of several years. The final result is a dry chloroplast composition 4E ready to use (end product #3).

The washed chloroplast suspension 4B may undergo a liquid chloroplast conditioning 4G. In this scenario, the washed chloroplast suspension 4B undergoes first in conditioning 4G.1 that some micro-ingredients or food grade preservatives could be added (solid or liquid formulas) to washed chloroplast suspension 4B in order to respect final receipt requests. The washed chloroplast suspension 4B may be combined with DHA fatty acids (long chain) and/or other nutrients.

Resulting from 4G.1, the liquid containing the chloroplasts is produced at a rate of about 15 cubic meters per hour, with a moisture content of about 85% and is sensitive to light, temperature and needing to be sealed or packed in pails stopping light in 4G.2. This liquid containing the chloroplasts is vacuum packed in 20L food grade pail with special care to secure vacuum and to replace the air at the top of the pail with nitrogen, protected from light and oxygen; pails are transferred to cold storage (2° C.<t°<4° C.) and will be shipped to final user within 4 months of delay. The final result is a liquid chloroplast composition 4H ready to use (end product #4).

The washed chloroplast suspension 4B may undergo compound extraction 4J. In this scenario, the washed chloroplast suspension 4B undergoes first in chloroplast fractioning 4J.1 using limited amount of shearing (the preferred processing way), high pressure differentials, hypo- or hypertonicity of the external fluids, ultrasound and/or other mechanical or chemical stresses in order to disrupt the chloroplast membrane and release in solution all the soluble components of the chloroplasts, leaving partially disrupted thylakoid membranes in suspension. At anytime, the temperature remains under 34° C. The suspension is transferred to 4J.2 for isolating solid material trough TFF.

In 4J.2, using TFF 0.2 microns, or filtration or flocculating/decanting, in order to capture in retentate, vegetal debris, membranes and very high molecular weight structure, over 1,760,000 KDaltons, permit to keep in filtrate sugars, low relative quantities of different enzymes and 100% of the Rubisco; the Rubisco having a molecular weight of about 540 kDaltons. The filtrate is transferred to 4J.3 to isolate the Rubisco. On the other hand, the retentate containing vegetal origin green structures and molecules may be kept for further transformation or recycled as a fertilization agent back to agricultural lands.

The filtrate coming from 4J.2 is processed in 4J.3 to isolate the Rubisco using TFF 500 kDaltons or filtration or flocculating/decanting, to capture in retentate, Rubisco having a molecular weight of about 540 kDaltons. The retentate, Rubisco suspension 4K will be kept, being mainly Rubisco at a high degree of purity, native and not exposed to chemicals neither to t°>37° C.; is 40% solids (w/v), 80% moisture. The Rubisco suspension 4K will to the undergo Rubisco conditioning 4L. On the other hand, the filtrate containing vegetal origin sugars, enzymes, molecules may be kept for further transformation or recycled as a fertilization agent back to agricultural lands.

Rubisco conditioning 4L consists in conditioning according to different alternatives related to the applications or uses targeted. Firstly, as an option, it is possible to add complementary ingredients to the Rubisco suspension 4K and/or adding a food grade protective agent. Secondly, the Rubisco suspension 4K resulting from 4J.3 (80% moisture), after addition of complementary ingredient or not, is pumped into a spray dryer with air heated at a temperature note exceeding 150° C.; the cyclonic process will be constantly monitored in order to ensure that the end powder temperature, after evaporation of water, remains at or below 45° C. As an alternative, it is possible to use freeze drying instead of spray drying, depending of the end use requirements. The resulting Rubisco powder is a 10% (8-12%) moisture suspension identified as Rubisco precursor (4M) which is the second precursor product #2 used for further end product development.

Example 7—Fractionation and Medicagenic Acid Saponin Recovery

In another example, with reference to FIG. 10B, 1000 kg of fresh leafy alfalfa biomass is harvested and cut into 2-5 cm fragments. Typically, the biomass is harvested at a development stage where the leaf to stem ratio is at about 1:1 (wet weight/wet weight) and where no leaves appear wilted or dried at the base of the shoots. Preference is given to juvenility of the biomass rather than yield on a per surface basis. Juvenile shoots contain a relatively low level of lignification, which in turn reduces the strength required for subsequent mechanical disruption. Juvenile shoots also contain a higher relative ratio of active leafy material which is desirable for the recovery of green solids (comprised mainly of chloroplasts) among other things. Concentrations of various components disclosed in the present example were measured by independent laboratories using standard methods applicable.

Preparation of the Harvested Biomass

Preference is given to the use of sharp cutting devices on the harvester, for example adjustable cutting tables with sharpened blades rather than crushing devices such as hammermills. Sharp cutting of the shoots reduces crushing of the shoot tissue which results in limited losses of plant liquids and solutes. As a general rule, sharp cutting that reduces plant fragments to a length of 2-5 cm limits biomass biochemical decay during collection and transport up to the press which would otherwise occur rapidly if the biomass was crushed. In addition, it is preferable to spray the biomass during its collection with an antioxidant (e.g. potassium or sodium meta bisulfite) in order to limit oxidative decay. Cutting the biomass to 2-5 cm fragments also reduces the strength required for subsequent mechanical disruption.

First Pressing of the Biomass

The plant fragments (0B) are passed through a screw press at shaft speed and cone pressure that allows maintenance of a temperature difference to less than 6° C. between biomass temperature at entry and pressed green juice (1H) temperature or fibrous cake (1B) at the exit. In addition, screw press settings are adjusted so that the maximum temperature reached for any processed component, at any time during pressing, remains below 34° C. Typically, but not restricted to these values, and depending on the status of biomass water content at the entry, this first passage through the press will yield about 450 kg of fibrous cake at 28% dry matter and about 550 L of a green juice (1H) at about 12% dry matter and solids content of about 14% (weight/volume) (see for example FIG. 13). Microscopic observations and various other characterizations of the green juice (1H) have shown that the bulk of solids present in the green juice (1H) consists of intact chloroplasts of average size at 4-7 microns (as further detailed below).

The medicagenic acid saponin content of the biomass (0B) at entry is about 3300 ng/g (592 g in total) on a dry weight basis. It will be understood however that medicagenic acid saponin content can vary depending on biomass source, for example its genus (*Medicago, Lotus, Trifolium*) and related species, cultivar, variety, germplasm, development stages and seasonal variations of such plants, especially for plants with multiple harvest cycles within a season and for perennial plants. After the first pressing (1A.1), the content in medicagenic acid saponin of the fibrous cake (1B) is decreased to about 316 g in total, corresponding to about ⅔ of the initial total medicagenic acid saponin content.

Second Pressing of the Biomass

This fibrous cake (1B) is then mixed with 500 L of rinsing liquid (e.g. water) so that the solids and solutes trapped therein can be rinsed out and recovered as a second liquid suspension or yellow juice (1H.2). Other suitable rinsing liquids include, for example, liquids with low solute contents produced as waste from other activities (e.g. 3A and 3C) of the process flow. The volume of added rinsing liquid can vary but is typically adjusted to about 50% of the initial biomass weight at entry, or to the volume of the first green juice (1H). The mixing of the fibrous cake (1B) with the rinsing liquid can be accomplished by various methods, in batch or as a continuous flow. The preferred method is a continuous flow where the fibrous cake (1B) is carried out from the first screw press by a conveyor, sprayed with adjusted amounts of rinsing liquid, loaded to a rotary mixer and fed to a second screw press.

The watered fibrous cake is then pressed again (1A.2) under conditions that allow control of temperature differences to less than 6° C. between the fibrous cake (1B) temperature at entry and the yellow juice (1H.2) temperature at exit. In addition, screw press settings are adjusted so that the maximum temperature reached for any processed component, at any time during pressing, remains below 34° C. This second passage through the press (1A.2) will yield about 380 kg of fibrous cake at about 37% dry matter and about 620 L of a yellow juice (1H.2) at 2.75% dry matter and solids content of about 6% (weight/volume). It will be understood that the above-mentioned yield may vary depending on the liquid content of the fibrous cake at the entry. After this second pressing (1A.2), the content in medicagenic acid saponin of the fibrous cake (downstream of 1A.2) is decreased to about 206 g in total, corresponding to about ⅓ of the initial total content. Typically, the washed fibrous cake downstream of the second pressing (1A.2) will contain about 37% of dry matter and in the case of alfalfa, about 18% protein (dry weight basis).

Packaging and Fermentation of the Fibrous Cake

In this example, the washed and pressed fibrous cake (downstream of 1A.2) subjected to two pressings is compressed with a pneumatic device to about one half of its initial volume and pressured-packaged with a plastic film. This is preferably performed immediately following the second pressing (1A.2). Lactic fermentation which will occur during the subsequent 3-4 weeks and the silage will stabilize at a pH of about 4.2. Alternately, the pressed fibrous cake can be mixed with a commercial bacterial inoculum that will accelerate fermentation. A saponin reduced ensile compressed fibrous cake with a high moisture content (1D) is obtained.

Defibering of the Green and Yellow Juices

Both green (1H) and yellow juices (1H.2) are then passed through a filtering device for removal of microfibers (2A and 2A.2) that have been produced by shearing during the pressing stages. For example, the filtering device is a rotary device with a screen filter of 86 µm in pore size. Filtering of the green juice (1H) produces about 32.5 kg of microfibers (2AA) at about 11.5% dry matter content. Filtering of the yellow juice (1H.2) produces about 16.6 kg of microfibers (2AA) at about 11.5% dry matter content. Overall, both filtrations (2A.1 and 2A.2) result in the production of microfibers (2AA) weighing about 5% of total initial wet biomass weight and sequestering about 2.5% of the total initial content in medicagenic acid saponin.

Selective Capture of the Green Solids from the Green Juice

The green juice (2G) resulting from the previous defibering (2A) is then fractionated by sedimentation of the solids either by for example centrifugation or tangential flow filtration. Typically, to help sedimentation, the green juice (2G) is brought to pH below 5.1 through addition of a mild organic acid, for example citric acid. Other suitable organic acids include for example malic acid, succinic acid and lactic acid. Acidification below the isoelectric point of the chloroplast membrane will favor aggregation and facilitate sedimentation. The mixing is carefully and thoroughly performed so that the pH does not decrease below 4.8 at any location in the green juice. Acidification below a pH of 4.8 would compromise the biochemical integrity of solutes (including for example carotenes, chlorophyll, antioxidants, anthocyanins, proteins, omega-3 phospholipids) as well as the physical integrity of the chloroplasts.

Centrifugation of this acidified green juice (2G) is performed in a continuous flow centrifuge (3A) with sequential discharge such as a CSC-15 (GEA) at 10 000 g. Care is taken that the temperature of the centrifuged suspension does not reach 34° C.; this implies, as per this example, that the flows through the centrifuge are adjusted, to restrict the retention time, to values of about 500 L/hr. Maintaining the temperatures below 34° C. allows preserving the biochemical integrity of solutes (including for example carotenes, chlorophyll, antioxidants, anthocyanins, proteins, omega-3 phospholipids). Under these conditions, the carry-over or brown juice (3B) contains about 6.5% solids (weight/volume) and represents about 70% of the initial loaded volume, while the green jelly (3K) contains about 31.5% solids (weight/volume) and represents about 30% of the total initial volume load. It will be understood that these values can vary according to the initial solids content of the green juice (2G), flow rates, discharge frequency or any other adjustments of centrifugation conditions. As an example, a lower solids content will allow higher flow rates, lower discharge frequency while maintaining the liquid temperature below 34° C.

Characterization of the solids size distribution in the two intermediary products (3B and 3K) exiting from centrifugation (3A) demonstrates that the chloroplasts contained therein are mostly intact chloroplasts having an average size of 5-7 microns with some aggregation due to acidification (see Example 11 for more details). Intactness of chloroplast physical structure is maintained up to this stage of the process flow by strict control of mechanical and chemical interventions. In this example, the combination of the choices in: biomass maturity upon harvest, mild but efficient biomass preparation, low-shearing and low-differential pressure during mechanical disruption (screw press), control of temperature (<34° C.) in the screw press, weak organic acids for acidification, control of pH (4.8<pH<5.1) during acidification, and/or control of temperature during centrifugation are preferable to maintain chloroplast integrity. Maintaining chloroplast integrity allows chloroplast components to remain sequestered within the chloroplast, thus in turn allowing the mechanical separation of whole chloroplasts from the liquid fraction in one sedimentation activity. This is important to the continuity of the process flow as it also allows the mechanical separation of an important protein component of the plant leaf material, namely Rubisco (ribulose bis-phosphate carboxylase), which is a major chloroplast protein and the most important plant protein with regards to nutrition. This approach of preserving chloroplast integrity is in contrast with other processes used to fractionate photosynthetically-active biomass, where the use of excessive mechanical strength for disruption and manipulation, use of high temperatures and/or extreme pH conditions for coagulation of soluble or solid components during fractionation results in breakage of chloroplast integrity and release of the key Rubisco protein component in the liquid fraction. Breakage of chloroplast integrity strongly reduces protein quality of the green solids suspension resulting from such fractionation and makes Rubisco recovery from the liquid fraction extremely challenging. In addition, use of high temperatures and/or extreme pH conditions for coagulation and during fractionation results in increased oxidative decay of major nutritional solutes (e.g. carotenes, chlorophyll, antioxidants, anthocyanins, proteins, omega-3 phospholipids) that are heat labile and pH sensitive.

Clarification of the Brown Juice

As mild centrifugation conditions are used for the chloroplast separation (3A), the resulting brown juice (3B) can still contain between 20% and 40% of the initial chloroplasts (about 6.5% weight/volume). These chloroplasts can be recovered by, for example, tangential flow filtration (TFF) (3C.1). Care is taken that the temperature of the suspension does not reach 34° C. during TFF; this implies that the flows of recirculation are adjusted to restrict shearing. Maintaining the temperatures below 34° C. allows preserving the biochemical integrity of solutes (for example carotenes, chlorophyll, antioxidants, anthocyanins, proteins, omega-3 phospholipids). In these conditions, the clarified suspension (or brown juice) (3D) contains less than 0.2% solids and represents about 70% of the initial loaded volume. The second chloroplast suspension (or concentrated retentate) (3CC) resulting from the TFF (3C.1) contains about 40% solids and represents less than about 30% of the total initial volume load.

Clarification of the Yellow Juice

The yellow juice (2G.2) resulting from the second defibering (2A.2) is then clarified (3C.2) similarly to the first clarification (3C.1) (see above). Coming from the low solids concentration of the yellow juice, lower than 6-7%, clarification (3C.2) is preferably performed by TFF, without requirement to go through centrifugation first. Care is taken so that the temperature of the yellow juice (2G.2) does not reach 34° C. during TFF; this implies that the flows of recirculation are adjusted to restrict shearing which generates heat. Maintaining the temperatures below 34° C. also allows preserves the biochemical integrity of solutes (for example carotenes, chlorophyll, antioxidants, anthocyanins, proteins, omega-3 phospholipids). In these conditions, the clarified suspension (3D) contains about less than 0.2% solids and represents about 70% of the initial loaded volume, and the concentrated retentate or second chloroplast suspension (3CC) contains about 40% solids and represent less than about 30% of the total initial volume load.

Washing of the Green Jelly

The green jelly (3K) typically contains about 31.5% solids and consists of about 30% of the initial load volume. This implies that about 70% of the green jelly (3K) consists of a liquid phase that still contains solutes such as saponins, polyphenols and volatiles that contribute to biochemical instability and are causally related to the "grassy" off-tastes and off-odors of extracts from leafy biomass. Thus, washing out (4A) of these solutes results in a green jelly (4B) with increased palatability and having a composition similar to that of commercial micro-algae (e.g. *Chlorella*). In addition, some of these solutes are of nutritional value if enriched and purified. In this example, 350 L of water is added to the green jelly (3K) which is then submitted to a "washing out" centrifugation cycle (4A), in the same conditions as those described above (3A). Alternately, the solids (3CC) resulting from the suspension clarification (3C.1 and 3C.2) can be mixed with water and added to the green jelly (3K). The total amount of liquid added can be adjusted to increase the washing effect of the activity (4A).

Typically, the chloroplast washing (4A) produces a washed green solids suspension (4B) with lower solute content and higher solids content (40% or over). The washed green solids suspension (4B) consists of about 25% of the initial loaded volume and about 14% dry matter content.

The chloroplast washing (4A) will also produce a carry-over at about 4.5% dry matter content and consisting of about 75% of the initial loaded volume. This carry-over would be recycled as a fertilization agent back to agricultural lands. Alternatively, as this carry-over contains washed solutes, including valuable solutes such as inter alia medicagenic acid saponins, it can in turn be clarified e.g. by TFF and recovered for further purification. It will be understood that these values can change significantly depending on the amount and solute content of the washing liquids used in the washing (4A).

Distribution of Medicagenic Acid Saponin Amongst Fractionation Products

A typical distribution of medicagenic saponin is shown in Table 1.

TABLE 1

| Fraction | % of total medicagenic acid saponin |
| --- | --- |
| Macrofibers 1D | 34.7 |
| Microfibers 2C | 2.5 |
| Green jelly 3K | 12.2 |
| Brown juice 3B | 44.9 |

Conditioning of microfibers and washed green solids suspension

In this example, the washed green solids suspension (from centrifugations and/or TFF) (4B) and microfiber fraction (2AA) are dried to about less than 6-10% moisture content as conditioning activities (4D and 2B respectively). The green solids suspension (4B) is dried to a powder form in a spray dryer wherein the temperature of the particles is maintained at or below 45° C. at all times. The microfiber fraction (2AA) is dried in a tumble dryer (2B) where the temperature of the microfiber material is maintained at or below 45° C. at all times. Other types of dryers can be alternatively used such as a flash dryer, a ring dryer, or a fluidized bed dryer. Maintaining the temperature at or below 45° C. preserves the biochemical integrity of important components of these two products, for example chlorophyll, carotenes, xantophylls, omega-3 phospholipids and proteins.

Fate of the Clarified Suspensions

All suspensions clarified by TFF (3D) are microbe free and without colloids. They are ready for further processing by methods (3E and 3G) currently used in the nutraceutical and pharmaceutical industry. In this example, medicagenic saponins are concentrated by a simple passage of the clarified suspension on a mixed solid phase matrix, for example (but not restricted to) a XAD matrix (Dow Chemicals) and elution in increasing concentrations of methanol.

Example 8—Use of the Saponin Precursor (3H) as an Insecticide

Another example is one in which the clarified suspension (3D) obtained from fractionations (see FIGS. 2A and 2B as well as FIG. 15) are enriched in medicagenic acid saponins by solid phase extraction (3E) on an ion exchange matrix and then used as an insecticide to control damages to potato leaves.

Enrichment

In this example, the clarified suspension (3D) is loaded (3E.1) without alteration or adjustments to a XAD matrix in a reaction vessel, at a ratio of 4/1 (volume of clarified suspe/volume of wet matrix). Prior to loading, the matrix had been conditioned in 100% methanol and washed and equilibrated in pure water. The matrix is then washed with increasing concentrations of methanol up to 65% (methanol/water) and the washings discarded. The medicagenic acids are then eluted from the matrix with 100% methanol. The eluate is then evaporated to 20% of its volume, diluted in water (3 volumes) and lyophilized.

Many variations of this enrichment method exist. Changes can be made for example (but not restricted to) in the choice of the matrix (for example affinity, reverse phase, hydrophobicity), the loading, washing and elution conditions, the mode of operation (vessels vs column) or continuous versus step gradients. In this example, the final concentration of medicagenic acids was about 3% (31 mg/g of dry weight), but some batches could reach 6-8% (60-80 mg/g).

Insecticide Test
Colorado Potato Beetle (CPB) Rearing

CPB eggs were provided by the Fredericton Research and Development Center (Agriculture and Agri-Food Canada). Upon receipt, the eggs were deposited on isolated caged potato plants and the CPB were reared to the second instar stage. The rearing is done with a light cycle of 16 hrs:8 hrs (light:darkness) and temperature of 23° C.: 20° C. (day:night).

Saponin Precursor Formulation

The product was in the form of a freeze-dried powder. It was a preparation enriched in medicagenic acids (for example 3-6% on a dry basis) by solid phase extraction from the clarified suspension obtained as described herein. 100 mg of dried product was first dissolved in 2 mL of ethanol and water added to meet the 80/20 (water/ethanol) ratio. The solution was subsequently filtered (SCFA filter 0.45 μm). The final solution appeared clear and homogeneous with no precipitate visible to the naked eye.

Test Protocol

Figure 17:
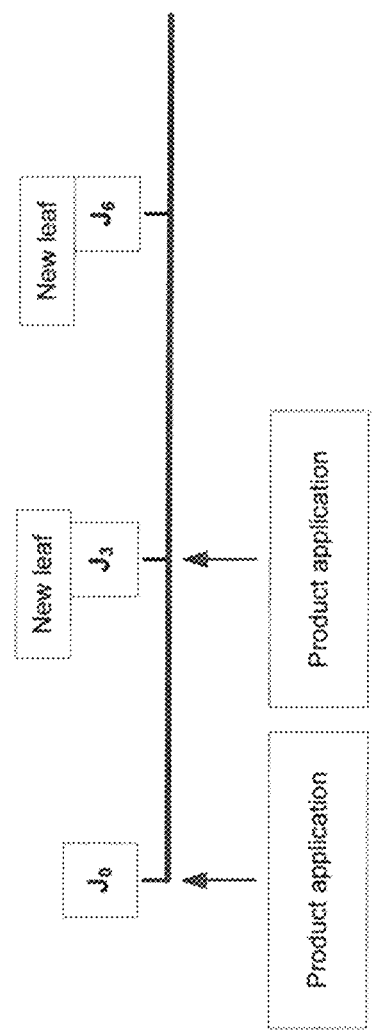
FIG. 17 is a timeline indicating the dates of application of medicagenic acid as an insecticide.

Leaves of potatoes of identical size were excised from the plants. Using a small spray bottle, each solution was applied to both leaf surfaces. Three sprays (100 μL/spray) were applied on each side of the leaves to cover the entire surface. The leaves were dried in the open air for thirty minutes. Subsequently, the leaves were placed on a wet filter placed in a petri dish. A larva (stage 2) was then deposited on each leaf. Three days later, the leaves were replaced by fresh leaves treated with the product (FIG. 17 hereinafter). A new leaf change was made on Day 6. The test was pursued up to Day 9. Only untreated leaves were then used for Day 6 and Day 9.

Four dilutions of the initial enriched preparation were used: 2.5 g/L, 1.25 g/L, 0.625 g/L, 0.31 g/L. Control consisted of the 80/20 (water/ethanol) solvent.

A digitalized image of the leaves was taken before and after contact with the larvae. Using the Image J software, it was thus possible to calculate the surface of the devoured areas for each of the conditions.

Results

The survival rate of larvae exposed to the product decreased sharply for all concentrations (dilutions) used. All the larvae that were exposed to the highest concentration (2.5 g/L) died. It is also noted that the survival rate is decreased with lower concentrations (0.625 and 1.25 g/L). No mortality was observed with the lowest concentration (0.31 g/L).

Figures 18A, 18B, 18C:
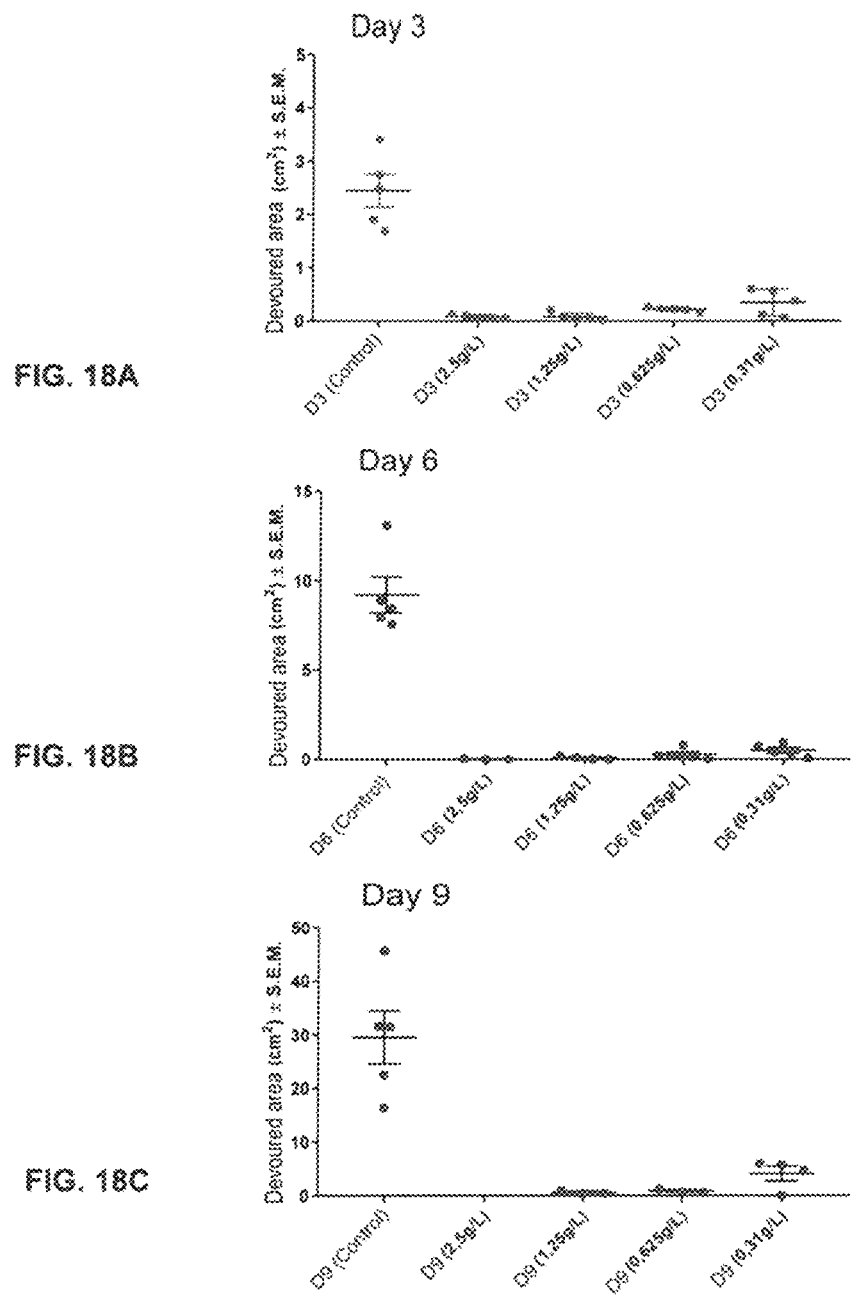
FIGS. 18A, 18B and 18C are a series of graphs showing devoured areas of potato leaves over time based on various concentrations of medicagenic acid saponins.

Consumption of leaf material was dramatically decreased by exposure to the product (FIG. 18), at all concentrations. At the highest dilution of 0.31 g/L, the larvae had consumed 86% fewer leaves than the control larvae at Day 9.

Conclusions

Results show that the saponin precursor (3H) extracted from alfalfa has a strong insecticidal effect on larvae of potato Colorado beetle. This product was not formulated (aside from dissolution in water/ethanol mixture). Under the current protocol, it was not possible to demonstrate if the insecticidal effect is only repulsive. The repulsive effect of the compound is so strong that death of the larvae occurred as a result of starvation. Saponins (including medicagenic acids) have been shown to have different insecticidal mode of actions.

Example 9—Use of Dried Chloroplast Suspension as a Replacement of Marine Micro-Algae in the Diet of Juvenile Molluscs In this example, dried chloroplast powder (4E) was used as a replacement for marine micro-algae in the diet of juvenile molluscs. The diet treatment and feeding regimen are detailed in Table 2 below.

Biological Material

The microalgae cocktail was a mixture of *Isochrysis galbana*, *Pavlova lutherii* and *Chaetoceros gracili* in a ratio of 1:1:1. Dried chloroplasts 4E were produced as described herein. Molluscs were 8-week old male and female juveniles from species *Mytilus edulis* produced at University of Quebec Aquaculture Station from adults harvested at St-Peters Bay in Prince Edward Island (Canada).

TABLE 2

Treatment and Feeding regiment

| Treatment | Number of replicates | Feeding regimen | | Harvest time |
|---|---|---|---|---|
| | | Days | Doses* | |
| Control (100% microalgae) | 3 | 2 days | 100 000 cells/ml | 1 and 2 months |
| 50% microalgae + 50% dried chloroplasts (1:1) | 3 | 2 days | Cocktail: 50 000 cells/ml + Chloroplasts: 50 000 units/ml | 1 and 2 months |
| 50% cocktail + 100% dried chloroplasts (1:2) | 3 | 2 days | Cocktail: 50 000 cells/ml + Chloroplasts: 100 000 cells/ml | 1 and 2 months |

The number of chloroplasts used to calculate food intake was determined by counting the particles between 2 to 8 µm (Cellometer Auto T4 Nexcelom Bioscience). The number of microalgae was determined using a Beckmann Coulter Inc. Z2 counter. The concentrations of 50 000 cells/ml for the mixture of microalgae cocktail represents a mass of 2 µg of dry matter per ml. Since the experiments were carried out in 250 ml-flasks, the control treatment thus received 1 mg of dried microalgae and treatments with chloroplasts 0.5 mg of dry microalgae.

Procedure:

D0: 275 juveniles of 8 weeks were collected from a culture basin by selecting them with dissecting forceps, taking care to take individuals of similar size. Fifty juveniles were measured using binoculars to determine the average size of juveniles in each 250 ml sample. Two hundred and fifty juveniles were distributed in experimental Erlenmeyer flasks (25 juveniles per Erlenmeyer flask) with 250 ml of bubbling seawater at room temperature.

Every 2 days: Erlenmeyer water was replaced and a food ration was given for all treatments. Once a week, the juveniles were gently removed and the Erlenmeyer flasks cleaned to avoid any possible contamination.

D30-D60: On D30, water from the Erlenmeyer flasks was discarded and the juveniles were recovered with dissecting forceps. Juveniles were measured using binoculars to determine size and survival. At D60, juvenile size was again measured. More specifically, juvenile size was measured using Image Pro Plus software.

Results

Figure 19:
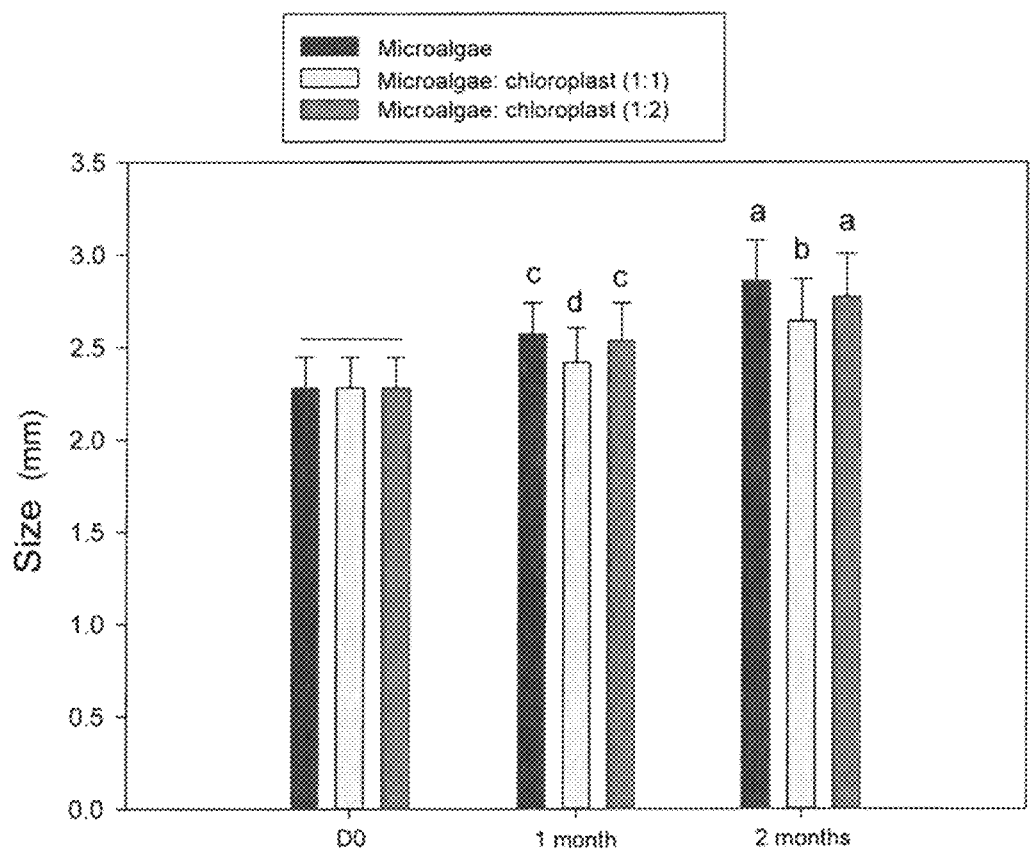
FIG. 19 is a bar graph illustrating the size of juvenile mussels (*Mylilus edulis*) depending on the diet.

FIG. 19 shows the average size of juvenile mussels (*Mytilus edulis*) at the first day (D0) of the experiment and after 1 and 2 months of maintenance under different diets. The data being distributed in a normal way (Levene test=2.116, p=0.063) and the variances being homogeneous (KS test=1.046, p=0.060), an analysis of variance was applied. The analysis reveals an effect of time (DF=1 and 433, F=52.9, p<0.0001) and diet (DF=2 and 433, F=10.4, p<0.0001) without interaction between time and diet (DF=2 and 433, F=0.32, p=0.726).

There is a steady growth of the juveniles during the first month, whatever the treatments. This suggests that the energy provided by the food rations was sufficient to keep the juveniles alive and lead to shell development. There are no significant differences between the 100% microalgae diet and the diet in which 50% of microalgae were replaced with twice the cell concentration of alfalfa chloroplast (microalgae:chloroplasts 1:2). However, the mixture of 50% microalgae and 50% chloroplast (microalgae:chloroplasts 1:1) led to a decreased growth of almost 10% over 2 months.

TABLE 3

Survival rates of juvenile mussels (in %) over time as a function of food processing

| Treatments | 1 month (%) | 2 months (%) |
|---|---|---|
| Microalgae | 98.7 ± 2.3 | 97.3 ± 2.3 |
| Microalgae:chloroplast (1:1) | 100 ± 0.0 | 96.0 ± 4.0 |
| Microalgae:chloroplast (1:2) | 97.3 ± 4.6 | 96.0 ± 4.0 |

The results show a very high survival rate (Table 3) without significant differences, regardless of the diet after 2 months of feeding (DF=2, Kurskal-Wallis=0.1, p=0.951). The average mortality observed was less than 4%, i.e. less than 2 juveniles per sample.

Example 10—Extraction of Medicagenic Acid Saponin and Potential Use as Anticholesterol Compound Certain types of saponins, and especially medicagenic acid saponins have a well demonstrated capacity to control cholesterol and other blood lipids ad thus can be used as a natural anticholesterol compound (as described in International Patent Application No. PCT/CA2007/001255 entitled MEDICAGENIC ACID SAPONIN AND USES THEREOF, filed Jul. 13, 2007, incorporated herein by reference in its entirety) with effects comparable to statins. In this example, the eluate rich in medicagenic acids produced as described in example 7 is further processed so that it is removed of contaminants such as genistein, coumestrol or other biologically active secondary metabolites and so that it reaches a concentration and purity that meets the requirements of a nutraceutical. In this example, originating from the saponin precursor (3H), the partially purified medicagenic acid reaches about 45% in purity and may be used for the control of blood lipids as described for other partially purified medicagenic acid preparations (described for example in International Patent Application No. PCT/CA2007/001255).

Experimental Protocol

Removal of Phenolic Compounds

Phenolic acids and polyphenols are plant secondary metabolites that are prone to oxidation and can cause instability in complex mixes. In addition, oxidized phenolics will have a tendency to precipitate. Some phenolics such as genistein and dadzein are associated with biological activities that can restrict the use of preparations in which they would be present at significant levels. Phenolics and medicagenic acids have different affinities and solubilities and this characteristic can be exploited to fractionate further preparations rich in medicagenic acids. In this example, the lyophilized eluate from the XAD matrix (3E) is resuspended in water and mixed with a solvent such as ethyl acetate. Ethyl acetate is a solvent of relatively low polarity that separates from water and for which many phenolics have a relatively high affinity. Alternately, salts such as NaCl can be added to water to promote phase formation. The proportion of this mixture depends on many factors, the most important is the relative charge of the water mix. If the XAD eluate is solubilized in a small volume of water, then the amount of ethyl acetate might exceed the volume of the water phase. Liquid-liquid phase extraction (in this case extraction of phenolics from a water solution), otherwise called partitioning, is a common practice in chemical engineering and ample examples of protocols are given in the literature.

In this example, the two fractions are mixed thoroughly by mechanical agitation and the phase then allowed to separate in a decanter. The water fraction containing the medicagenic acids is then recovered (3F). It can be either use as such for further processing or dried or lyophilized for storage. In this example, the enrichment obtained from liquid-liquid partitioning is of a factor of 3-5 with a final concentration in medicagenic acids between 15-20%. Both the enrichment factor and the final concentration can vary wildly depending on the initial concentration in medicagenic acids, the concentration in phenolics, the type and ratio of solvents used and the presence of other interfering compounds and many other factors.

Purifying Medicagenic Acid

The amphiphilic characteristic of saponins and the acidic nature of medicagenic acids can be used to further purify medicagenic acids from other metabolites and from other less charged saponins such as soyasaponins and bayogenins. In this example, the water phase of the previous liquid-liquid partitioning step is loaded onto a C18 matrix (50 micron) preconditioned in water. The matrix is washed with increasing amounts of methanol and or ethanol. Acetonitrile or other solvents can be added to help separation. Medicagenic acids are typically eluted at methanol or ethanol concentrations between 50-65%. This elution can be performed in one step, for example by washing the matrix with 35% methanol, then 50% methanol, and then recovering the medicagenic acids by a single step elution at 65% methanol (or ethanol). Alternately, the methanol and or ethanol concentration can be increased gradually (gradient) and medicagenic acids collected when the ethanol or methanol concentrations reaches 50%.

The ethanol or methanol is first evaporated from the mixture (ethanol:water or methanol:water mix) and then the final water preparation can be either spray dried, lyophilized, or formulated in liquid for prolonged storage as liquid or frozen.

Typically, the final concentration in medicagenic acids in such a preparation will be about 45%. This final concentration will vary depending for example (but not restricted to) on the initial concentration in medicagenic acids, the presence of contaminants, the hydrophobic matrix used, the protocol used for the loading and washing of the matrix, and for the specific elution of medicagenic acids and many other factors.

In light of the numerous previous studies published on the anticholesterol activity of alfalfa or medicagenic acid preparations, it is believed that such preparations enriched in medicagenic acids would be efficient in the treatment of high cholesterol conditions at different dosages, for example, daily dosages of between 50-100 mg.

Example 11—Preserving Chloroplast Integrity and Uses Thereof

Chloroplasts are fragile plant cell organelles composed of a significant proportion of thylakoid membranes in which enzymes (proteins) and pigments (carotenes and chlorophylls) responsible for the light phase of photosynthesis are embedded. They also contain a soluble fraction comprising Rubisco, an enzyme responsible for transforming the harvested light energy into organic molecules Rubisco. Rubisco is the most abundant enzyme in the whole plant and, in contrast with most bulk plant proteins that are derived from seeds, possesses an equilibrated amino acid balance. It is one of the most valued protein sources for human consumption.

Chloroplasts are surrounded by a fragile double-layered lipid membrane. Disrupting this membrane will result in leakage of chloroplast content, including Rubisco. It is well demonstrated that even a low amount of shearing, high pressure differentials, hypo- or hypertonicity of the external fluids, ultrasound and may other mechanical or chemical stresses will disrupt the chloroplast membrane and release in solution all the soluble components of the chloroplasts, leaving partially disrupted thylakoid membranes in suspension.

Known processes in the preparation of green protein concentrates from alfalfa include harvesting, conditioning, extraction and sedimentation methods that highly disrupt chloroplast integrity and result in leakage of the chloroplast soluble fraction. In such processes, the biomass is often passed through a hammer mill to reduce fiber size. This imposes significant shearing stress on the released chloroplasts. The crushed biomass is then often passed through a screw press under high screw speed and cone pressure which imposes even more shearing stress and creates high pressure differentials to which chloroplasts are sensitive. High torque on the screw also results in temperature increases that sometimes reach 60-65° C. High temperatures are also generally used to induce coagulation of the green solids. Typically, steam is injected in the circulating green juice and temperatures of greater than 85° C. are reached for extended periods of time (e.g. greater than 5 min). The combination of high temperatures in the press and during coagulation both contribute to the destruction of chloroplast (even thylakoid) structures and denaturation of key valuable chloroplast components such as carotenes, xantophylls and phospholipids. The final product of such processed is a green coagulate of thylakoids devoid of the most important chloroplast component, namely Rubisco, that has a strong pungent off-smell and that has a significantly oxidized pigment and lipid content. This coagulate is also contaminated with macromolecules from the liquid fraction (for example DNA) but also by unstable small molecular weight compounds that will also precipitate at these high temperatures. As a finishing step, the heated dewatered green paste is usually pelletized at even higher temperatures (often exceeding 100° C.). As a result, alfalfa green protein concentrates have often been undervalued and have had limited commercial successes and applications. With the current trend shift in human nutrition towards higher consumption of high quality plant protein, and with an urgent need for developing microalgae substitutes in the exploding markets of aquafeed, there is a need for approaches that allow the maintenance of nutritional value during processing of land crops with inherently high nutritional values.

Fractionation of the Biomass

The macrofibers (1D), green juice (2G), green jelly (3K), washed green solids suspension (4B), brown juice (3B) and clarified brown juice (3D) have been prepared as described herein (for more details, refer to example 7 hereinabove). The process steps are gears towards reducing to a minimum the mechanical stress imposed on the leafy biomass, in order to maintain the integrity of chloroplasts. Maintaining chloroplast integrity has many advantages: it sequesters valuable chloroplast components within a particle of defined size and physical characteristics that can be purified and "washed" from contaminating soluble components, such as phenolics or saponins, that contribute to undesirable characteristics such as off-odors and "grassy" tastes. Maintaining chloroplast integrity also ensures that the final product will be easy to suspend in liquids and be of a determined particle size upon resuspension. This is of importance if the purpose is to use the green solids suspension as aquafeed in replacement of microalgae and/or if the final usage is high quality end human nutrition micro-ingredient. In theory, and as most microalgae are unicellular organisms composed of more than 80% of their chloroplasts (dry basis), purified land plant chloroplasts, such as chloroplasts from alfalfa, should have a protein and phospholipid content approaching that of microalgae. By removing contaminating soluble components, it was rendered possible to prepare chloroplast suspensions that have a high, reproducible and unique phospholipid (omega-3)/protein ratio that exceeds that of most commercial microalgae preparations and of alfalfa commercial green protein concentrates.

Figure 21:
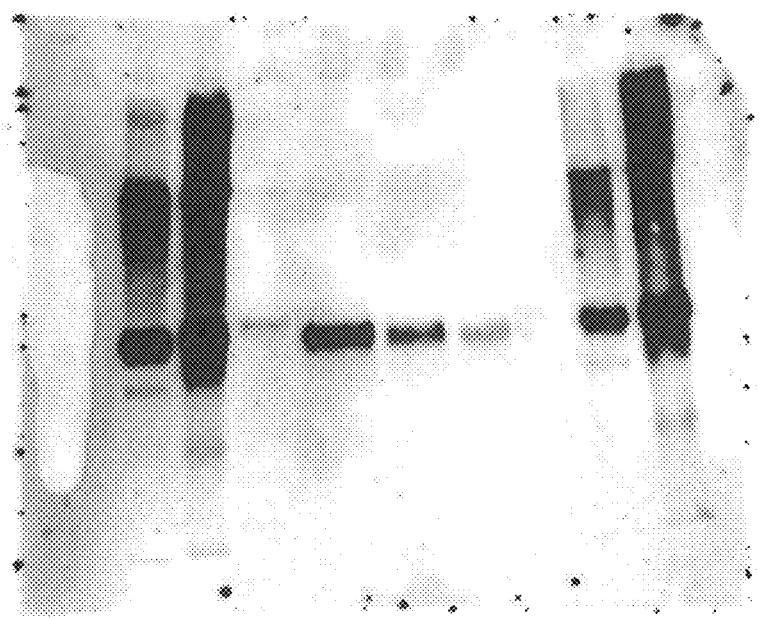
FIG. 21 is a western blot image of the distribution of Rubisco (heavy subunit) in the clarified brown juice 3D and dried chloroplast composition 4E of alfalfa obtained according to the process described herein.
Figure 22:
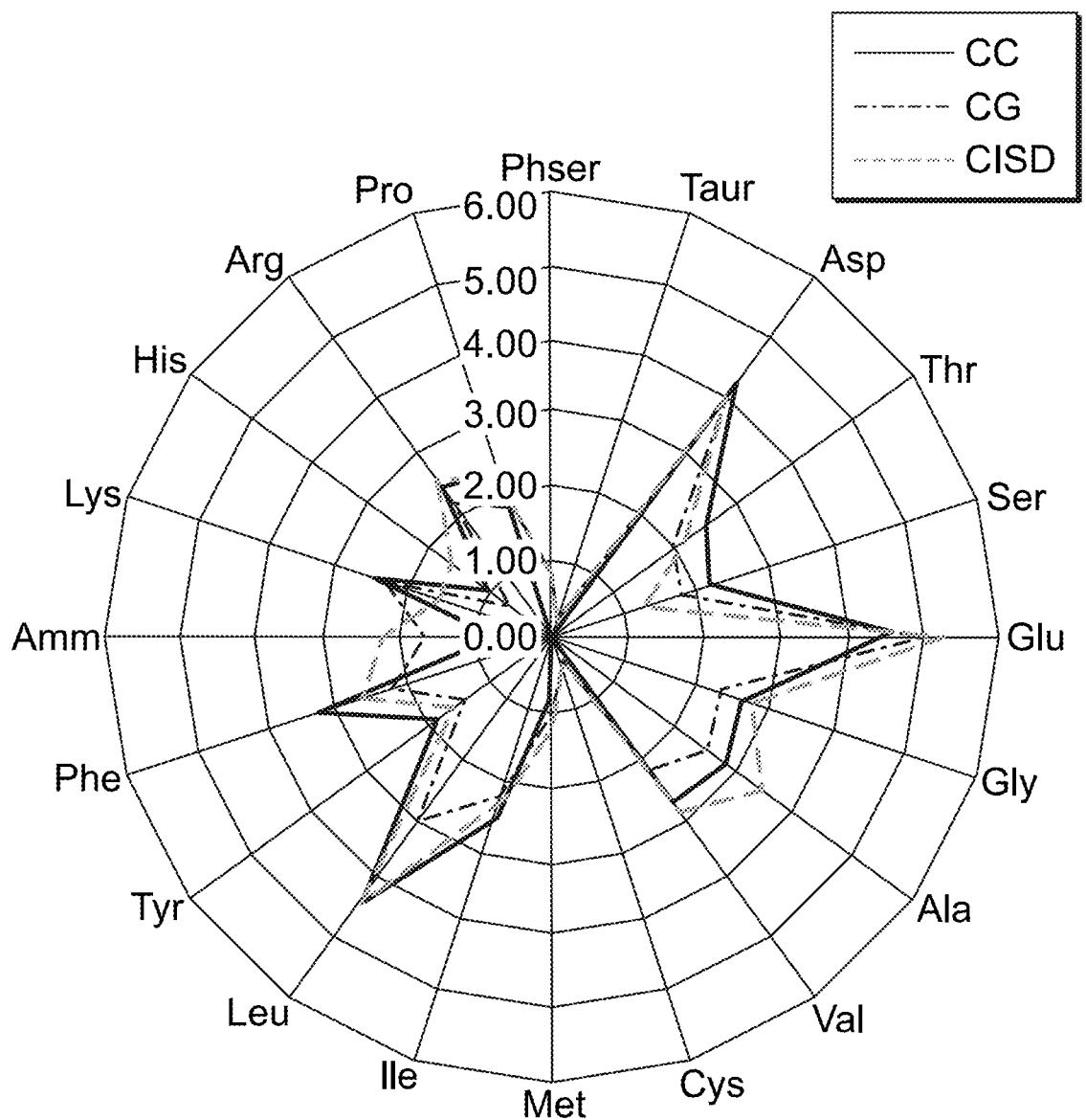
FIG. 22 is a radar chart mapping the total amino acid and ammonia concentrations (% DW (dry weight)) measured in a dried chloroplast composition 4E prepared according to the process described herein (4E, Red), and microalgae *Isochrysis galbana* (CISO; Blue) and *Chaetoceros gracilis* (CG; Black)

The green solids suspension (4B) comprises structures with an average particle size of 4-6 microns, which corresponds to the dimension of intact chloroplasts. The intactness of chloroplasts was measured using different approaches namely dynamic light scattering and microscopic observation (as shown in FIGS. 20A and B), allocation of Rubisco (as shown in FIG. 21), lipid composition (Table 4) and amino acid composition (FIG. 22).

Green Solids Characterization

Figure 20A:
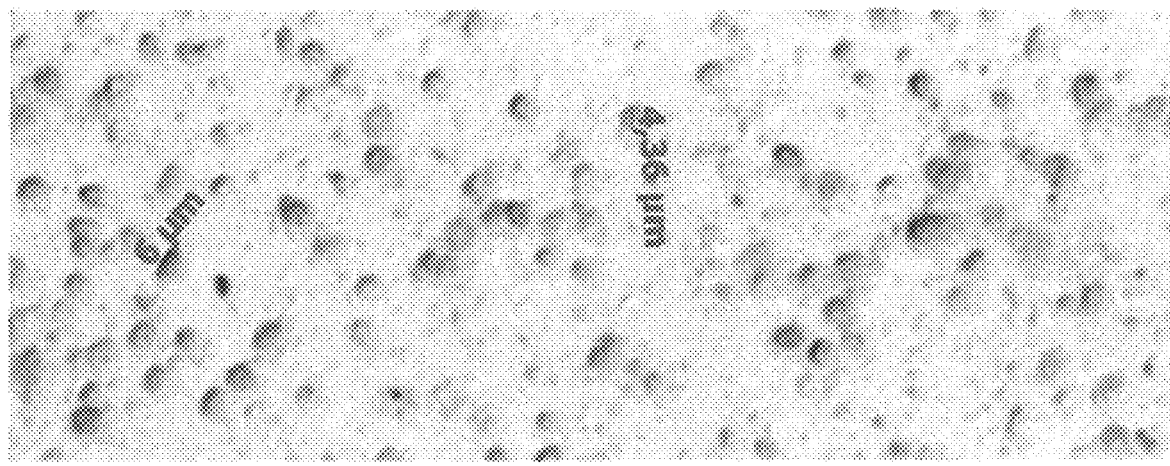
FIG. 20A is an image depicting microscopic examination of a green solids suspension (e.g. 4B) after fractionation as described herein.

FIG. 20A is a microscopic image of chloroplasts comprised in the green solids suspension after fractionation (4B). As can be seen, the chloroplasts appear mostly intact and have an average diameter of about 4-6 microns.

Figure 20B:
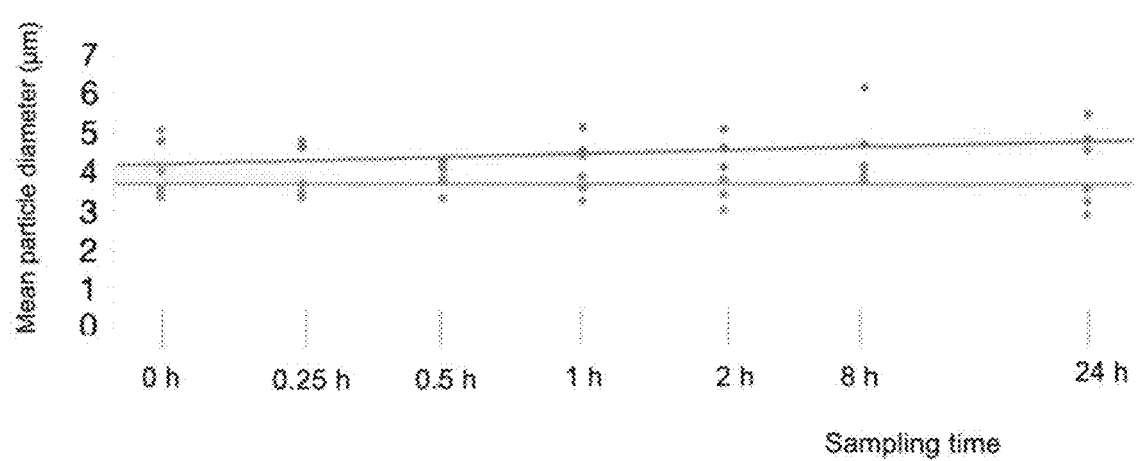
FIG. 20B is a graph showing the mean particle diameters (μm) measured in 1 L suspensions of dried chloroplast concentrate (e.g. 4E) in seawater over a 24-hour period.

Mean chloroplast diameters (μm) was measured in 1L suspensions of dried chloroplast concentrate (4E) resuspended in seawater over a 24-hour period. Samples were taken at 0, 0.25, 0.5, 1, 2, 8 and 24 hours respectively. Particles in each sample were digitally photographed with a compound microscope and measured with image analysis software. As shown in FIG. 20B, each point above represents the value determined for a single replicate; many replicates were measured for each sampling period. Two lines of estimated means are shown in FIG. 20B; the lower line is the average mean of particles resuspensed without agitation and the higher line is the average mean of particles resuspended with agitation. These results show a very limited difference in average mean with or without agitation. As can be seen, even after drying and resuspension, the average particle diameter remained at about 4 microns, demonstrating that chloroplast integrity was maintained.

Allocation of Rubisco

Distribution of Rubisco (heavy subunit) in the liquid phase and solid particles of green juice (14% solids, vol/vol) was analyzed by western blotting (as shown in FIG. 21). As described extensively in example 7 hereinabove, the different products analyzed by western blotting are presented in summary hereinafter. This green juice (2G) was acidified to pH 5 with diluted citric acid and passed through a CSC-15 centrifuge (GEA) at 10 000 g. The residence time in the centrifuge was estimated at 17 seconds. In these conditions, the brown juice (3B) contained less than 12% solids. The remaining solids therein were removed by passage through a 300 kD ceramic filter membrane under tangential flow. The chloroplast concentrate (3CC) was recovered at about 40% solids. It was dried in a spray dryer while maximum temperature of the particles was maintained at all times under 45° C. in order to obtain dry chloroplast composition (4E). The clarified brown juice (3D) was dried by lyophilization. As a control, whole alfalfa leaves (same original sample) was lyophilized and pulverized. The dried clarified brown juice (3D), dried chloroplast composition (4E) and whole leaf control were prepared in SDS-PAGE loading buffer and loaded on gels. An equivalent of 4 and 1.6 ug of dried chloroplast concentrate (4E) was loaded in wells 2 and 9, respectively. An equivalent of 4 and 1.6 ug of lyophilized whole alfalfa leaf was loaded in wells 1 and 8 respectively. A Rubisco std (Rubisco, purified heavy chain, Agrisera) was loaded in wells 4 (60 ng), 5 (30 ng) and 6 (15 ng). An equivalent of 1.6 ug of lyophilized clarified brown juice (3D) was loaded in well 7. T After migration (10% acrylamide), the proteins were transblotted unto PVDF membranes, washed in 3% casein and Rubisco was incubated in a rabbit an anti-Rubisco heavy chain immunoreagent (Rbcl, Agrisera) and detected with a goat anti-rabbit IgG.

The Western blotting results show that the Rubisco protein remains sequestered in the chloroplasts throughout the fractionation process. It is estimated is that well 7 contained less than 5 times the signal seen in well 6, that contained 15 ng of pure Rubisco. Accordingly, it was estimated that well 9 contained in excess of 2 times more signal than well 4, and so, in excess of 120 ng of Rubisco. Thus, it was estimated that the minimum ratio of relative content in Rubisco of these two fractions was 3 ng (content of well 7)/120 ng (content of well 9×10), i.e. $2.5 \times 10^{-2}$. These results suggest that less than 2.5% of the total Rubisco content was released from chloroplasts during fractionation with the corollary estimate that less than 2.5% of the chloroplasts were broken during fractionation (i.e. greater than 97.5% of the chloroplasts remained intact).

These findings are in contrast with the results obtained from conventional fractionations under harsh mechanical and chemical conditions where most of the Rubisco was recovered en masse in the liquid portion (Levesque and Rambourg 2002) as so called white protein. Thus, it was shown that the following factors specific to the described process, among others, contributed significantly in the maintenance of chloroplast intactness:

1. Use of harvesters with sharp blades and cut tables to decrease fiber size to <3-5 cm without crushing the biomass
2. Use of low screw speed and cone pressure to reduce shearing, pressure differentials and heat build-up
3. Use of mild acidification (pH above 4.5) to induce reversible coagulation and help sedimentation
4. Use of spray drying for dewatering,
5. Maintaining the temperature of particles at or below 45° C. at all times.

Amino Acid Composition of the Green Chloroplast Concentrate

The outer shell of microalgae is far more resistant to mechanical disruption than the outer membranes of chloroplasts. However, most microalgae are single-celled in which is found a single (or limited number of) chloroplast. Thus, preparations of microalgae for human consumption (for example *Chlorella*) or as aquafeed either consists of whole dried microalgae (human consumption) or whole live microalgae (aquafeed) in which the major protein contributions come from Rubisco and membrane proteins of the thylakoids.

As chloroplasts are maintained whole during fractionation of the alfalfa leafy biomass and washed of contaminating plant cytosolic proteins, the amino acid composition of the washed chloroplast suspension (4B) mimic closely that of microalgae. A complete comparison of amino acid composition of the presently disclosed washed chloroplast suspension (4B), referred to as chloroplast concentrate (CC) in FIG. 22, *Isochrysis galbana* Cayman strain (CISO) and *Chaetoceros gracilis* (CG) is given as example herein (FIG. 22).

The same is true for phospholipids that represent the bulk of membrane lipids in chloroplasts and microalgae, as shown in Table 4. One striking evidence that was revealed through this analysis is that chloroplast concentrate (CC), also identified hereinbefore as 4B, washed chloroplast suspension, and 4E, for the dried form, dry chloroplast composition, from alfalfa contain as a whole in excess of 20% of total lipids, and almost all of them as phospholipids, compared to the two control marine microalgae, namely *Isochrysis galbana* Cayman strain (CISO) and *Chaetoceros gracilis* (CG), which contain an average of 9% of total lipids. This is also in contrast with commercial alfalfa green protein concentrate whose content in lipids does not exceed 8%.

TABLE 4

Lipid class composition (% of total lipids) and total lipids (mg $g^{-1}$) measured in chloroplasts concentrate (CC), *Isochrysis galbana* Cayman strain (CISO) and *Chaetoceros gracilis* (CG).

| | CC | CISO | CG |
|---|---|---|---|
| Sterol esters | 0.00 | 0.13 | 0.19 |
| Triacylglycerols | 0.19 | 6.34 | 1.19 |
| Free fatty acids | 8.58 | 0.79 | 6.53 |
| Sterols | 1.11 | 0.45 | 2.17 |
| Phospholipids | 86.14 | 92.28 | 89.93 |
| Total lipids (% weight to weight on dry weight basis) | 20.7 | 9.7 | 8.2 |

Example 12—Comparison of End Products with Commercial Products

Objective

The main objective of the present example was to compare end products (1D, 2C, 4E) obtained from fractionation process as described herein with existing commercial products.

Method

Each and every result presented hereinafter was analyzed by independent laboratories using the following analytical methods references:

Moisture (M100T100_S:8)
Official Methods of Analysis of AOAC INTERNATIONAL, 18th Ed., Methods 925.09 and 926.08, AOAC INTERNATIONAL, Gaithersburg, MD, USA, (2005). (Modified).

ORAC (ORAC_S:8)
J AOAC Int., Vol. 94, No. 5, 2011, pg 1562-1566

Protein (N×6.25) Dumas Method (DGEN_S:11)
Official Methods of Analysis of AOAC INTERNATIONAL, 18th Ed., Methods 968.06 and 992.15, AOAC INTERNATIONAL, Gaithersburg, MD, USA, (2005). (Modified)

Crude Fiber (CFIB_S:5)
Official Methods of Analysis of AOAC INTERNATIONAL (2005) 18th Ed., AOAC INTERNATIONAL, Gaithersburg, MD, USA, Official Method 962.09.

Carotenes (CAR1_S:25) Covance Laboratories-Madison
Official Methods of Analysis, Method 2005.07, AOAC INTERNATIONAL, (modified).
Quackenbush, F. W., "Reverse Phase HPLC Separation of cis- and trans-Carotenoids and Its Application to Beta Carotenes in Food Materials," Journal of Liquid Chromatography, 10: 643-653 (1987) (modified).

Carotenes (CAR2_S:13)
Official Methods of Analysis of AOAC INTERNATIONAL (2005) 18th Ed., AOAC INTERNATIONAL, Gaithersburg, MD, USA, Official Method 941.15.
Quackenbush, F. W., Journal of Liquid Chromatography, 10:643-653, (1987). (Modified)

Chlorophyll (CPHL_S:3)
Official Methods of Analysis of AOAC INTERNATIONAL (2005) 18th Ed., AOAC Official Method 942.04. (Modified).

Fatty Acid Profile (FALT_S:36)
Official Method No. 996.06, Official Methods of Analysis of the AOAC INTERNATIONAL (modified), 19th Ed., AOAC INTERNATIONAL: Gaithersburg, Maryland (2012).
Official Methods and Recommended Practices of the AOCS, Official methods Ce 2b-11 (2011), Ce 1 h-05 (2009), Ce 1j-07 (2013), Ce 2-66 (2009), The American Oil Chemists' Society, Champaign, IL (modified).

Sugar Profile (SUGN_S:12)
Mason, B. S., and Slover, H. T., "A Gas Chromatographic Method for the Determination of Sugars in Foods," Journal of Agricultural and Food Chemistry 19(3):551-554 (1971). (Modified)
Brobst, K. M., "Gas-Liquid Chromatography of Trimethylsilyl Derivatives, Methods in Carbohydrate Chemistry," 6:3-8, Academic Press, New York, NY, (1972). (Modified)

Results

Macrofiber Composition (1D)

Comparison of Macrofiber composition (1D) with commercial alfalfa hay, a conventional feedstock for cows. The analysis was performed by an independent external government laboratory, namely the Centre de recherche en sciences animales de Deschambault.

It was found that the macrofiber composition (1D) may be an interesting alternative to alfalfa hay available on the market (see Table 5 below) as it has greater protein and moisture contents than hay but has a reduced saponin content. High saponin content has been linked to digestive disorders and to loss of palatability. It will be understood that the saponin concentration may vary largely based on the cultivar that was used.

TABLE 5

Distinct specifications of Macrofiber in comparison with alfalfa hay

|  | On Dry Basis (%) | |
| --- | --- | --- |
|  | Macrofibers 1D | Alfalfa hay |
| Protein (% dry basis) | 19.70 | 15.20 |
| Moisture (% water/total weight) | 62 | 13.5 |
| Medicagenic acid saponin (% relative to biomass standing in the field) | 34.7 | 100 |

Microfiber Composition (2C)

The composition of the microfiber composition 2C is comparable to that of wheat bran and dry banana. However, the microfiber composition 2C is an important green dietary fiber product. Compared (as shown in Table 6) to wheat bran (crude) and bananas (dehydrated), the microfiber composition 2C is well balanced with lower content in carbohydrates and lipids, and has a higher content in protein, beta-carotene and antioxidant compound, with a high relative content in fibers, equal to that of bananas but less than of crude wheat bran.

TABLE 6

Microfiber composition (2C) comparison with commercial products

|  | Microfiber 2C | Crude wheat bran | bananas dehydrated |
| --- | --- | --- | --- |
| % fibers | 9.9 | 42.8 | 9.9 |
| Protein (% dry basis) | 32.86 | 15.55 | 3.9 |

TABLE 6-continued

Microfiber composition (2C) comparison with commercial products

|  | Microfiber 2C | Crude wheat bran | bananas dehydrated |
| --- | --- | --- | --- |
| carbohydrates (%) | 51.04 | 65.00 | 88 |
| Beta-carotene (microg/g) | 96.00 | 0.06 | 1.01 |
| Total lipids (% dry basis) | 1.72 | 4.25 | 1.81 |
| Antioxidant (μmol TE/g) | 333.3 | ND | ND |

(1) Analyzed by independent laboratory Covance WI (www.covance.com)
(2) After www.nutritionvalue.org
ND = no data available Dry Chloroplast Composition 4E Comparison of dry chloroplast composition (4E) with existing commercial products. The dry chloroplast composition (4E) was be compared (Table 7 below) with microingredients claiming to have high protein, antioxidant, pigment and phospholipid contents. Except for protein content, the dry chloroplast composition (4E) ranked first or tied, compared to *Chlorella*, marine microalgae and an alfalfa protein concentrate.

TABLE 7

Distinct specifications of chloroplast composition 4E in comparison with recognized existing equivalents

|  | On Dry Basis (%) (1) | | | |
| --- | --- | --- | --- | --- |
|  | Chloroplast composition 4E | Chlorella (2) | Marine microalgae (3) | alfalfa protein concentrate (4) |
| Protein (% dry basis) | 52.70 | 61.09 | 39.6 | 50.20 |
| Chlorophyll (mg/g) | 30.5 | 7.7 | 4.6 | 7.2 |
| Total lipids (% dry basis) | 20.7 | 7.15 | 8.9 | 6.78 |
| Phospholipids (% on dry basis) | 17.5 | ND | 8.1 | ND |
| Omega 3 - fatty acid (% on dry basis) | 9.67 | 0.85 | 2.02 | ND |
| Beta Carotene (mg/g) | 5.48 | 0.18 | 5.64 | 0.90 |
| Antioxidant (umol TE/g) | 232.4 | 33.1 | ND | 7.2 |

(1) Analysis performed by Covance laboratories WI www.covance.com
(2) a commercial product (Organika ®), posted to be high % protein supplemental
(3) a natural compound generally produced in situ, posted to be high % protein supplemental
(4) a commercial compound (VITALFA ®), posted to be high % protein supplemental
ND no data available Example 13—Tracking of Hydrophobic and/or Amphiphilic Impurities by Saponins Objective Sampling upstream to downstream, many different intermediate and final products, such as: (0B) plants fragments; (2G) defibered green juice; (3D) clarified suspension; (3K) chloroplast suspension; (4B) washed chloroplast suspension permits to determine the off value components reduction in different steps of the process. Following the many different purification activities in the entire process, hydrophilic, hydrophobic and amphiphilic material can be flushed out in one or the other processing activities; somewhere all at the same time, being trapped or linked or associated to particular matter and somewhere by a specific hydrophilic or hydrophobic driven pathway.

In this example, Mediagenic acid saponin (MA saponin), an off nutritional compound responsible of digestive disorder, has been shown to be removed by the process of the present disclosure. It has been shown that the production of a distinct final product (4B), different form natural upstream products, separating and washing out off value components trough specific washing out activity, was achieved.

Results and Discussion

Measurement of Medicagenic acid saponins (MA saponins) were completed in all and each intermediate and final products. Following the mass balance of the MA saponins flowing trough the process, it was computed how much MA saponin was washed out from the chloroplast suspension.

TABLE 8

Distribution of MA saponin in different fractions

| Fraction | ID | total mass (kg) | Moisture content (%) | MA saponins concentration (mg/g) | MA Saponins mass balance (mg) | % relative to 0B | status |
|---|---|---|---|---|---|---|---|
| plant fragments | 0B | 77.4 | 79.1% | 0.860 | 13 932 | 100% | origin |
| defibered green juice | 2G | 49.9 | 91.4% | 2.3 | 4 575 | 32.84% | intermediate |
| chloroplast suspension | 3K | 10.9 | 85.2% | 1.578 | 2 556 | 18.35% | intermediate |
| washed chloroplast suspension | 4B | 9.7 | 87.4% | 1.422 | 1 745 | 12.53% | product |

Results presented in Table 8 shows the level in mg MA saponin/g total material (dry) and total mass of MA saponins computed in each fraction from defibered green juice. The right end column of the table present resulting % of saponins still measured in the downstream fraction compared to what was measured in plant fragments. It is necessary to feel mass balance in each fraction because total mass of compounds including water are different in all and each fraction.

The final product 4B is a completely different set than the natural defibered green juice extracted from the plant fragments. Separation by centrifugation (3A) permitted some extraction of off-taste and off-odour compounds such polyphenols and volatiles, but also off-nutritional as Medicagenic Acid saponins as shown in Table 8. Moreover, additional process step of a washing step (diluting first separation step jelly 3K in water and separating again to wash out residual off nutritional) permitted to reduce by 32% the total quantity of MA saponins in the final product compared to the intermediate form 3K. From a concentration perspective, the 4B fraction, washed chloroplast suspension is characterized by a MA saponins concentration 9.9% lower than the concentration observed in intermediate chloroplast suspension 3K, prior washing activity 4A.

Example 14—Triacontanol

Objective

The objective was to explore the potential for extracting triacontanol from products from the four fractionations of the process taking into consideration that this molecule could serve mainly as plant biostimulant.

Method

Four products (two fractions and two suspensions) were collected during the process and they were immediately frozen at −80° C. Triacontanol was extracted from samples by liquid-liquid extraction. Then, the lipophilic portion was dried and derivatized. A similar compound, the nonadecanoic acid methyl ester was added to the extraction liquid as a control. Analyses were carried out using a gas chromatography system and a mass spectrometric detection (GC-MS; Agilent). Triacontanol was used as the standard of quantification. The identification was based on the retention time and by NIST library. Moisture was calculated after drying at 105° C.

Results

TABLE 9

Quantity of triacontanol

| PRODUCTS | MACROFIBER FRACTION 1B | MICROFIBER FRACTION 2AA | CHLOROPLAST REDUCED SUSPENSION 3B | WASHED CHLOROPLAST SUSPENSION 4B |
|---|---|---|---|---|
| Quantity (ug/gr; dry sample) | 780 | 1923 | 981 | 39 |

Discussion

Triacontanol is a natural plant growth regulator found in epicuticular waxes. It has been reported that this natural molecule enhances the crop production and improves photosynthesis, protein synthesis, uptake of water and nutrients, enzymes activities, contents of free amino acids, and active constituents of essential oil in various crops. Triacontanol exploits the genetic potential of plant to a large extent. In the present investigation, triacontanol was detected in three of the four products, namely the chloroplast reduced suspension 3B, the macrofiber fraction 1B and the microfiber fraction 2AA. The latter could be the most interesting product to use for triacontanol extraction considering the higher concentration observed.

Example 15—Value-Added Protein and Peptide Molecules Extractable from Products Obtained from the Four Fractionations Objectives High end bio-sourced precursors may be selectively extracted from one or more product of the four fractionation processes herein described, namely the macrofiber fraction (1B), microfiber fraction (2AA), chloroplast reduced suspension (3B) and washed chloroplast suspension (4B). These precursors may have the potential to be used in specific industrial fields (e.g. pharmaceutical, nutraceutical, food, agriculture). Moreover, it is desirable to specify the location and to evaluate quantities of available peptides and located outside the proteins, that may be used as building blocks or as bio-sourced precursors.

Method

Four products, two solids (macrofiber fraction (1B) and microfiber fraction (2AA)) and two liquids (chloroplast reduced suspension (3B) and washed chloroplast suspension (4B)), were collected during the fractionation processes and were immediately frozen at −80° C. A sample of 200 mg of each of the two solid fractions was used and a sample of 0.5 mL of each of the two liquid fractions was used. A buffer containing ammonium bicarbonate (50 mM), sodium deoxycholate (0.5%), dithiothreitol (50 mM) and pepstatin (1 uM) was added to the tubes containing the solid fractions (1 mL of buffer) and liquid fraction (0.5 mL of buffer). Mechanical extraction with steal beads was performed for 2 min, each tube was then centrifuged, and the supernatants were collected. Acetone (5 volumes) was added to each tube for protein precipitation and, after centrifugation, the resulting supernatant was collected and desalted for peptide analysis. 1 µg of the resulting peptide mixture was analyzed using a 5600 Triple TOF mass spectrometer (Sciex). The method allowed detection of peptides between 8 and 30 amino acids long, corresponding to a molecular weight between approximately 800 Da to 3 kDa.

Rubisco was among the molecules identified in this example, and was further analyzed in Example 11 above.

Results

Figure 23:
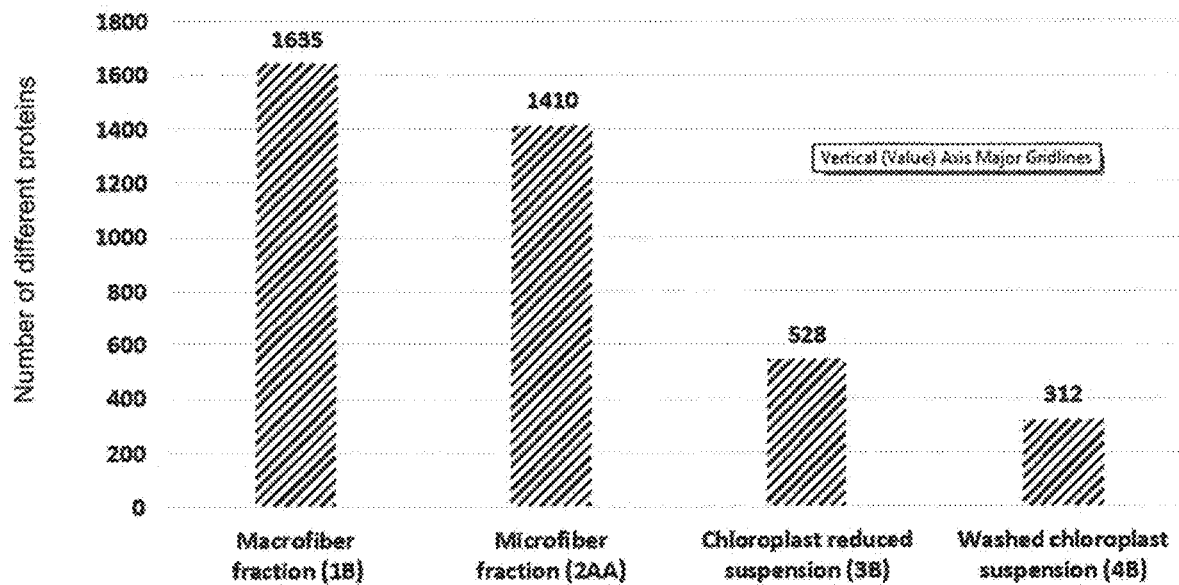
FIG. 23 is a bar graph showing the total number of different proteins identified in the macrofiber fraction (1B), microfiber fraction (2AA), chloroplast reduced suspension (3B) and washed chloroplast suspension (4B)
Figure 24:
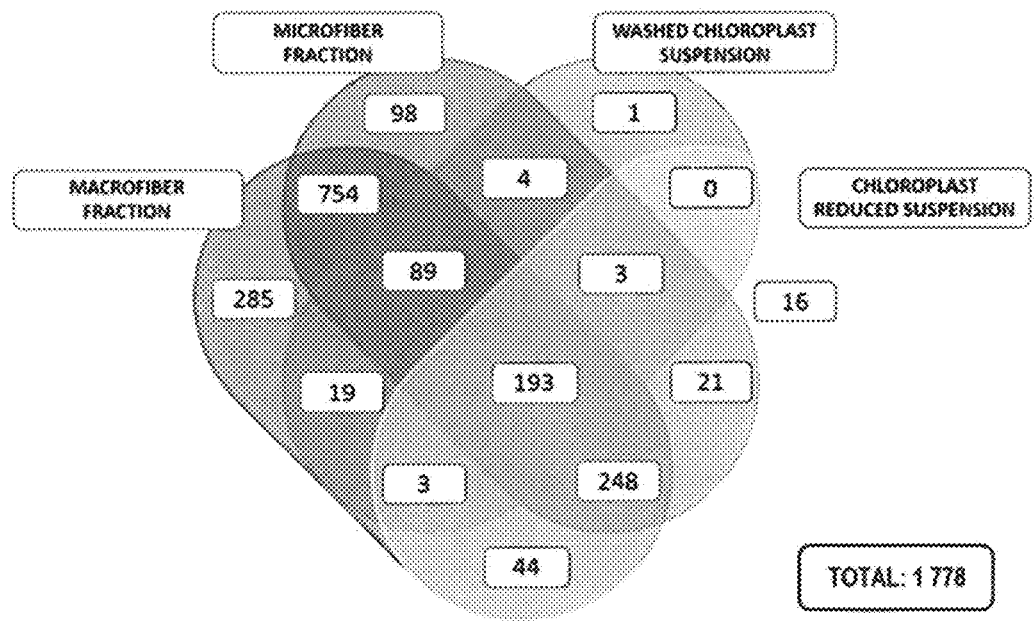
FIG. 24 is a Venn diagram providing an overview of the location of identified proteins in the macrofiber fraction (1B), microfiber fraction (2AA), chloroplast reduced suspension (3B) and washed chloroplast suspension (4B)

Proteins: The total number of different proteins identified per product of fractionation is shown in the bar graph of FIG. 23. FIG. 24 provides a breakdown of the number of identified proteins based on their location in various products of fractionation. Specific proteins are identified in Tables 10 to 16 and their locations are referred to in FIG. 25.

Figure 26:
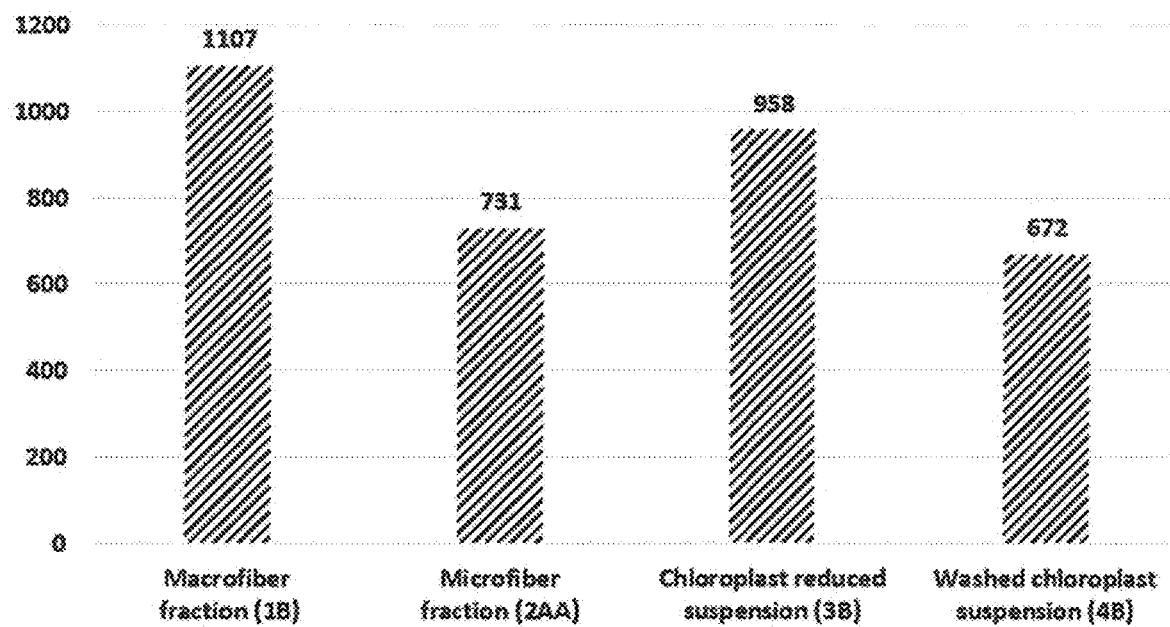
FIG. 26 is a bar graph showing the total number of different peptides, found outside the proteins, and identified in the macrofiber fraction (1B), microfiber fraction (2AA), chloroplast reduced suspension (3B) and washed chloroplast suspension (4B)
Figure 27:
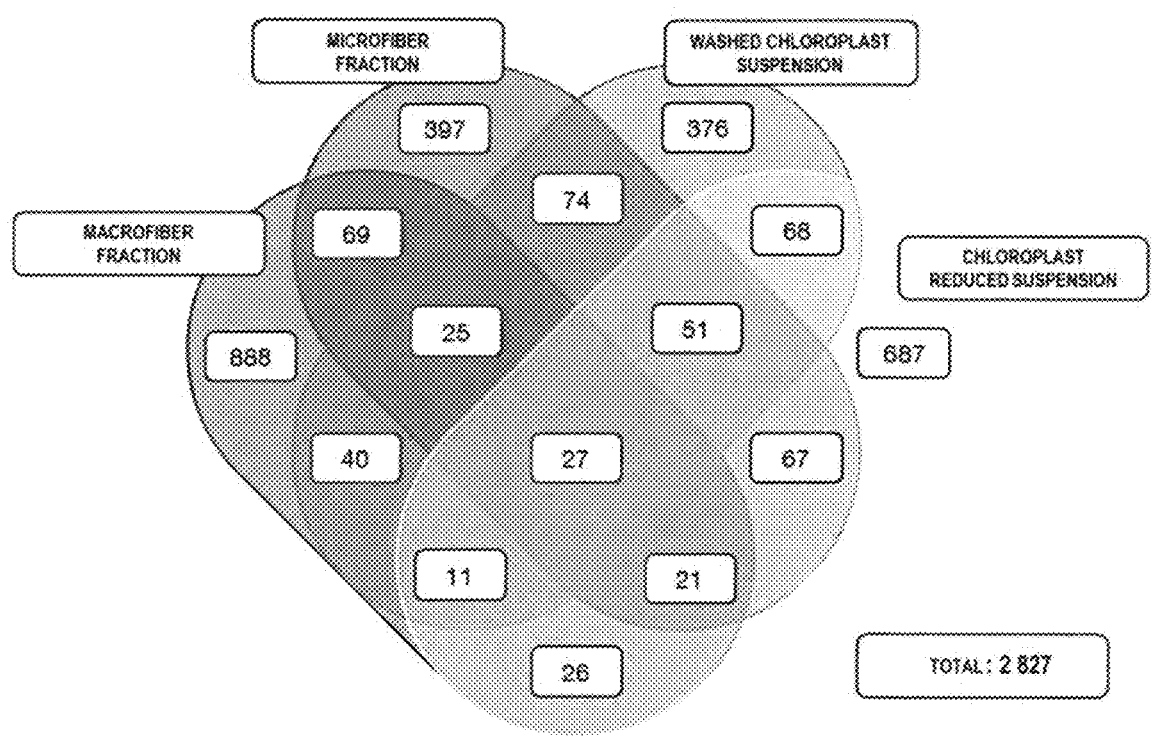
FIG. 27 is a Venn diagram providing an overview of the location of identified peptides in the macrofiber fraction (1B), microfiber fraction (2AA), chloroplast reduced suspension (3B) and washed chloroplast suspension (4B).

Peptides: Similarly, the total number of different peptides (found outside the proteins) identified per product of fractionation is shown in the bar graph of FIG. 26. FIG. 27 provides a breakdown of identified peptides based on their location in various products of fractionation.

TABLE 10

Some protein molecules that may have industrial applications

| TYPES OF PROTEIN | FUNCTIONS | APPLICATIONS | MACROFIBER FRACTION (1B) | MICROFIBER FRACTION (2AA) | CHLOROPLAST REDUCED SUSPENSION (3D) | WASHED CHLOROPLAST SUSPENSION (4B) |
|---|---|---|---|---|---|---|
| SUPEROXIDE DISMUTASE | Anti-oxidation and protection against free radicals | Pharmaceutical field Cosmetics Human and animal nutrition | X | X | X | X |
| HEAT SHOCK PROTEIN | Protection of cells against inflammatory and auto-immune diseases | Pharmaceutical field Human and animal nutrition | X | X | X | X |
| LIPOXYGENASE | Activation of lipid metabolism and production of molecules such as aldehydes and jasmonic acid | Human and animal nutrition Cosmetics Agriculture | X | X | X | X |
| CHITINASE | Hydrolysis of chitin Stimulation of mycorrhizal interaction | Agriculture | X | X | X | X |
| SUBTILISINE-LIKE SERINE PROTEASE | Induction of defense mechanisms | Agriculture | X | X | X | X |
| PEROXIDASE | Decomposition of toxic peroxides | Water and soil treatment Human and animal nutrition | X | X | X | X |
| AUXIN-BINDING PROTEIN | Release// production of the auxins | Agriculture | X | X | X | |
| MYO-INOSITOL PHOSPHATASE | Increase of Phosphorus assimilation | Agriculture Animal nutrition | X | X | | |
| BETAGALACTOSIDASE | Lactose degradation | Human nutrition Pharmaceutical field | X | | X | X |
| DEFENSINE | Anti-microbial activity | Pharmaceutical field | X | | | |

TABLE 10-continued

Some protein molecules that may have industrial applications

| TYPES OF PROTEIN | FUNCTIONS | APPLICATIONS | MACROFIBER FRACTION (1B) | MICROFIBER FRACTION (2AA) | CHLOROPLAST REDUCED SUSPENSION (3D) | WASHED CHLOROPLAST SUSPENSION (4B) |
|---|---|---|---|---|---|---|
|  | against pathogens, spoilage control | Cosmetics Human and animal nutrition Agriculture |  |  |  |  |
| NOD-FACTOR BINDING LECTIN-NUCLEOTIDE | Stimulation of interaction plant-microorganism | Agriculture |  |  | X |  |

TABLE 11

Location of Superoxide dismutase and Heat shock protein molecules

Figure 25:
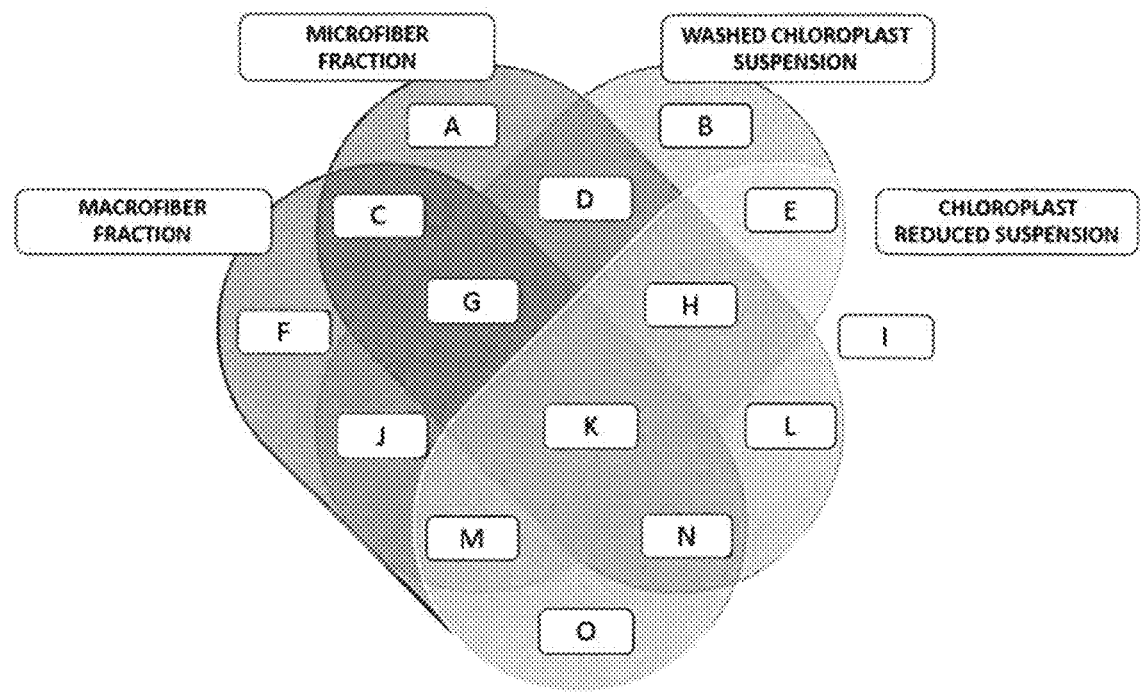
FIG. 25 is a Venn diagram specifically identifying different overlapping locations in the macrofiber fraction (1B), microfiber fraction (2AA), chloroplast reduced suspension (3B) and washed chloroplast suspension (4B)

| TYPES OF PROTEIN | IDENTIFICATION CODE | MW | RELATIVE ABUNDANCE * | Location in FIG. 25 |
|---|---|---|---|---|
| SUPEROXIDE DISMUTASE | SODCP_MEDSA | 21 kDa | MACROFIBER FRACTION: M<br>MICROFIBER FRACTION: H<br>WASHED CHLOROPLAST SUSPENSION: L<br>CHLOROPLAST REDUCED SUSPENSION: H | K |
|  | B7FGV9_MEDTR | 21 kDa | MACROFIBER FRACTION: L<br>MICROFIBER FRACTION: H<br>WASHED CHLOROPLAST SUSPENSION: L<br>CHLOROPLAST REDUCED SUSPENSION: M | K |
| HEATSHOCK PROTEIN 70 | Q5MGA8_MEDSA | 71 kDa | MACROFIBER FRACTION: H<br>MICROFIBER FRACTION: H<br>WASHED CHLOROPLAST SUSPENSION: L<br>CHLOROPLAST REDUCED SUSPENSION: M | K |
|  | Q2HT97_MEDTR | 71 kDa | MACROFIBER FRACTION: H<br>MICROFIBER FRACTION: H<br>WASHED CHLOROPLAST SUSPENSION: L<br>CHLOROPLAST REDUCED SUSPENSION: M | K |
|  | A0A072TUS4_MEDTR | 74 kDa | MACROFIBER FRACTION: H<br>MICROFIBER FRACTION: H<br>WASHED CHLOROPLAST SUSPENSION: L<br>CHLOROPLAST REDUCED SUSPENSION: L | K |
|  | A0A072TV12_MEDTR | 74 kDa | MACROFIBER FRACTION: H<br>MICROFIBER FRACTION: H<br>WASHED CHLOROPLAST SUSPENSION: M<br>CHLOROPLAST REDUCED SUSPENSION: M | K |
|  | Q1SKX2_MEDTR | 76 kDa | MACROFIBER FRACTION: H<br>MICROFIBER FRACTION: H<br>WASHED CHLOROPLAST SUSPENSION: L<br>CHLOROPLAST REDUCED SUSPENSION: M | K |
|  | A0A072UZC8_MEDTR | 99 kDa | MACROFIBER FRACTION: L<br>MICROFIBER FRACTION: L<br>CHLOROPLAST REDUCED SUSPENSION: L | N |
|  | A0A060CS45_MEDSA | 72 kDa | MACROFIBER FRACTION: H<br>MICROFIBER FRACTION: H<br>CHLOROPLAST REDUCED SUSPENSION: L | N |

* Relative Abundance: >30: High (H); 15-30: Moderate (M); 0-14: Low (L) according to the Protein Abundance Index method based on the number of sequenced peptides per protein; MW = molecular weight

TABLE 12

Location of lipoxygenase et Chitinase type molecules

| TYPES OF PROTEIN | IDENTIFICATION CODE | MW | RELATIVE ABUNDANCE * | Location in FIG. 25 |
|---|---|---|---|---|
| LIPOXYGENASE | A0A072TLZ7_MEDTR | 97 kDa | MACROFIBER FRACTION: H<br>MICROFIBER FRACTION: L<br>WASHED CHLOROPLAST SUSPENSION: L<br>CHLOROPLAST REDUCED SUSPENSION: M | K |
|  | G7LIY2_MEDTR | 98 kDa | MACROFIBER FRACTION: M | K |
|  | G7L7K0_MEDTR | 97 kDa | MACROFIBER FRACTION: L | F |
| CHITINASE | G7ID31_MEDTR | 31 kDa | MACROFIBER FRACTION: L<br>MICROFIBER FRACTION: M<br>WASHED CHLOROPLAST SUSPENSION: L<br>CHLOROPLAST REDUCED SUSPENSION: L | K |
|  | B8Y647_MEDSA | 30 kDa | MACROFIBER FRACTION: L<br>MICROFIBER FRACTION: L<br>WASHED CHLOROPLAST SUSPENSION: L<br>CHLOROPLAST REDUCED SUSPENSION: L | K |
|  | C3VM17_MEDSA | 33 kDa | MACROFIBER FRACTION: L<br>MICROFIBER FRACTION: M<br>WASHED CHLOROPLAST SUSPENSION: L<br>CHLOROPLAST REDUCED SUSPENSION: L | K |
|  | A0A072U5A4_MEDTR | 33 kDa | MACROFIBER FRACTION: L<br>MICROFIBER FRACTION: M<br>WASHED CHLOROPLAST SUSPENSION: L<br>CHLOROPLAST REDUCED SUSPENSION: L | N |
|  | G7LA76_MEDTR | 34 kDa | MACROFIBER COMPOSITION: L<br>MICROFIBER COMPOSITION: L<br>CHLOROPLAST REDUCED SUSPENSION: L | N |
|  | G7LA77_MEDTR | 35 kDa | MICROFIBER FRACTION: L<br>WASHED CHLOROPLAST SUSPENSION: L<br>CHLOROPLAST REDUCED SUSPENSION: L | H |
|  | D9IZ78_MEDSA | 34 kDa | MACROFIBER FRACTION: L<br>CHLOROPLAST REDUCED SUSPENSION: L | O |
|  | A0A072VMG3_MEDTR | 16 kDa | MACROFIBER FARCTION: L<br>CHLOROPLAST REDUCED SUSPENSION: L | O |

* Relative Abundance: >30: High (H); 15-30: Moderate (M); 0-14: Low (L) according to the Protein Abundance Index method based on the number of sequenced peptides per protein; MW = molecular weight

TABLE 13

Location of Subtilisine-like serine protease type molecule

| TYPES OF PROTEIN | IDENTIFICATION CODE | MW | RELATIVE ABUNDANCE) * | Location in FIG. 25 |
|---|---|---|---|---|
| SUBTILISINE-LIKE SERINE PROTEASE | G7L7L3_MEDTR | 84 kDa | MACROFIBER FRACTION: M<br>MICROFIBER FRACTION: H<br>WASHED CHLOROPLAST SUSPENSION: L<br>CHLOROPLAST REDUCED SUSPENSION: M | K |
|  | G7J8E0_MEDTR | 81 kDa | MACROFIBER FRACTION: L<br>MICROFIBER FRACTION: M<br>WASHED CHLOROPLAST SUSPENSION: L<br>CHLOROPLAST REDUCED SUSPENSION: M | K |

TABLE 13-continued

Location of Subtilisine-like serine protease type molecule

| TYPES OF PROTEIN | IDENTIFICATION CODE | MW | RELATIVE ABUNDANCE) * | Location in FIG. 25 |
|---|---|---|---|---|
| | G7ICF3_MEDTR | 77 kDa | MACROFIBER FRACTION: L<br>MICROFIBER FRACTION: M<br>CHLOROPLAST REDUCED SUSPENSION: L | N |
| | A0A072V371_MEDTR | 81 kDa | MACROFIBER FRACTION: L<br>MICROFIBER FRACTION: M<br>CHLOROPLAST REDUCED SUSPENSION: L | N |
| | G7JCT4_MEDTR | 80 kDa | MACROFIBER FRACTION: L<br>MICROFIBER FRACTION: H<br>CHLOROPLAST REDUCED SUSPENSION: L | N |
| | A0A072UXP6_MEDTR | 78 kDa | MACROFIBER FRACTION: L<br>MICROFIBER FRACTION: M | C |
| | A0A072VNF7_MEDTR | 82 kDa | MACROFIBER FRACTION: L<br>MICROFIBER FRACTION: L | C |
| | A0A072UXA2_MEDTR | 83 kDA | MACROFIBER FRACTION: L<br>MICROFIBER FRACTION: L | C |
| | A0A072TYE4_MEDTR | 82 kDa | MACROFIBER FRACTION: L<br>MICROFIBER FRACTION: L | C |
| | G7KEU6_MEDTR | 81 kGa | MACROFIBER FRACTION: L<br>MICROFIBER FRACTION: L | C |
| | G7KEU7_MEDTR | 80 kDa | MICROFIBER FRACTION: L<br>CHLOROPLAST REDUCED SUSPENSION: L | L |
| | G7KEU3_MEDTR | 81 kDa | MICROFIBER FRACTION: L | A |

\* Relative Abundance: >30: High (H); 15-30: Moderate (M); 0-14: Low (L) according to the Protein Abundance Index method based on the number of sequenced peptides per protein; MW = molecular weight

TABLE 14

Location of Peroxidase molecule

| TYPES OF PROTEIN | IDENTIFICATION CODE | MW | RELATIVE ABUNDANCE * | Location in FIG. 25 |
|---|---|---|---|---|
| PEROXIDASE | G7JCU3_MEDTR | 35 kDa | MACROFIBER FRACTION: L<br>MICROFIBER FRACTION: L<br>WASHED CHLOROPLAST SUSPENSION: L<br>CHLOROPLAST REDUCED SUSPENSION: H | K |
| | A0A072VI65_MEDTR | 35 kDa | MACROFIBER FRACTION: L<br>MICROFIBER FRACTION: L<br>WASHED CHLOROPLAST SUSPENSION: L<br>CHLOROPLAST REDUCED SUSPENSION: L | K |
| | O24081_MEDSA | 37 kDa | MACROFIBER FRACTION: L<br>MICROFIBER FRACTION: L<br>CHLOROPLAST REDUCED SUSPENSION: L | N |
| | A4UN76_MEDTR | 34 kDa | MACROFIBER FRACTION: L<br>MICROFIBER FRACTION: L<br>CHLOROPLAST REDUCED SUSPENSION: L | N |
| | G7JKV1_MEDTR | 38 kDA | MACROFIBER FRACTION: L<br>MICROFIBER FRACTION: L<br>CHLOROPLAST REDUCED SUSPENSION: L | N |
| | I3S041_MEDTR | 35 kDa | MACROFIBER FRACTION: L<br>MICROFIBER FRACTION: L<br>CHLOROPLAST REDUCED SUSPENSION: L | N |
| | A0A072TWY1_MEDTR | 35 kDa | MACROFIBER FRACTION: L<br>MICROFIBER FRACTION: L<br>CHLOROPLAST REDUCED SUSPENSION: L | N |
| | Q43791_MEDSA | 38 kDa | MACROFIBER FRACTION: M<br>MICROFIBER FRACTION: M<br>CHLOROPLAST REDUCED SUSPENSION: L | N |

TABLE 14-continued

Location of Peroxidase molecule

| TYPES OF PROTEIN | IDENTIFICATION CODE | MW | RELATIVE ABUNDANCE * | Location in FIG. 25 |
|---|---|---|---|---|
| | G7IJU2_MEDTR | 38 kDa | MACROFIBER FRACTION: L<br>MICROFIBER FRACTION: L<br>CHLOROPLAST REDUCED<br>SUSPENSION: L | N |
| | Q43790_MEDSA | 38 kDa | MACROFIBER FRACTION: L<br>MICROFIBER FRACTION: L<br>CHLOROPLAST REDUCED<br>SUSPENSION: L | N |
| | G7J9S1_MEDTR | 35 kDa | MACROFIBER FRACTION: L<br>MICROFIBER FRACTION: L<br>CHLOROPLAST REDUCED<br>SUSPENSION: L | N |
| | B7FGT3_MEDTR | 26 kDa | MACROFIBER FRACTION: L<br>MICROFIBER FRACTION: L | C |
| | G7J2Y6_MEDTR | 26 kDa | MACROFIBER FRACTION: L<br>MICROFIBER FRACTION: L | C |
| | A0A072URQ9_MEDTR | 36 kDa | MACROFIBER FRACTION: L<br>MICROFIBER FRACTION: L | C |
| | G7LI02_MEDTR | 18 kDa | MACROFIBER FRACTION: L<br>MICROFIBER FRACTION: L | C |
| | G7IU06_MEDTR | 36 kDa | MACROFIBER FRACTION: L<br>MICROFIBER FRACTION: L | C |
| | G7IJU0_MEDTR | 38 kDa | MACROFIBER FRACTION: L<br>MICROFIBER FRACTION: L | C |
| | G7JNF5_MEDTR | 32 kDa | MACROFIBER FRACTION: L<br>MICROFIBER FRACTION: L | C |
| | G7IKK4_MEDTR | 36 kDa | MACROFIBER FRACTION: L<br>MICROFIBER FRACTION: L | C |
| | Q40366_MEDSA | 38 kDa | MACROFIBER FRACTION: L<br>MICROFIBER FRACTION: H | C |
| | A0A0H3UW77_MEDSA | 27 Kda | MACROFIBER FRACTION: H<br>MICROFIBER FRACTION: M | C |
| | G7IM82_MEDTR | 34 Kda | MACROFIBER FRACTION: L<br>CHLOROPLAST REDUCED<br>SUSPENSION: L | O |
| | A0A072UXA0_MEDTR | 35 kDa | MACROFIBER FRACTION: L<br>CHLOROPLAST REDUCED<br>SUSPENSION: L | O |
| | G7LBF8_MEDTR | 19 kDa | MACROFIBER FRACTION: L<br>CHLOROPLAST REDUCED<br>SUSPENSION: L | O |
| | G7KFM2_MEDTR | 36 kDa | MACROFIBER FRACTION: L | F |
| | G7JXM8_MEDTR | 35 kDa | MACROFIBER FRACTION: L | F |
| | G7KH18_MEDTR | 35 kDa | MACROFIBER FRACTION: L | A |
| | A4UN77_MEDTR | 38 kDa | WASHED CHLOROPLAST<br>SUSPENSION: L | A |
| | A0A072VFU7_MEDTR | 38 kDa | WASHED CHLOROPLAST<br>SUSPENSION: L | I |

* Relative Abundance: >30: High (H); 15-30: Moderate (M); 0-14: Low (L) according to the Protein Abundance Index method based on the number of sequenced peptides per protein; MW = molecular weight

TABLE 15

Location of Auxin Binding Protein, Myo-Inositol Phosphatase and Betagalactosidase type molecule

| TYPES OF PROTEIN | IDENTIFICATION CODE | MW | RELATIVE ABUNDANCE * | Location in FIG. 25 |
|---|---|---|---|---|
| AUXIN-BINDING PROTEIN | G7L6U5_MEDTR | 81 kDa | MICROFIBER FRACTION: L | N |
| MYO-INOSITOL PHOSPHATASE | G7J4B5_MEDTR | 57 kDa | MACROFIBER FRACTION: L<br>MICROFIBER FRACTION: L | C |
| BETAGALAC-TOSIDASE | A0A072VC19_MEDTR | 88 kDa | MACROFIBER FRACTION: L<br>MICROFIBER FRACTION: L<br>CHLOROPLAST REDUCED<br>SUSPENSION: M | N |
| | G7IIN1_MEDTR | 93 kDa | MACROFIBER FRACTION: L<br>MICROFIBER FRACTION: L<br>CHLOROPLAST REDUCED<br>SUSPENSION: L | N |

TABLE 15-continued

Location of Auxin Binding Protein, Myo-Inositol Phosphatase and Betagalactosidase type molecule

| TYPES OF PROTEIN | IDENTIFICATION CODE | MW | RELATIVE ABUNDANCE * | Location in FIG. 25 |
|---|---|---|---|---|
| | G7JC84_MEDTR | 81 kDa | MACROFIBER FRACTION: L MICROFIBER FRACTION: L | C |
| | G7JC82_MEDTR | 88 kDa | MACROFIBER FRACTION: L MICROFIBER FRACTION: L | C |
| | A2Q570_MEDTR | 82 kDa | MACROFIBER FRACTION: L | F |
| | G7I5V0_MEDTR | 83 kDa | MACROFIBER FRACTION: L | F |
| | G7JPE5_MEDTR | 91 kDa | MACROFIBER FRACTION: L | F |
| | G7ICD0_MEDTR | 82 kD | MACROFIBER FRACTION: L | F |
| | G7LHU5_MEDTR | 101 kDa | CHLOROPLAST REDUCED SUSPENSION: L | I |

* Relative Abundance: >30: High (H); 15-30: Moderate (M); 0-14: Low (L) according to the Protein Abundance Index method based on the number of sequenced peptides per protein; MW = molecular weight

TABLE 16

Location of Defensin and Nod-factor-binding type molecule

| TYPES OF PROTEIN | IDENTIFICATION CODE | MW | RELATIVE ABUNDANCE * | Location in FIG. 25 |
|---|---|---|---|---|
| DEFENSIN | G7L736_MEDTR | 8 kDA | MACROFIBER FRACTION: L | F |
| NOD-FACTOR-BINDING | G7KZC5_MEDTR | 53 kDa | MACROFIBER FRACTION: L CHLOROPLAST REDUCED SUSPENSION: L | O |
| | G7KZD1_MEDTR | 50 kDa | CHLOROPLAST REDUCED SUSPENSION: L | I |

* Relative Abundance: >30: High (H); 15-30: Moderate (M); 0-14: Low (L) according to the Protein Abundance Index method based on the number of sequenced peptides per protein); MW = molecular weight Discussion and Conclusion A larger (5 fold) number of proteins was identified in the first product (macrofiber fraction 1B) compared to the fourth product (washed chloroplast suspension 4B), as shown in FIG. 23. Some of these proteins may be valuable at the industrial level. Prior moving towards industrial production, many factors are to be evaluated including the a) value of the final product; b) the price that could be obtained for the specific protein material as building block and/or precursor of the final product; and c) extraction and purification costs.

A large number of peptides (2,827) is also present in the four different products of fractionation, as shown in FIG. 27. The largest number of peptides is found in the first fraction (macrofiber fraction 1B) and in the third fraction (chloroplast reduced suspension 3B). As hereinabove, discussing about the protein valuation, more studies and experimentations will have to be achieved in order to set the economic potential of some of these peptides.

Example 16—Demonstration of the Intactness of Dried Chloroplasts Composition (4E) Prepared from Washed Chloroplast Suspension (4B) by the Use of Orthogonal Analytical Methods In this example, chloroplasts pastes (4B) were prepared as in example #6 and dried by lyophilisation. They were stored for more than 1 week before further processing. They were then resuspended in salt water and characterized for intactness by a series of orthogonal analytical approaches.

Flow Cytometry

Figure 28:
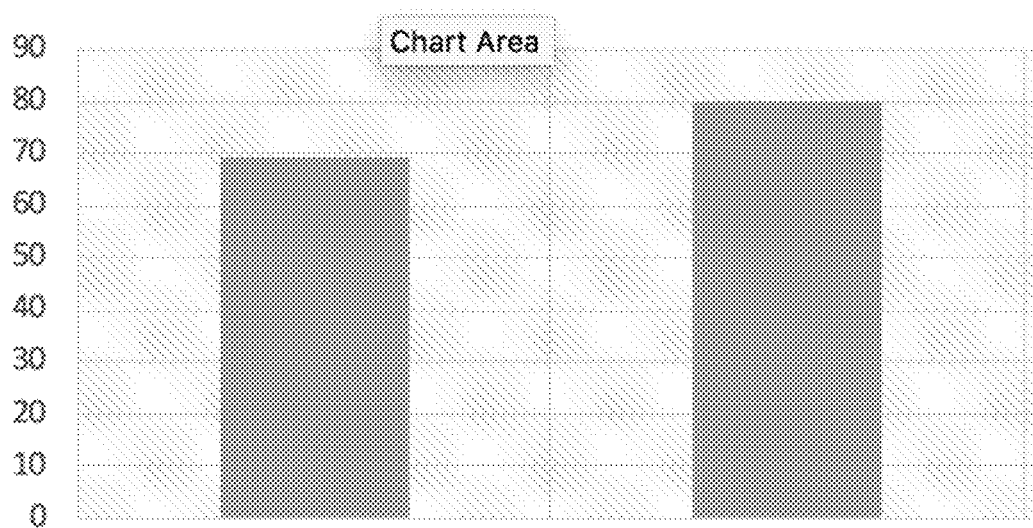
FIG. 28 represents the relative abundance of chloroplasts of dimension >2 um in rehydrated dried chloroplasts concentrates (4E). At the right, chloroplasts from washed chloroplast suspension (4B) prepared in 2017; at the left, chloroplasts from washed chloroplast suspension (4B) prepared in 2018.

Flow cytometry was used to determine the relative abundance of chloroplasts of dimension superior to 2 µm, with the assumption that upon rehydration, the inability of chloroplasts to recover their original shape and dimension would indicate irreversible damages to the outer and inner membrane systems. FIG. 28 clearly shows that a large proportion of rehydrated chloroplasts from pastes (4E) prepared either in 2017 and 2018 were of dimension higher than 2 µm, suggesting that they had remained intact through processing of the pastes (4E).

Figure 29:
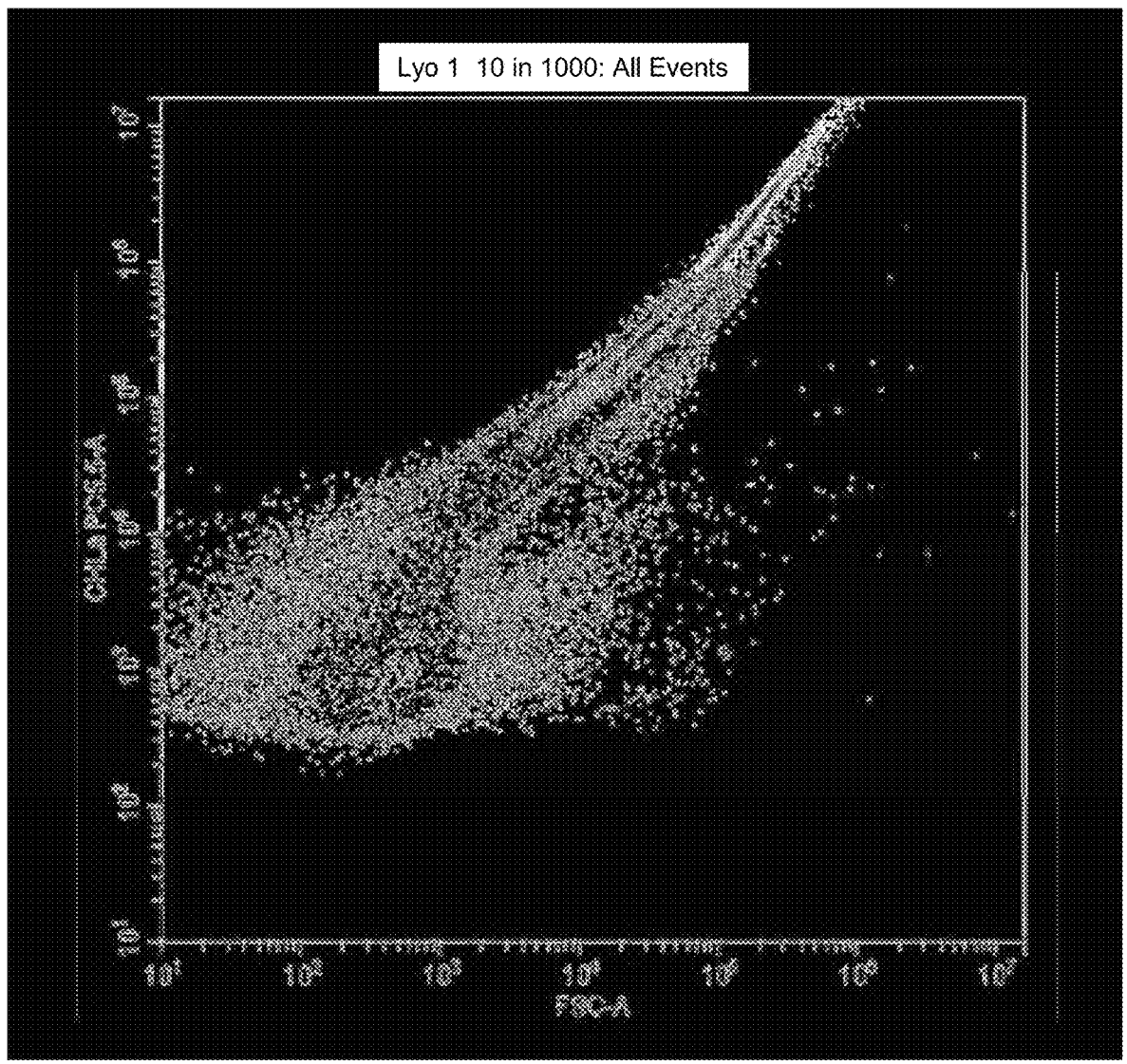
FIG. 29 shows to the proxy of the concentration in chloroplasts (fluorescence signal from chlorophyll a) in relation to the proxy of chloroplast dimension (FSC-A signal) in rehydrated lyophilized chloroplast concentrates. The intensity of fluorescence signal increases from black to white.

An additional demonstration came from plotting concentration proxies and fluorescence (chlorophyll-a) proxies. FIG. 29 demonstrates that fluorescence intensity was associated with chloroplasts of larger size, suggesting that intact chlorophyll-a was present in chloroplasts of dimension >2 µm.

Confocal Microscopy

Figure 30:
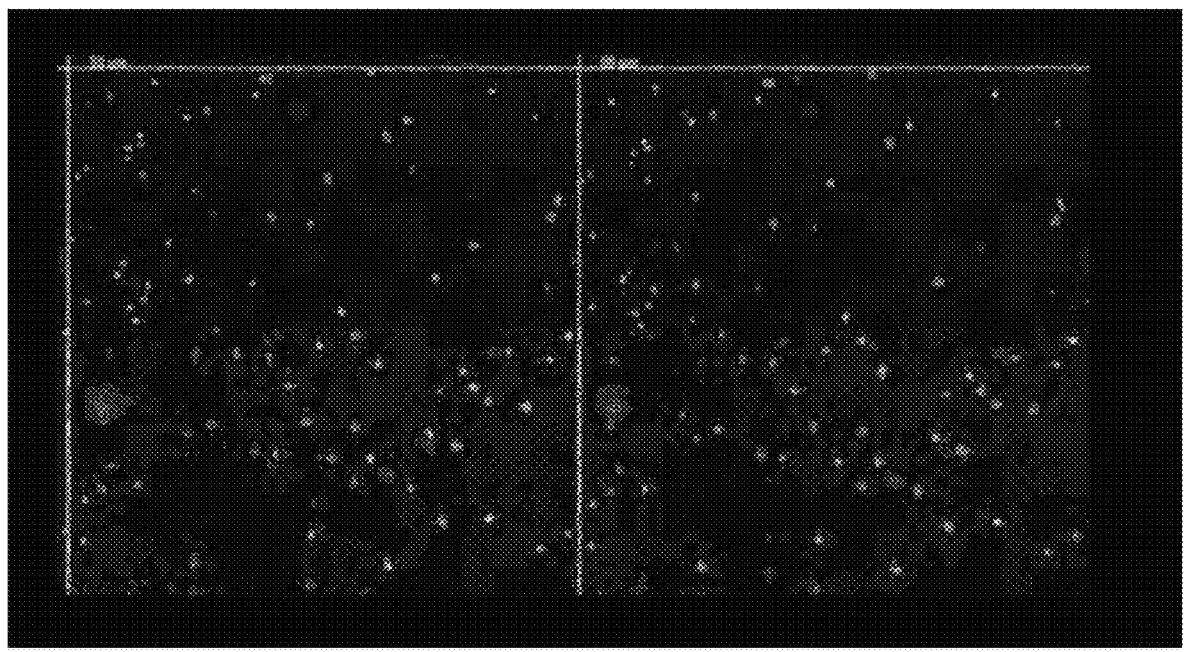
FIG. 30 shows emission of diluted rehydrated chloroplasts following excitation at 650 nm (chlorophyll a) shows a distinctive clear signal indicative of intact outer and inner membrane systems.

Diluted rehydrated chloroplasts, as the result of hydration of the dried chloroplast composition (4E), were examined under confocal microscopy after excitation at 650 nm (chlorophyll-a). The observations show chloroplasts of an average of ca 5 µm, with a with a sharp fluorescence delineation of chloroplasts outer boundaries, suggesting that inner and outer membrane systems were intact (see FIG. 30).

Visible Microscopy

Figure 31:
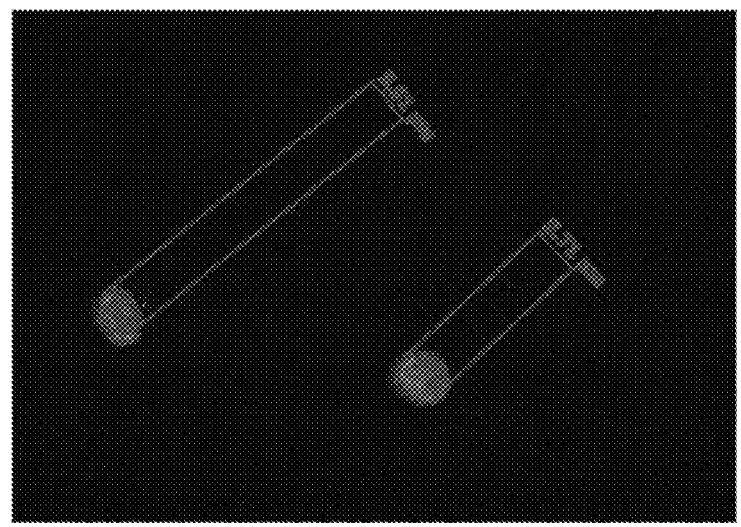
FIG. 31 represents microscopic observation of diluted rehydrated chloroplasts in suspension.
Figure 32:
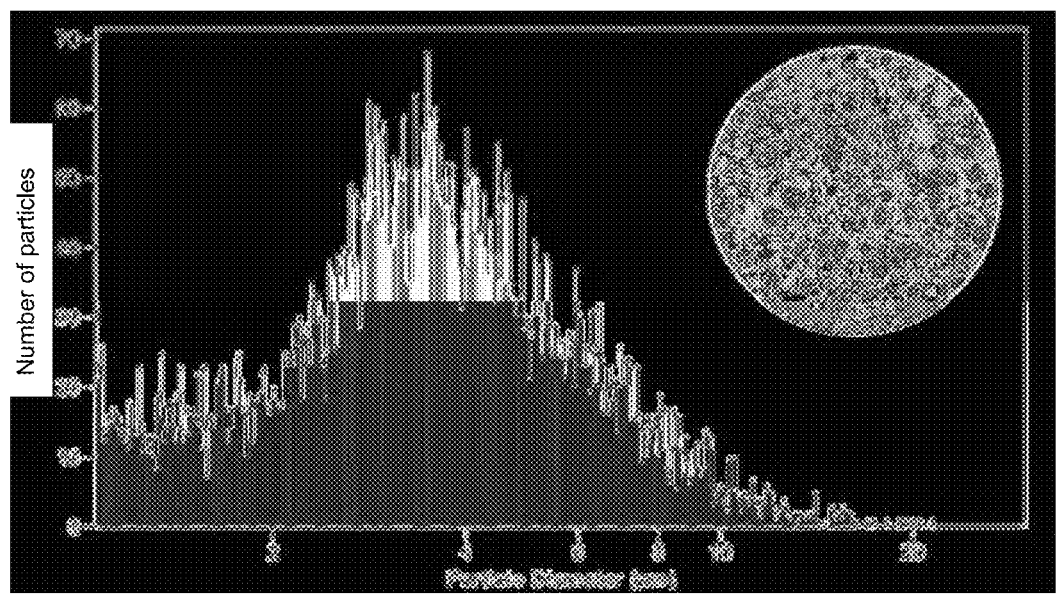
FIG. 32 represents size distribution and microscopic observation of rehydrated dried chloroplast composition (4E).

Repeated observations of diluted rehydrated chloroplasts under visible microscopy (FIG. 31) confirmed that they were of an average of 5.5 µm in length and of a shape that suggested intactness.

Overall, these analyses demonstrate that either washed chloroplast suspension (4B) and dried chloroplast suspension (4E) contained a large relative abundance of intact chloroplasts that maintained intactness through lyophilization and rehydration.

Example 17—Demonstration of the Water Miscibility of Dried Chloroplast Composition (4E)

In this example, a dried chloroplast composition (4E) was prepared as in example 6, and dried either by atomization or by lyophilization. These dried products (<8% water content) were stored in vacuum sealed packages for at least one month. They were then deposited in water tanks under mild agitation (air bubbling). Samples were taken within 60 seconds of deposition for size distribution analyses.

Dried chloroplast composition (4E) prepared as in example 6 resuspended easily and readily upon deposition in water, without significant agitation. Visual observations showed that upon deposition in water, the chloroplast particles dispersed and spread immediately, without formation of intermediary clumps. Size distribution analyses (FIG. 32) of samples taken within 60 seconds of deposition showed that the average particle size was slightly lower than 4 μm, which corresponds to the mean dimension of intact chloroplasts. Microscopic observation of these samples confirmed that the average particle in these samples had the structural characteristic of intact chloroplasts.

Dried chloroplast composition (4E) prepared as in example #16 also dispersed easily in water. FIG. 29 shows the size distribution of chloroplasts rehydrated from dried chloroplast composition (4E) as measured by flow cytometry (FSC). Either spray drying washed chloroplast suspension (4B) or lyophilising washed chloroplast suspension (4B) spread readily and easily as shown in FIG. 2 wherein the bulk of particulate material is found between 5 and 10 μm.

This demonstrates that in the conditions used in this example, but not restricted to, dried chloroplast composition (4E) prepared as in example 6, and dried either by atomization or by lyophilization, will resuspend easily in pure water. Other types of drying, such as vacuum drying and ring drying or other aqueous media for resuspension, such as salted water and buffers are likely to give the same results.

Example 18—Use of Differential Affinity for the Separation of Saponin Classes Between Alfalfa Sub-Fractions Saponins are glucosides of organic polycyclic cores (sapogenins) of different compositions. In most plants, saponins rarely occur as aglycones but the level and nature of glycosylation of their sapogenin core varies broadly. In alfalfa (*Medicago sativa* spp), two major classes of saponins are found. Saponins with an acidic sapogenin core such as medicagenic acids, zanhic acids, hederagenins, bayogenins, and saponins with a neutral sapogenin core, such as soyasapogenols (A, B). Medicagenic acids and soyasapogenols generally consist of more than 80% of the total saponin content.

Most saponins in alfalfa are linked to complex glycans at position C3-OH. The list of known glycan substitutes at this position for alfalfa saponins was presented by Tava and Avato 2006 Chemical and biological activity of triterpene Saponins from *Medicago* species.

Natural product communications 1(12): 1159-1180. January 2006. In addition, hederagenins, bayogenins, medicagenic acids and zanhic acids have a carboxyl group at position C28 that is generally esterified to another complex glycan chain. As hederagenins and bayogenins sapogenin core only has one carboxyl group at C28, their glucosides are generally not charged in aqueous solutions at physiological pHs. In contrast, medicagenic and zanhic acids have an additional carboxyl group at position C23 that is left unsubstituted and they behave like carboxylic acids in aqueous solutions at physiological pHs.

Thus, although all saponins have both hydrophilic and lipophilic characteristics, the difference in charge of their glucosides creates differences in behaviors in complex mixes such as crude plant extracts.

In this example, chloroplast suspension (3K) were separated from the microfiber depleted suspension (2G) as described in example 5. Differential affinity for the aqueous or lipid-rich fractions was used to enrich the aqueous fraction in acidic saponins such as medicagenic acids.

TABLE 17

Percentage of saponin types (on total saponin content) in fresh plant fragments (0B) and products (3B, 3K) of its fractionation.

| | Medicagenic acid | Bayogenin | Hederagenin | Soyasapogenol B | Soyasapogenol A |
|---|---|---|---|---|---|
| Plant fragments (0B) | 62 | 6 | 2 | 4 | 26 |
| Protein reduced suspension (3B) | 82 | 5 | 1 | 6 | 6 |
| Chloroplast suspension (3K) | 44 | 12 | 3 | 16 | 25 |

Table 17 shows the relative abundance of saponin types in fresh plant fragments (0B and its fractionation products (3B, 3K)). These results show a significant enrichment in medicagenic acids of the protein reduced suspension (3B) as the lipid-rich green solids (chloroplasts) are removed by centrifugation (see examples 5, 7, 13). In the conditions used for separation, 82% of the saponin content of the resulting clarified juice consisted of medicagenic acids, demonstrating that by the use of conditions in which medicagenic acids remain charged, they can be easily separated from soyasapogenol B and A by the use of their differential affinity for aqueous fractions. These conditions can be, but are not limited, pH adjustments, for example, adjustments to pH 5 with citrate, where green solids have a high tendency to sediment and where the carboxyl group of medicagenic acids is still negatively charged, as for most organic acids at pHs above 5.

Example 19 General Methods for Determination of Rubisco, Chlorophyll and cFBPP Levels The following methods were used for the analyses in Examples 20 and 21.

Materials and Methods

Followed is a standardized immunodeterction method for the quantification of the content in the Rubisco heavy subunit (Rbcl) and cytosolic fructose 1,6-bisphosphatase (cFBPase).

Dried powdered samples are homogenized at a ratio of ca. 10 mg of sample per mL (w/v) of extraction buffer 1× (Cedarlane #AS08-300). The homogenates are then mixed with 1 volume of 2× Laemmli buffer (Bio-Rad #161-0737) and heated at 100° C./10 min for denaturation. Denatured samples are separated on Stain-free TGX 4-20% acrylamide gels (Bio-Rad #456-1033) using a Mini-protean system (Bio-Rad #456-1033) in a Tris-glycine-SDS buffer (25 mM Tris, 192 mM glycine, 0.1% SDS (w/v), pH 8.3) at 200 volts for 30 minutes. The immunoblotting are performed on PVDF membranes (Bio-Rad #162-0260) using a Tris-glycine-methanol buffer (25 mM Tris, 192 mM glycine, 0.1% SDS (w/v), pH 8.3, 20% methanol) at 100 volts for 30 minutes according to manufacturer instructions. The blotted membranes are saturated for 1 hour at room temperature under agitation with a solution of 5% skim milk. For Rbcl detection, the primary antibody (Cedarlane #AS03-037) are diluted 1/10000 in 5% skim milk, incubated at room temperature for 1 hour and washed 5 times, 5 minutes, with TTBS (20 mM Tris pH 7.5, 500 mM NaCl, 0.1% tween 20). The secondary antibody (Cedarlane #AS09-602) is used at 1/10000 dilution in 5% skim milk and incubated in the same conditions. After 30 min of incubation, 1 µL of Streptactin (Bio-Rad #161-0380) is added to allow detection of the molecular weight markers (Bio-Rad #161-0376) during the chemiluminescence revelation. The membrane is washed 5 times, 5 minutes with TTBS, and the chemiluminescence detection is performed with luminol (Bio-Rad #170-5060) for 3 minutes with agitation and the images are analysed with ImageLab v6.1.

For the cFBPase, the primary antibody (Cedarlane #AS04-043) is diluted 1/5000 and the rest of the immunodetection is as for Rbcl. Chemiluminescence is performed on a ChemiDoc MP Imaging system (Bio-Rad #17001402).

Relative abundance of an enzyme, and in this case cytosolic FBPP can be reliably and quantitatively determined by immunodetection. This is accomplished through measurement of the optical density on immunoblots by digital scanners. Thus, under a given set of SDS-PAGE, immunoblotting and immunodetection conditions, one can assign a content value of a target antigen (here cytosolic FBPP) to optical density. For the purpose of determining a content in cytosolic FBPP in different preparations, one unit of cytosolic FBPP (cFBPP unit) is determined as one unit of optical density measured under the fixed conditions described in the Material and Methods section above.

Figure 33:
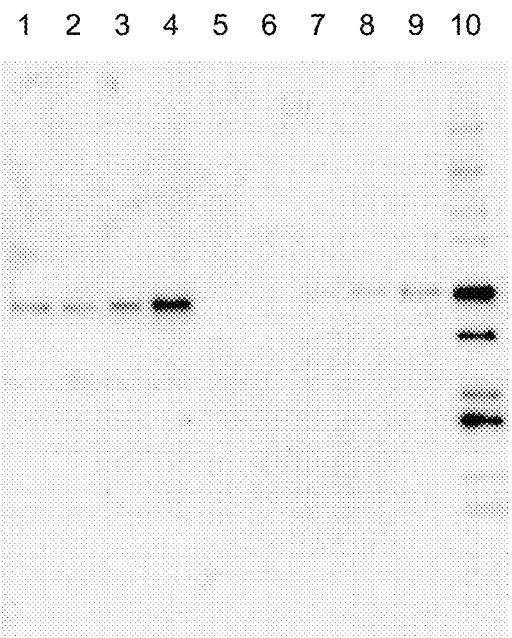
FIG. 33 represents an immunoblot of Rubisco where lane 1 is alfafa whole plant extract, lane 2 is green juice (2G), lane 3 is C1 (3K), lane 4 is C2 (4B), lane 5 is brown juice (3D), lane 6 is wash of C1, lanes 7, 8 and 9 are 8.25, 16.5 and 33 ng respectively of purified Rubisco (Agrisera #AS03 037A), and lane 10 is molecular weight marker.
Figure 34:
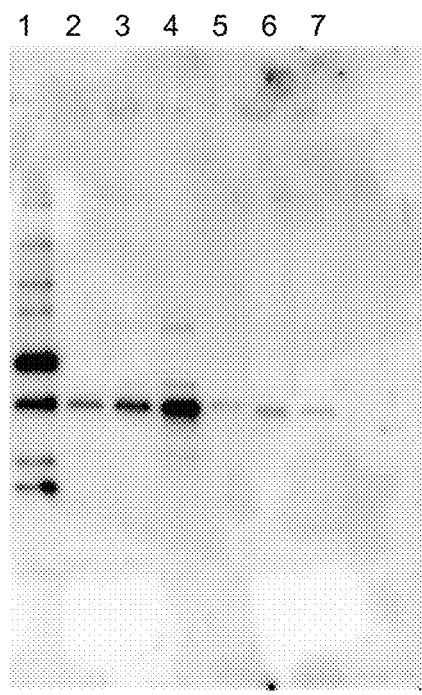
FIG. 34 represents an immunoblot of FBPP where lane 1 is molecular weight marker, lane 2 is whole alfalfa plant extract, lane 3 is green juice (2G), lane 4 is brown juice (3D), lane 5 is wash of C1, lane 6 is C1 (3K), and lane 7 is C2 (4B).

FIG. 33 shows a photo of the immunoblot of Rubisco.
FIG. 34 shows a photo of the immunoblot of cFBPP.

Table 18 shows the intensity measurements and quantities of chlorophyll, Rubisco, and cFBPPase. Table 19 shows ratios of chlorophyll, Rubisco, and cFBPPase calculated using the values of Table 18.

Wash of C1 in Tables 18 and 19 refers to the supernatant removed from the step 4A.

TABLE 18

Quantities and Intensities of Chlorophyll, Rubisco and cFBPPase

| Sample | Total chlorophyll (mg/g) | Rbcl intensity | Rbcl (ng/mg powder) | cFBPPase intensity | cFBPPase (intensity/mg) |
|---|---|---|---|---|---|
| Plants (0B) | 10.2 | 277560 | 35954.13093 | 1000132 | 20002640 |
| green juice (2G) | 13.8 | 245760 | 25610.40217 | 1797082 | 28652455.36 |
| brown juice (3D) | 0 | 0 | 1822.988776 | 4596596 | 66024073.54 |
| Wash of C1 | 0 | 0 | 2439.8 | 263051 | 5056728 |
| C1 (3K) | 25.4 | 420399 | 49140.8097 | 522077 | 9653790.68 |
| C2 (4B) | 31.4 | 1487308 | 139733.1725 | 206264 | 3174269.006 |

TABLE 19

Ratio of Chlorophyll, Rubisco and cFBPPase levels

| Sample | chlorophyll/cFBPPase (mg/intensity)*10000000 | Rbcl/cFBPase (ng/intensity)*100 | Rbcl/chlorophyll (intensity/mg)/1000 | Rbcl/chlorophyll (ng/mg) |
|---|---|---|---|---|
| Plants (0B) | 5.1 | 3.6 | 27 | 3.5 |
| green juice (2G) | 4.8 | 1.4 | 18 | 1.9 |
| brown juice (3D) | / | 0.0 | / | / |
| Wash of C1 | / | / | / | / |
| C1 (3K) | 26.3 | 9.4 | 17 | 1.9 |
| C2 (4B) | 98.9 | 67.7 | 47 | 4.5 |
| Ratio C1/C2 | 0.3 | 0.14 | 0.3 | 0.4 |

Example 20: Cytosolic Fructose-1,6-Bisphophatase (FBPP) Ratios

Cytosolic Fructose-1,6-bisphosphatase (FBPP) is a key enzyme of the metabolic pathway that results in sucrose synthesis from triose phosphate precursors produced by the chloroplast. This enzyme is also involved in gluconeogenesis from sucrose. Its activity is modulated by a complex balance of its two substrates but its levels in the cytosol are generally stable and controlled by photosynthetic activity. Thus, in a leaf cell, and more generally in cells of a photosynthetic tissue, photosynthetic capacity and chloroplast content are both linked to the levels of cytosolic FBPP.

In light of this, cytosolic FBPP levels (relative abundance) in a plant extract, or in any extract from photosynthetic tissue, is considered a highly reliable marker of cytosolic contamination, unlike other solubles from the cytosol for which levels (relative abundance) vary greatly depending on species, type of tissue, physiological status, stress, light exposition, diurnal cycles and other environmental or intrinsic conditions.

The levels of cytosolic FBPP can be quantitatively determined by immunodetection of the enzyme after separation by SDS-PAGE. This is preferable to the use of enzymatic assays for which levels can be influenced by the presence of soluble components in various extracts. Antibodies for such immunodetection are commercially available and their specificity and affinity standardized.

In this example, a rabbit anti-FBPP has been used for immunodetection (FIG. 34) of FBPP according to methods described in Example 19 in various fractions obtained from the process of the present disclosure. It can be seen in FIG. 34 that under these specific conditions of immunodetection, cytosolic FBPP can be detected and quantified in whole extracts in significant quantities (lanes 2-3) but is barely detectable in chloroplasts suspensions (lanes 6-7), demonstrating that the process of the present disclosure (for example process of FIG. 1) washes out all traces of soluble cytosolic content. FIG. 34 also shows that cFBPase content has been concentrated in the brown juice fraction obtained by sedimentation and filtering out of the chloroplasts. Calculation of cFBPase relative abundance (kunits per mg dry weight), an enrichment of ca 66-fold has been achieved by the sedimentation and filtering out of the chloroplasts.

In sharp contrast, it can be seen in FIG. 33 that the Rubisco heavy subunit, a marker specific to chloroplast was wholly sequestered in the enriched in chloroplast suspensions (lane 4) and undetectable in the brown juice (lane 5).

Taken together these results indicate that the general process of the present disclosure has protected the chloroplast membrane integrity and allow for the separation of intact chloroplast from contaminating soluble material from cytosolic origin, thus ensuring both purity and intactness.

These results also show that purity and intactness or integrity can be quantified by establishing ratios between both soluble and membrane components of the chloroplast and soluble components of the cytosol.

For example, as the heavy subunit is soluble in the chloroplast, its sequestration in the purified chloroplast suspension fraction is an indication that there has been no leakage during the process of the present disclosure and that Rubisco remains solely associated with components of the internal chloroplastic membrane system, beta carotene and chlorophyll.

Therefore, intactness and purity can be combined for the characterization of chloroplasts suspensions and used to demonstrate the efficacy of the process described in FIG. 34. Table 18 shows the intensity measurements and quantities of chlorophyll, Rubisco, and cFBPPase. Table 19 shows ratios of chlorophyll, Rubisco, and cFBPPase calculated using the values of Table 18. (See Example 19) As shown in Table 18, purity and intactness can be quantified by establishing ratios of either chlorophyll (chloroplast internal membrane component) or Rubisco (soluble chloroplast component) over a cytosolic marker such as cBFPase.

In this example, the chlorophyll/cFBPase ratio was ca 5 in the initial biomass and had increased to values close to ca 100 in the final chloroplast preparations (C2). Increases in this ratio can be used as a measure of the purity and intactness achieved by the process of the present disclosure, and thus a measure of composition that is the direct result of the efficacy of the process at both preserving intactness and washing out cytosolic material. It has been shown that the process of the present disclosure is able to produce chloroplast suspension with a ratio of chlorophyll/cFBPPase of at least 50 or higher.

Accordingly, increases in the Rbcl/cFBPase ratio can also be used as a measure of the purity and intactness achieved by the process of the present disclosure, and thus a measure of composition that is the direct result of the efficacy of the process at both preserving intactness and washing out cytosolic material. It has been shown that the process of the present disclosure is able to produce chloroplast suspension with a ratio of Rubisco/cFBPPase of at least 18 or higher.

Example 21: Protection of the Integrity of the Chloroplast in Order to Permit Selective Extraction of Pure Compounds Existing Mainly or Exclusively Inside the Chloroplast Selective extraction of intact chloroplasts without massive disruption of the integrity of those chloroplasts can be done through selective running specifications for processing equipment. Additives to the preparation have also been selected in order to minimise chemical modifications of the inner and outer membranes of the chloroplasts; the use of mild chemical additives can also prevent any disruption nor leakage of important organic material existing mainly or exclusively inside the chloroplast.

The present strategy is the protection of the integrity of the chloroplast in order to use directly as nutritional compound or to extract selective compounds existing inside. Integrity of the chloroplast have been directly checked by dynamic light scattering (as shown in FIG. 20A and FIG. 20B) and indirectly confirmed by the measurement of the metabolic activity. Checking both metabolic activity and physical integrity can confirm that the chloroplasts are intact without exception, whereas unlike dynamic light scattering, simple microscopic observation representing only a trivial testing without guarantee of intactness. As shown in FIGS. 20A and 20B, the chloroplasts of the present disclosure are substantially intact.

Significant deviation of bright green color of the preparation towards a light brown color may be a signal that lipid bilayer is corrupted by low heat conditions driving the leakage of inner material toward outer cytosol and dispersing pure material as Rubisco in the cytosol mix.

Chloroplast integrity check out could be also achieved by the measurement of the Rubisco/Chlorophyll ratio, where any leakage of the inner liquid material part of the chloroplast, including Rubisco, in the cytosol outer liquid will decrease the ratio compared to the original one where chlorophylls are stacked in the thylakoid structures inside the chloroplast. Examples 19 and 20 confirm Rubisco/Chlorophyll ratio evolution.

Indeed, observation of a high percentage of intact chloroplast in fraction 4B is observed at the same level in fractions 4E, the dry chloroplast composition and in fraction 4H, the liquid chloroplast composition; that being supported by the low stress conditioning of the fraction 4B to evolve to fractions 4E or 4H.

Experiments determining Rubisco and chlorophyll levels were conducted as shown in Example 19 (e.g. Materials and Methods). The results and ratios are described in Tables 18 and 19 in Example 19.

As demonstration of the integrity of the chloroplast, the calculated ratios between both soluble and membrane components of the chloroplast, as the ratio Rubisco/Chlorophyll (Table 19), show that Rubisco remains solely associated with Chlorophyll, component of the internal chloroplastic membrane system. Results in Table 19 demonstrate a ratio of 3.5 in plant fragment (0B) and a ratio of 4.5 in 4B, confirming the integrity of the chloroplast. If the chloroplasts were not intact, this ratio would become low due to the leakage of the soluble Rubisco outside the chloroplast.

Example 22: Purification of Chloroplasts

Introduction

Purifying chloroplasts from the vegetal biomass tissue is not enough, out of washing out off-tastes and off-odors compounds that corrupt commercial nutritive value of the proteinic material. Those off-nutritional value compounds reside in the cytosol outside the chloroplasts and could be hydrophilic (e.g. polyphenols); hydrophobic (e.g. volatile complex from fatty acids); and/or amphiphilic (e.g. saponins).

In order to obtain a commercial adapted distinct material, selective extraction will have to wash out off value material in multiple process activities. First, selective separation (3A) of the vegetal debris and amphiphilic material, such saponins, which can be drained in chloroplast reduced suspension (3B), permits to obtain a rich chloroplast suspension (3K). Continuing in a second selective separation (3C) of 3B, more amphiphilic material and hydrophilic material in 3D can be flushed out out of residual batch of chloroplasts (3CC). Combined 3K and 3CC, stills contaminated by polyphenols, volatiles and more saponins, can be further purified as much as feasible, by separation (4A), achieving a cleaned chloroplast suspension (4B) reduced in off-taste, off-odors and generally off-value compounds naturally existing in natural Alfalfa biomass material.

Tracking of Hydrophilic Impurities by cFBPP Ratios

Washing out off nutritional compounds existing in the cytosol around the chloroplast is the key to obtain a distinct material. Measuring the ratio of a protein, cytosolic Fructose-1,6-biphosphatase (cFPBB), existing mainly in cytosol, over the chlorophyll, which exists mainly in intact chloroplast, both in fractions 3K and 4B, can demonstrate the removal of hydrophilic material around the chloroplasts. An increase of the ratio of chlorophyll/cFBPP indicates removal hydrophilic material in the cytosol. Measurements of the cFPBB reduction represents the removal of many off-taste and off-odour in 4A washing activity. The cFPBB measurement is also independent of the Alfalfa cultivar selection, being mainly at the same level in the biomass fragments 0B, whatever the selected cultivar in use.

Purification of the chloroplast suspension (4B) can be observed at the same level in fractions 4E, the dry chloroplast composition and in fraction 4H, the liquid chloroplast composition; that being supported by the low stress conditioning of the fraction 4B to evolve to fractions 4E or 4H.

The results of cFBPP ratios are shown in Tables 18 and 19, and discussed in Example 20.

While the present disclosure has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present disclosure is found to be defined differently in a document incorporated herein by reference, the definition provided herein is to serve as the definition for the term.

What is claimed is:

1. A dry chloroplast composition comprising chloroplasts isolated from Fabaceae family plants, wherein said composition has a moisture content of less than about 8%,
and wherein said dry chloroplast composition has at least one ratio chosen from:
a ratio of chlorophyll/fructose 1,6-biphosphatase (FBPP) of about 50 to about 130, the ratio of chlorophyll/FBPP being $$\frac{\text{chlorophyll in (mg/g)}}{FBPP \text{ in (intensity/mg powder)}} \times 10000000,$$

the FBPP intensity being measured by immunoblot,
a ratio of Rubisco/chlorophyll of about 25 to about 65, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot,
a ratio of Rubisco/chlorophyll of about 2.5 ng/mg to about 6.5 ng/mg, the ratio of Rubisco/chlorophyll being $$\left(\frac{\text{Rubisco in ng/mg powder}}{\text{chlorophyll in (mg/g)}}\right)/1000,$$

and
a ratio of Rubisco/FBPP of about 18 to about 100, about 40 to about 90, about 50 to about 80, about 55 to about 75, about 60 to about 70, the ratio of Rubisco/FBPP being $$\left(\frac{\text{Rubisco in ng/mg powder}}{FBPP \text{ in intensity/mg}}\right) \times 100.$$

2. The composition of claim 1, wherein the plant is alfalfa.

3. The composition of claim 1, having a moisture content of less than about 4%.

4. The composition of claim 1, having a moisture content of about 3% to less than about 8%.

5. The composition of claim 1, wherein the composition is in powder form.

6. The composition of claim 1, further comprising an antioxidant, an antimicrobial agent, optionally a bacteriostatic or a bactericide, a fungicide, or mixtures thereof.

7. The composition of claim 1, further comprising an antioxidant and/or an antimicrobial agent.

8. The composition of claim 7, wherein the antioxidant and/or the antimicrobial agent is citric acid, metabisulfite, benzoate, optionally sodium metabisulfite, potassium metabisulfite, sodium benzoate or potassium benzoate.

9. The composition of claim 1, further comprising omega-3 fatty acids (e.g. eicosapentaenoic acid or docosahexaenoic acid), omega-6 fatty acids, vitamins, or mixtures thereof.

10. The composition of claim 1, wherein at least about 75 wt. % to about 90 wt. % of the solid content consists of chloroplasts.

11. The composition of claim 1, wherein n at about 90% of solid particles comprised in the composition have an average size of about 5 microns to about 10 microns.

12. The composition of claim 1, wherein at least about 80% of the chloroplasts have a preserved outer membrane integrity.

13. The composition of claim 1, wherein at least about 80% of the chloroplasts have a preserved inner membrane integrity.

14. The composition of claim 1, wherein at least about 80% of the chloroplasts have maintained metabolic activity as compared to chloroplasts comprised in a reference Fabaceae family plant.

15. The composition of claim 1, wherein at least about 80% of the chloroplasts are intact chloroplasts e.g. as determined by dynamic light scattering measurement and analysis.

16. The composition of claim 1, having a protein content greater than 45 wt. %.

17. The composition of claim 1, having a protein content of about 45 wt. % to about 55 wt.

18. The composition of claim 1, having a protein content of about 48 wt. % to about 52 wt. %.

19. The composition of claim 1, having a beta-carotene content of greater than about 300,000 IU/100 g.

20. The composition of claim 1, having a chlorophyll content of greater than about 20 mg/g.

21. The composition of claim 1, having a xanthophyll lutein content of greater than about 1.6 mg/g.

22. The composition of claim 1, having an antioxidant content of about 20,000 000 μmole TE/100 g to about 24,000 000 μmole TE/100 g.

23. The composition of claim 1, having a lipid content of about 5 wt. % to about 15 wt. %.

24. The composition of claim 1, having an omega-3 fatty acid content of about 2 wt. % to about 10 wt. %.

25. The composition of claim 1, having an omega-6 fatty acid content of about 1% to about 10%.

26. The composition of claim 1, having a lipid/protein ratio of about 0.2 to about 0.4.

27. The composition of claim 1, having a pH of less than about 5.0.

28. The composition of claim 1, having a protein content greater than 50 wt. % and a chlorophyll content greater than about 25 mg/g, wherein at least 70% of the chloroplasts are intact chloroplasts e.g. as determined by dynamic light scattering measurement and analysis.

29. The composition of claim 1, wherein the composition is encapsulated in a capsule, optionally an opaque capsule.

30. The composition of claim 1, wherein said ratio of chlorophyll/fructose 1,6-biphosphatase (FBPP) is about 95 to about 105, the ratio of chlorophyll/FBPP being $$\frac{\text{chlorophyll in (mg/g)}}{\text{FBPP in (intensity/mg powder)}} \times 10000000,$$

the FBPP intensity being measured by immunoblot.

31. The composition of claim 1, wherein said ratio of Rubisco/chlorophyll is about 40 to about 50, the ratio of Rubisco/chlorophyll being $$\left(\frac{\text{Rubisco in intensity}}{\text{chlorophyll in (mg/g)}}\right)/1000,$$

wherein the Rubisco intensity being measured by immunoblot.

32. The composition of claim 1, wherein said ratio of Rubisco/chlorophyll is about 4.0 ng/mg to about 5.0 ng/mg, the ratio of Rubisco/chlorophyll being $$\left(\frac{\text{Rubisco in ng/mg powder}}{\text{chlorophyll in (mg/g)}}\right)/1000.$$

33. The composition of claim 1, wherein said ratio of Rubisco/FBPP is about 55 to about 75, the ratio of Rubisco/FBPP being $$\left(\frac{\text{Rubisco in ng/mg powder}}{\text{FBPP in intensity/mg}}\right) \times 100.$$

* * * * *